United States Patent
Bossenmaier et al.

(10) Patent No.: US 9,840,565 B2
(45) Date of Patent: Dec. 12, 2017

(54) HER1 ANTIGEN BINDING PROTEINS BINDING TO THE BETA-HAIRPIN OF HER1

(71) Applicant: Hoffmann-La Roche Inc., Little Falls, NJ (US)

(72) Inventors: Birgit Bossenmaier, Seefeld (DE); Michael Gerg, Munich (DE); Gerhard Niederfellner, Oberhausen (DE); Carmen Peess, Tutzing (DE); Michael Schraeml, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/710,198

(22) Filed: May 12, 2015

(65) Prior Publication Data
US 2016/0002346 A1 Jan. 7, 2016

(30) Foreign Application Priority Data
May 14, 2014 (EP) .................... 14168320

(51) Int. Cl.
*A61K 39/395* (2006.01)
*C07K 16/30* (2006.01)
*C07K 16/28* (2006.01)
*C07K 14/71* (2006.01)
*G01N 33/68* (2006.01)
*A61K 39/00* (2006.01)

(52) U.S. Cl.
CPC .......... *C07K 16/3076* (2013.01); *C07K 14/71* (2013.01); *C07K 16/2863* (2013.01); *G01N 33/6854* (2013.01); *A61K 2039/505* (2013.01); *A61K 2039/6068* (2013.01); *C07K 2317/34* (2013.01); *C07K 2317/55* (2013.01); *C07K 2317/76* (2013.01); *C07K 2317/77* (2013.01)

(58) Field of Classification Search
None
See application file for complete search history.

(56) References Cited

U.S. PATENT DOCUMENTS 7,608,413 B1 * 10/2009 Joseloff ............ G01N 33/57438
424/130.1

FOREIGN PATENT DOCUMENTS

WO 2007/115571 A2 10/2007

OTHER PUBLICATIONS

Zhu et al (Immunology Letters, Jun. 2013, 153:33-40) (IDS).*
Lei Zhu et al., "B-cell epitope peptide vaccination targeting dimer interface of of epidermal growth factor receptor (EGFR)" Immunology Letters 153:33-40 ( 2013).
Written Opinion for PCT/EP2015/060491 (dated Jun 24, 2015).

* cited by examiner

*Primary Examiner* — Laura B Goddard

(57) ABSTRACT

The invention relates to anti-HER1 antigen binding proteins, e.g. anti-HER1 antibodies, that bind to the beta-hairpin of HER1, methods for selecting these antigen binding proteins, their preparation and use as medicament.

14 Claims, 9 Drawing Sheets

HER1 ANTIGEN BINDING PROTEINS BINDING TO THE BETA-HAIRPIN OF HER1

CROSS REFERENCE TO RELATED APPLICATIONS

Figure 1:
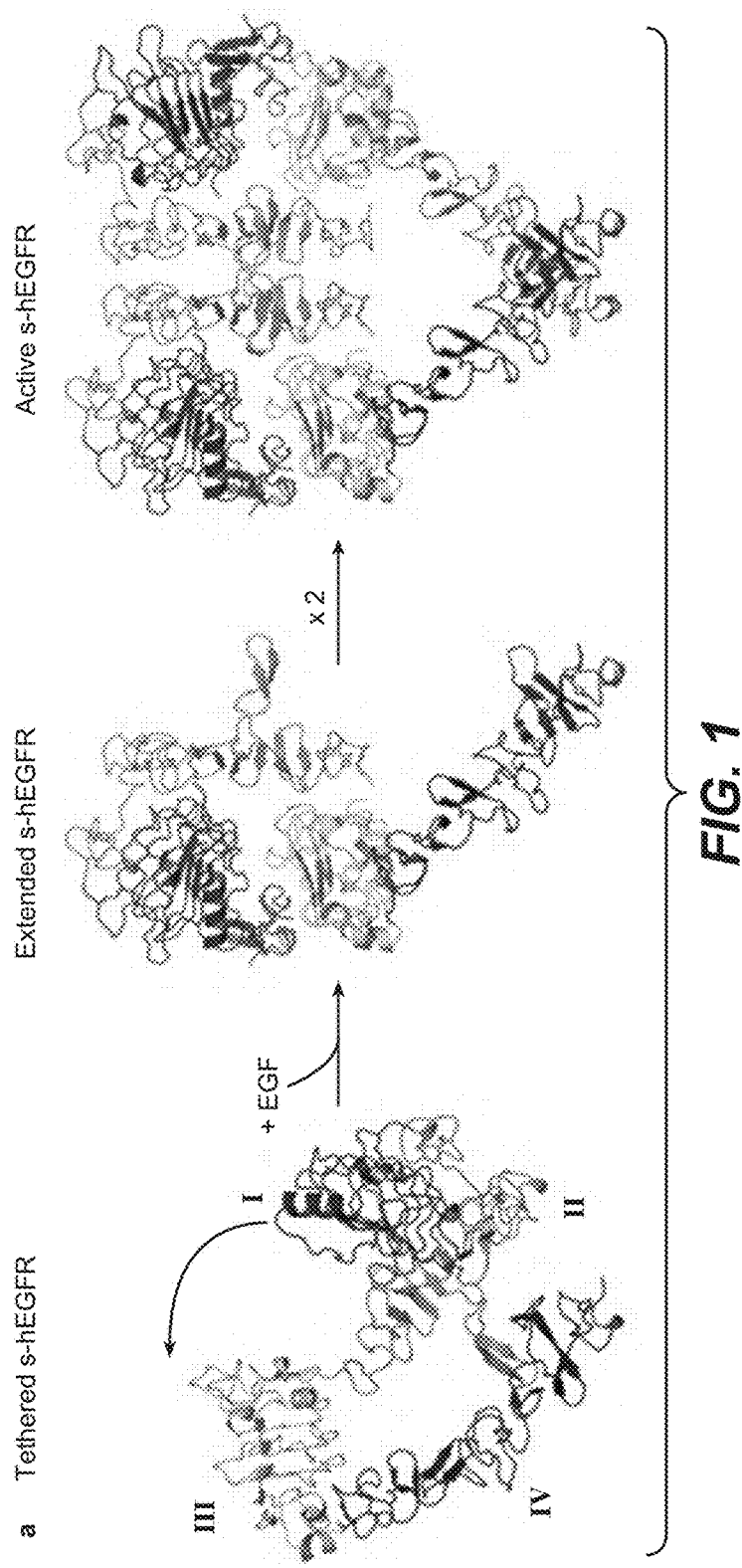

This application claims priority to European Patent Application No. EP 14168320.1 filed May 14, 2014, the disclosure of which is incorporated herein by reference in its entirety.

SEQUENCE LISTING

The present application contains a Sequence Listing which has been submitted in ASCII format via EFS-Web and is hereby incorporated by reference in its entirety. Said ASCII copy, created on May 11, 2015, is named P32121-US_ST25.txt and is 99,142 bytes in size.

FIELD OF THE INVENTION

The invention relates to anti-HER1 antigen binding proteins, e.g. anti-HER1 antibodies, that bind to the beta-hairpin of HER1, methods for selecting these antigen binding proteins, their preparation and use as medicament.

BACKGROUND OF THE INVENTION

The HER protein family consists of 4 members: HER1, also named epidermal growth factor receptor (EGFR) or ErbB-1, HER2, also named ErbB-2, ErbB-3, also named HER3 and ErbB-4, also named HER4. The ErbB family proteins are receptor tyrosine kinases and represent important mediators of cell growth, differentiation and survival. The HER family represent receptor proteins of different ligands of the epidermal growth factor family (EGF-family) like epidermal growth factor (EGF), the neuregulin (NRG) family, amphiregulin, and transforming growth factor-α (TGF-α).

HER1 and Anti-HER1 Antibodies

Human HER1 ((also known as epidermal growth factor receptor EGFR or Erb-B1) is a 170 kDa transmembrane receptor encoded by the c-erbB proto-oncogene, and exhibits intrinsic tyrosine kinase activity (Modjtahedi, H., et al., Br. J. Cancer 73 (1996) 228-235; Herbst, R. S., and Shin, D. M., Cancer 94 (2002) 1593-1611). SwissBase database entry P00533 provides the sequence of HER1 (SEQ ID NO: 2). There are also isoforms and variants of HER1 (e.g., alternative RNA transcripts, truncated versions, polymorphisms, etc.) including but not limited to those identified by Swissprot database entry numbers P00533-1, P00533-2, P00533-3, and P00533-4. HER1 is known to bind ligands including α), epidermal growth factor (EGF), transforming growth factor-α (TGF), amphiregulin, heparin-binding EGF (hb-EGF), betacellulin, and epiregulin (Herbst, R. S., and Shin, D. M., Cancer 94 (2002) 1593-1611; Mendelsohn, J., and Baselga, J., Oncogene 19 (2000) 6550-6565). HER1 regulates numerous cellular processes via tyrosine-kinase mediated signal transduction pathways, including, but not limited to, activation of signal transduction pathways that control cell proliferation, differentiation, cell survival, apoptosis, angiogenesis, mitogenesis, and metastasis (Atalay, G., et al., Ann. Oncology 14 (2003) 1346-1363; Tsao, A. S., and Herbst, R. S., Signal 4 (2003) 4-9; Herbst, R. S., and Shin, D. M., Cancer 94 (2002) 1593-1611; Modjtahedi, H., et al., Br. J. Cancer 73 (1996) 228-235).

Unconjugated monoclonal antibodies (mAbs) can be useful medicines for the treatment of cancer, as demonstrated by the U.S. Food and Drug Administration's approval of Trastuzumab (Herceptin™; Genentech Inc) for the treatment of advanced breast cancer (Grillo-Lopez, A. J., et al., Semin. Oncol. 26 (1999) 66-73; Goldenberg, M. M., Clin. Ther. 21 (1999) 309-18), Rituximab (Rituxan™; IDEC Pharmaceuticals, San Diego, Calif., and Genentech Inc., San Francisco, Calif.), for the treatment of CD20 positive B-cell, low-grade or follicular Non-Hodgkin's lymphoma, Gemtuzumab (Mylotarg™, Celltech/Wyeth-Ayerst) for the treatment of relapsed acute myeloid leukemia, and Alemtuzumab (CAMPATH™, Millenium Pharmaceuticals/Schering AG) for the treatment of B cell chronic lymphocytic leukemia. The success of these products relies not only on their efficacy but also on their outstanding safety profiles (Grillo-Lopez, A. J., et al., Semin. Oncol. 26 (1999) 66-73; Goldenberg, M. M., Clin. Ther. 21 (1999) 309-18). In spite of the achievements of these drugs, there is currently a large interest in obtaining higher specific antibody activity than what is typically afforded by unconjugated mAb therapy.

The results of a number of studies suggest that Fc-receptor-dependent mechanisms contribute substantially to the action of cytotoxic antibodies against tumors and indicate that an optimal antibody against tumors would bind preferentially to activation Fc receptors and minimally to the inhibitory partner FcγRIIB (Clynes, R. A., et al., Nature Medicine 6(4) (2000) 443-446; Kalergis, A. M., and Ravetch, J. V., J. Exp. Med. 195(12) (2002) 1653-1659. For example, the results of at least one study suggest that polymorphism in the FcγRIIIa receptor, in particular, is strongly associated with the efficacy of antibody therapy. (Cartron, G., et al., Blood 99 (3) (2002) 754-758). That study showed that patients homozygous for FcγRIIIa have a better response to Rituximab than heterozygous patients. The authors concluded that the superior response was due to better in vivo binding of the antibody to FcγRIIIa, which resulted in better ADCC activity against lymphoma cells (Cartron, G., et al., Blood 99(3) (2002) 754-758).

Various strategies to target EGFR and block EGFR signaling pathways have been reported. Small-molecule tyrosine kinase inhibitors like gefitinib, erlotinib, and CI-1033 block autophosphorylation of EGFR in the intracellular tyrosine kinase region, thereby inhibiting downstream signaling events (Tsao, A. S., and Herbst, R. S., Signal 4 (2003) 4-9). Monoclonal antibodies, on the other hand, target the extracellular portion of EGFR, which results in blocking ligand binding and thereby inhibits downstream events such as cell proliferation (Tsao, A. S., and Herbst, R. S., Signal 4 (2003) 4-9).

Several murine monoclonal antibodies have been generated which achieve such a block in vitro and which have been evaluated for their ability to affect tumor growth in mouse xenograft models (Masui, H., et al., Cancer Res. 46 (1986) 5592-5598; Masui, H., et al., Cancer Res. 44 (1984) 1002-1007; Goldstein, N., et al., Clin. Cancer Res. 1 (1995) 1311-1318). For example, EMD 55900 (EMD Pharmaceuticals) is a murine anti-EGFR monoclonal antibody that was raised against human epidermoid carcinoma cell line A431 and was tested in clinical studies of patients with advanced squamous cell carcinoma of the larynx or hypopharynx (Bier, H., et al., Eur. Arch. Otohinolaryngol. 252 (1995) 433-9). In addition, the rat monoclonal antibodies ICR16, ICR62, and ICR80, which bind the extracellular domain of EGFR, have been shown to be effective at inhibiting the binding of EGF and TGF-α the receptor. (Modjtahedi, H., et al., Int. J. Cancer 75 (1998) 310-316). The murine monoclonal antibody 425 is another MAb that was raised against the human A431 carcinoma cell line and was found to bind to a polypeptide epitope on the external domain of the human epidermal growth factor receptor. (Murthy, U., et al., Arch. Biochem. Biophys. 252(2) (1987) 549-560. A potential problem with the use of murine antibodies in therapeutic treatments is that non-human monoclonal antibodies can be recognized by the human host as a foreign protein; therefore, repeated injections of such foreign antibodies can lead to the induction of immune responses leading to harmful hypersensitivity reactions. For murine-based monoclonal antibodies, this is often referred to as a Human Anti-Mouse Antibody response, or "HAMA" response, or a Human Anti-Rat Antibody, or "HARA" response. Additionally, these "foreign" antibodies can be attacked by the immune system of the host such that they are, in effect, neutralized before they reach their target site. Furthermore, non-human monoclonal antibodies (e.g., murine monoclonal antibodies) typically lack human effector functionality, i.e., they are unable to, inter alia, mediate complement dependent lysis or lyse human target cells through antibody dependent cellular toxicity or Fc-receptor mediated phagocytosis.

Chimeric antibodies comprising portions of antibodies from two or more different species (e.g., mouse and human) have been developed as an alternative to "conjugated" antibodies. For example, U.S. Pat. No. 5,891,996 (Mateo de Acosta del Rio, C. M., et al.) discusses a mouse/human chimeric antibody, R3, directed against EGFR, and U.S. Pat. No. 5,558,864 discusses generation of chimeric and humanized forms of the murine anti-EGFR MAb 425. Also, IMC-C225 (Erbitux®; ImClone) is a chimeric mouse/human anti-EGFR monoclonal antibody (based on mouse M225 monoclonal antibody, which resulted in HAMA responses in human clinical trials) that has been reported to demonstrate antitumor efficacy in various human xenograft models. (Herbst, R. S., and Shin, D. M., Cancer 94 (2002) 1593-1611). The efficacy of IMC-C225 has been attributed to several mechanisms, including inhibition of cell events regulated by EGFR signaling pathways, and possibly by increased antibody-dependent cellular toxicity (ADCC) activity (Herbst, R. S., and Shin, D. M., Cancer 94 (2002) 1593-1611). IMC-C225 was also used in clinical trials, including in combination with radiotherapy and chemotherapy (Herbst, R. S., and Shin, D. M., Cancer 94 (2002) 1593-1611). Recently, Abgenix, Inc. (Fremont, Calif.) developed ABX-EGF for cancer therapy. ABX-EGF is a fully human anti-EGFR monoclonal antibody. (Yang, X. D., et al., Crit. Rev. Oncol./Hematol. 38 (2001) 17-23).

So far it was not possible to select antigen binding proteins, in particular antibodies, that specifically bind to the beta-hairpin of HER1 as this beta-hairpin of HER1 represents a hidden epitopes, which is not accessible in the equilibrium state of HER1 (see FIG. 1 and Lemmon, M A, Exp Cell Res. Feb. 15, 2009; 315(4): 638-648)).

SUMMARY OF THE INVENTION

Figure 2:
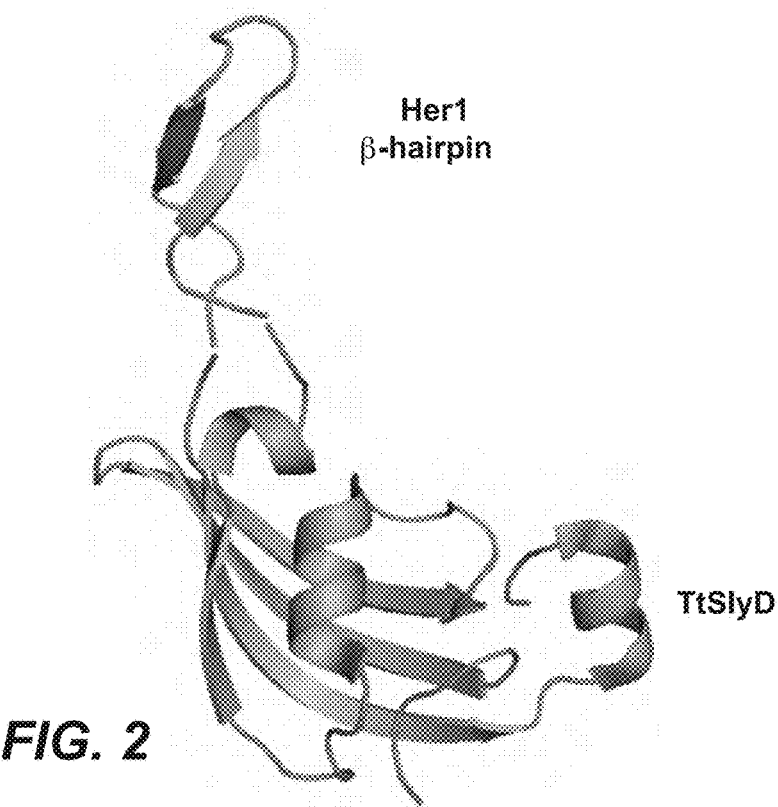

We now have found a method using the beta-hairpin of HER1 functionally presented in a 3-dimensional orientation within SlyD scaffolds (see e.g FIG. 2, and the polypeptides of SEQ ID NOs. 12 to 16, and 18) to obtain such antibodies.

The invention provides a method for selecting an antigen binding protein, in particular an antibody, that binds to human HER1, wherein the antigen binding protein, in particular the antibody, binds within an amino acid sequence of PPLMLYNPTTYQMDVNPEGK (SEQ ID NO:1) of human HER1;

wherein
a) at least one polypeptide selected from the group consisting of:

TtSlyDcas-HER1, SEQ ID NO: 12

TtSlyDcys-HER1, SEQ ID NO: 13

TtSlyD(GSG)-HER1, SEQ ID NO: 14

TtSlyD(CC)-HER1, SEQ ID NO: 15

TtSlyD(SS)-HER1, SEQ ID NO: 16
and

TgSlyDcys-HER1, SEQ ID NO: 18 which comprises the amino acid sequence of SEQ ID NO:1;
is used to select antigen binding proteins, in particular antibodies, which show binding to the at least one polypeptide under a),
and thereby selecting an antigen binding protein, in particular an antibody that binds within an amino acid sequence of PPLMLYNPTTYQMDVNPEGK (SEQ ID NO:1) of human HER1.

The invention provides an antigen binding protein, in particular an antibody, obtained by such selection method.

The invention provides an isolated an antigen binding protein, in particular an antibody, that binds to human HER1, wherein the antigen binding protein, in particular the antibody, binds within an amino acid sequence of PPLMLYNPTTYQMDVNPEGK (SEQ ID NO:1) of human HER1.

The invention further provides an isolated antigen binding protein that binds to human HER1, wherein the antigen binding protein binds to a polypeptide of TtSlyDcys-HER1; SEQ ID NO: 13
or TgSlyDcys-HER1. SEQ ID NO: 18

The invention further provides an isolated antigen binding protein that binds to human HER1, wherein the antigen binding protein binds to a polypeptide of TtSlyDcys-HER1. SEQ ID NO: 13

The invention further provides an isolated antigen binding protein that binds to human HER1, wherein the antigen binding protein binds to a polypeptide of TgSlyDcys-HER1. SEQ ID NO: 18

The invention further provides an isolated antigen binding protein that binds to human HER1,
wherein the antigen binding protein binds within an amino acid sequence of PPLMLYNPTTYQMDVNPEGK (SEQ ID NO:1) which is comprised in a polypeptide of SEQ ID NO: 13 TtSlyDcys-HER1.

The invention further provides an isolated antigen binding protein that binds to human HER1, wherein the antigen binding protein binds within an amino acid sequence of PPLMLYNPTTYQMDVNPEGK (SEQ ID NO:1) which is comprised in a polypeptide of SEQ ID NO: 18 TgSlyDcys-HER1.

The invention further provides an isolated antibody that binds to human HER1, wherein the antibody binds to a polypeptide of

```
                                    SEQ ID NO: 13
        TtSlyDcys-HER1;
    or
                                    SEQ ID NO: 18
        TgSlyDcys-HER1.
```

The invention further provides an isolated antibody that binds to human HER1, wherein the antibody binds to a polypeptide of

```
                                    SEQ ID NO: 13
        TtSlyDcys-HER1.
```

The invention further provides an isolated antibody that binds to human HER1, wherein the antibody binds to a polypeptide of

```
                                    SEQ ID NO: 18
        TgSlyDcys-HER1.
```

The invention further provides an isolated antibody that binds to human HER1, wherein the antibody binds within an amino acid sequence of PPLMLYNPTTYQMDVNPEGK (SEQ ID NO:1) which is comprised in a polypeptide of SEQ ID NO: 13 TtSlyDcys-HER1.

The invention further provides an isolated antibody that binds to human HER1, wherein the antibody binds within an amino acid sequence of PPLMLYNPTTYQMDVNPEGK (SEQ ID NO:1) which is comprised in a polypeptide of SEQ ID NO: 18 TgSlyDcys-HER1.

In one preferred embodiment the isolated antigen binding protein or antibody does not induce phosphorylation of HER1 in A549 cancer cells (ATCC CCL-185) in the absence of EGF.

In one preferred embodiment the isolated antigen binding protein or antibody is non-agonistic with respect to the phosphorylation of HER1 in A549 cancer cells (ATCC CCL-185) in the absence of EGF.

The invention provides an isolated antibody that binds to human HER1, wherein the antibody binds to the amino acid sequence SEQ ID NO:1 in activated HER1.

The invention provides an isolated antibody that binds to human HER1, wherein the antibody binds to the amino acid sequence SEQ ID NO:1 in activated HER1; and inhibits the homodimerisation of HER1 homodimers.

The invention provides an isolated antibody that binds to human HER1, wherein the antibody binds to the amino acid sequence SEQ ID NO:1 in activated HER1; and inhibits the heterodimerisation of HER1/HER2 heterodimers.

The invention provides an isolated antibody that binds to human HER1, wherein the antibody has on or more of the following properties:
a) binds to the amino acid sequence of SEQ ID NO:1; and/or
b) binds to the amino acid sequence SEQ ID NO:1 in activated HER1; and/or
c) binds within an amino acid sequence of PPLMLYNPTTYQMDVNPEGK (SEQ ID NO:1) which is comprised in a polypeptide selected from the group consisting of:

```
                                    SEQ ID NO: 12
        TtSlyDcas-HER1,
                                    SEQ ID NO: 13
        TtSlyDcys-HER1,
                                    SEQ ID NO: 14
        TtSlyD(GSG)-HER1,
                                    SEQ ID NO: 15
        TtSlyD(CC)-HER1,
                                    SEQ ID NO: 16
        TtSlyD(SS)-HER1,
    and
                                    SEQ ID NO: 18
        TgSlyDcys-HER1,
``` and/or
d) binds to the β-hairpin region of HER1; and/or
e) inhibits the heterodimerisation of HER1/HER2 heterodimers; and/or
f) has no crossreactivity with HER2, HER3 and/or HER4; and/or
g) the antibody binds to a polypeptide with a length of 15 amino acids comprising the amino acid sequence TYQMDVNPEG (SEQ ID NO:19); and/or
h) binds to a polypeptide consisting of TYQMDVNPEG (SEQ ID NO:19); and/or
i) the antibody binds to a polypeptide with a length of 15 amino acids comprising the amino acid sequence MLYNPTTYQ (SEQ ID NO:20); and/or
j) binds to a polypeptide consisting of MLYNPTTYQ (SEQ ID NO:20); and/or
k) does not induce phosphorylation of HER1 in A549 cancer cells (ATCC CCL-185) in the absence of EGF; and/or
l) is a non-agonistic antibody with respect to the phosphorylation of HER1 in the absence of EGF; and/or
m) shows more than 70 percent internalization of HER1 in the presence of EGF after 2 h after incubation with the antibody in a Western Blot assay with HER1 expressing A549 cells (ATCC CCL-185) and shows less than 55 percent internalization of HER1 in the absence of EGF after 2 h after incubation with the antibody in a Western Blot assay with HER1 expressing A549 cells.

In one embodiment such anti-HER1 antibody is a monoclonal antibody.

In one embodiment such anti-HER1 antibody is a human, humanized, or chimeric antibody.

In one embodiment such anti-HER1 antibody is an antibody fragment that binds human HER1.
a) all three heavy chain HVRs and all three light chain HVRs of the deposited antibody MAK <HER1-DIB> M-50.097.14 (DSM ACC3240);
b) all three heavy chain HVRs and all three light chain HVRs of the deposited antibody MAK <HER1-DIB> M-50.110.23 (DSM ACC3241);
c) all three heavy chain HVRs and all three light chain HVRs of the deposited antibody MAK <HER1-DIB> M-37.058.09 (DSM ACC3238);

d) all three heavy chain HVRs and all three light chain HVRs of the deposited antibody MAK <HER1-DIB> M-37.186.15 (DSM ACC3239).

One embodiment of the invention is humanized anti-HER1 antibody which comprises
a) all three heavy chain HVRs and all three light chain HVRs of the deposited antibody MAK <HER1-DIB> M-50.097.14 (DSM ACC3240);
b) all three heavy chain HVRs and all three light chain HVRs of the deposited antibody MAK <HER1-DIB> M-50.110.23 (DSM ACC3241);
c) all three heavy chain HVRs and all three light chain HVRs of the deposited antibody MAK <HER1-DIB> M-37.058.09 (DSM ACC3238);
d) all three heavy chain HVRs and all three light chain HVRs of the deposited antibody MAK <HER1-DIB> M-37.186.15 (DSM ACC3239).

In one embodiment such anti-HER1 antibody is a full length IgG1 antibody or IgG4 antibody.

In one embodiment such anti-HER1 antibody is a Fab fragment.

The invention further provides an isolated nucleic acid such anti-HER1 antibody.

The invention further provides a host cell comprising such nucleic acid.

The invention further provides a method of producing an antibody comprising culturing such host cell so that the antibody is produced.

In on embodiment such method further comprises recovering the antibody from the host cell.

The invention further provides an immunoconjugate comprising such anti-HER1 antibody and a cytotoxic agent.

The invention further provides a pharmaceutical formulation comprising such anti-HER1 antibody and a pharmaceutically acceptable carrier.

The invention further provides the anti-HER1 antibody described herein for use as a medicament. The invention further provides the anti-HER1 antibody described herein, or the immunoconjugate comprising the anti-HER1 antibody and a cytotoxic agent, for use in treating cancer. The invention further provides the anti-HER1 antibody described herein for use in inhibition of HER family dimerization (HER1 homo- or heterodimerization, e.g. HER1 homodimerization, or HER1/HER2 heterodimerization)

Use of such anti-HER1 antibody, or an immunoconjugate comprising the anti-HER1 antibody and a cytotoxic agent, in the manufacture of a medicament. Such use wherein the medicament is for treatment of cancer. Such use wherein the medicament is for the inhibition of HER1 homo- or heterodimerization.

The invention further provides a method of treating an individual having cancer comprising administering to the individual an effective amount of the anti-HER1 antibody described herein, or an immunoconjugate comprising the anti-HER1 antibody and a cytotoxic agent.

The invention further provides a method of inducing apoptosis in a cancer cell in an individual suffering from cancer comprising administering to the individual an effective amount of an immunoconjugate comprising the anti-HER1 antibody described herein and a cytotoxic agent, thereby inducing apoptosis in a cancer cell in the individual.

One embodiment of the invention is a polypeptide selected from the group consisting of:

i) TtSlyDcas-HER1, SEQ ID NO: 12 ii) TtSlyDcys-HER1, SEQ ID NO: 13 iii) TtSlyD(GSG)-HER1, SEQ ID NO: 14 iv) TtSlyD(CC)-HER1, SEQ ID NO: 15 v) TtSlyD(SS)-HER1, SEQ ID NO: 16 and vi) TgSlyDcys-HER1, SEQ ID NO: 18 which polypeptide comprises the amino acid sequence of SEQ ID NO:1.

The invention further provides the use of one of such polypeptides selected from the group consisting of:

i) TtSlyDcas-HER1, SEQ ID NO: 12 ii) TtSlyDcys-HER1, SEQ ID NO: 13 iii) TtSlyD(GSG)-HER1, SEQ ID NO: 14 iv) TtSlyD(CC)-HER1, SEQ ID NO: 15 v) TtSlyD(SS)-HER1, SEQ ID NO: 16 and vi) TgSlyDcys-HER1, SEQ ID NO: 18 for eliciting an immune response against SEQ ID NO:1 in an experimental animal.

The invention further provides a method for producing an antibody specifically binding to the β-hairpin of HER1 with the amino acid sequence of SEQ ID NO:1 comprising the following steps:
a) administering to an experimental animal a polypeptide selected from the group consisting of:

i) TtSlyDcas-HER1, SEQ ID NO: 12 ii) TtSlyDcys-HER1, SEQ ID NO: 13 iii) TtSlyD(GSG)-HER1, SEQ ID NO: 14

-continued

```
iv)
                                    SEQ ID NO: 15
TtSlyD(CC)-HER1, v)
                                    SEQ ID NO: 16
TtSlyD(SS)-HER1,
and vi)
                                    SEQ ID NO: 18
TgSlyDcys-HER1,
``` for at least one time, whereby the polypeptide comprises the β-hairpin of HER1 with the amino acid sequence of SEQ ID NO:1, b) recovering from the experimental animal three to ten days after the last administration of the polypeptide B-cells that produce the antibody specifically binding to the β-hairpin of HER1 with the amino acid sequence of SEQ ID NO:1, and c) cultivating a cell comprising a nucleic acid encoding the antibody specifically binding to the β-hairpin of HER1 with the amino acid sequence of SEQ ID NO:1 and recovering the antibody from the cell or the cultivation medium and thereby producing an antibody specifically binding to a target antigen.

The invention further provides the use of a polypeptide selected from the group consisting of:

```
i)
                                    SEQ ID NO: 12
TtSlyDcas-HER1, ii)
                                    SEQ ID NO: 13
TtSlyDcys-HER1, iii)
                                    SEQ ID NO: 14
TtSlyD(GSG)-HER1, iv)
                                    SEQ ID NO: 15
TtSlyD(CC)-HER1, v)
                                    SEQ ID NO: 16
TtSlyD(SS)-HER1,
and vi)
                                    SEQ ID NO: 18
TgSlyDcys-HER1,
``` for epitope mapping, whereby the polypeptide comprises the epitope in the β-hairpin of HER1 with the amino acid sequence of SEQ ID NO:1.

Using the beta-hairpin of HER1 functionally presented in a 3-dimensional orientation within SlyD scaffolds (see e.g FIG. 2, and the polypeptides of SEQ ID NOs. 12 to 16, and 18) the anti-HER1 antigen binding proteins, in particular antibodies, described herein binding to this beta-hairpin could be selected. It was found that the antigen binding proteins, in particular antibodies, according to the invention have highly valuable properties such as the binding to the activated form of HER1, so they show a clearly stronger HER1 internalization in the presence than in the absence of EGF. They are non-agonistic antibodies with respect to the phosphorylation of HER1 (they do not induce HER1 phosphorylation in HER1 expressing cancer cells) in absence of EGF (and therefore are likely to show less side effects during HER1 antibody therapy like e.g. skin rash).

BRIEF DESCRIPTION OF THE FIGURES

FIG. 1 Schematic overview of "closed" and "open" HER1 conformation and the influence of the EGF ligand on the conformation change.

FIG. 2 3D-structure of the beta-hairpin of HER1 functionally presented in a 3-dimensional orientation within a SlyD scaffold of *Thermus thermophiles.*

FIG. 3 SDS-PAGE analysis of Ni-NTA purification of TtSlyD-cas-Her1. E show the purified fractions. SN: *E. coli* lysate supernatant before purification.

FIG. 4 SEC elution profile of a Ni-NTA purified fraction of *Thermus thermophilus* TtSlyD-cas-Her1.

FIG. 5 Testing of specificity and reactivity in IHC the selected antibodies M-31-22, M-47-13, M-50-14 (deposited MAK <HER1-DIB> M-50.097.14) and M-50-23 (deposited MAK <HER1-DIB> M-50.110.23) which bind to the β-hairpin of human HER1. As shown all antibodies specific for the detection of HER1 and shows no cross reactivity with the other members of the HER family (HER2, HER3, and HER4).

FIG. 6 Strategy of the epitope mapping and alanine-scan approach. The peptide hairpin sequences (peptide hairpin) of HER1 (EGFR) ECD, Her-2 ECD, Her-3 ECD and Her-4 ECD including their structural embeddings (structural) were investigated. Cysteins were replaced by serines.

FIG. 7 CelluSpots™ Synthesis and Epitope Mapping of epitopes of HER1 antibodies M-31-22, M-47-13, M-50-14 (deposited MAK <HER1-DIB> M-50.097.14) and M-50-23 (deposited MAK <HER1-DIB> M-50.110.23). M-47-13 binds to HER1 ECD binding epitope TYQMDVNPEG (SEQ ID NO:19). M-50-14 (deposited MAK <HER1-DIB> M-50.097.14) and M-50-23 (deposited MAK <HER1-DIB> M-50.110.23) bind to HER1 ECD binding epitope MLYNPTTYQ (SEQ ID NO:20)—the amino acids which are contributing most to the binding of are underlined/bold.

FIGS. 8A and 8B 8A (A549 cells) and 8B (A431 cells, strong HER1 expression with slight constitutively activated/ phosphorylated HER1). Left lane shows HER1 detection, right lane the phosphorylated HER1 detection in the absence or presence of EGF In both cancer cell lines the anti-HER1 β-hairpin antibodies HER1 dib1=M-50-14 (=deposited MAK <HER1-DIB> M-50.097.14), HER1 dib2=M-50-23 (=deposited MAK <HER1-DIB> M-50.110.23) and HER1 dib3=M-47-15 acted as non-agonistic antibody with respect to the phosphorylation of HER1 in the absence of EGF (no induction the phosphorylation of HER1, -EGF lane), while other HER1 antibodies like cetuximab, GA201, described e.g. in WO 2006/082515), or ABT806 (mAb806, described e.g in US2011/0076232) strongly induced phosphorylation (compared to medium without antibody).

FIG. 9 Binding of anti-HER1 β-hairpin antibodies to and internalization of anti-HER1 β-hairpin antibodies was analyzed in Western Blot using the HER1 expressing cancer cell line A549. Left side shows time dependent HER1 detection in the absence of EGF, right side shows time dependent HER1 detection in the presence of EGF. Antibody M-50-14 shows a clearly stronger HER1 internalization in the presence than in the absence of EGF. (more than 70 percent internalization of HER1 in the presence of EGF after 2 h after incubation with the antibody in a Western Blot assay with HER1 expressing A549 cells and less than 55 percent internalization of HER1 in the absence of EGF after 2 h after incubation with the antibody in a Western Blot assay with HER1 expressing A549 cells).

Figure 10:
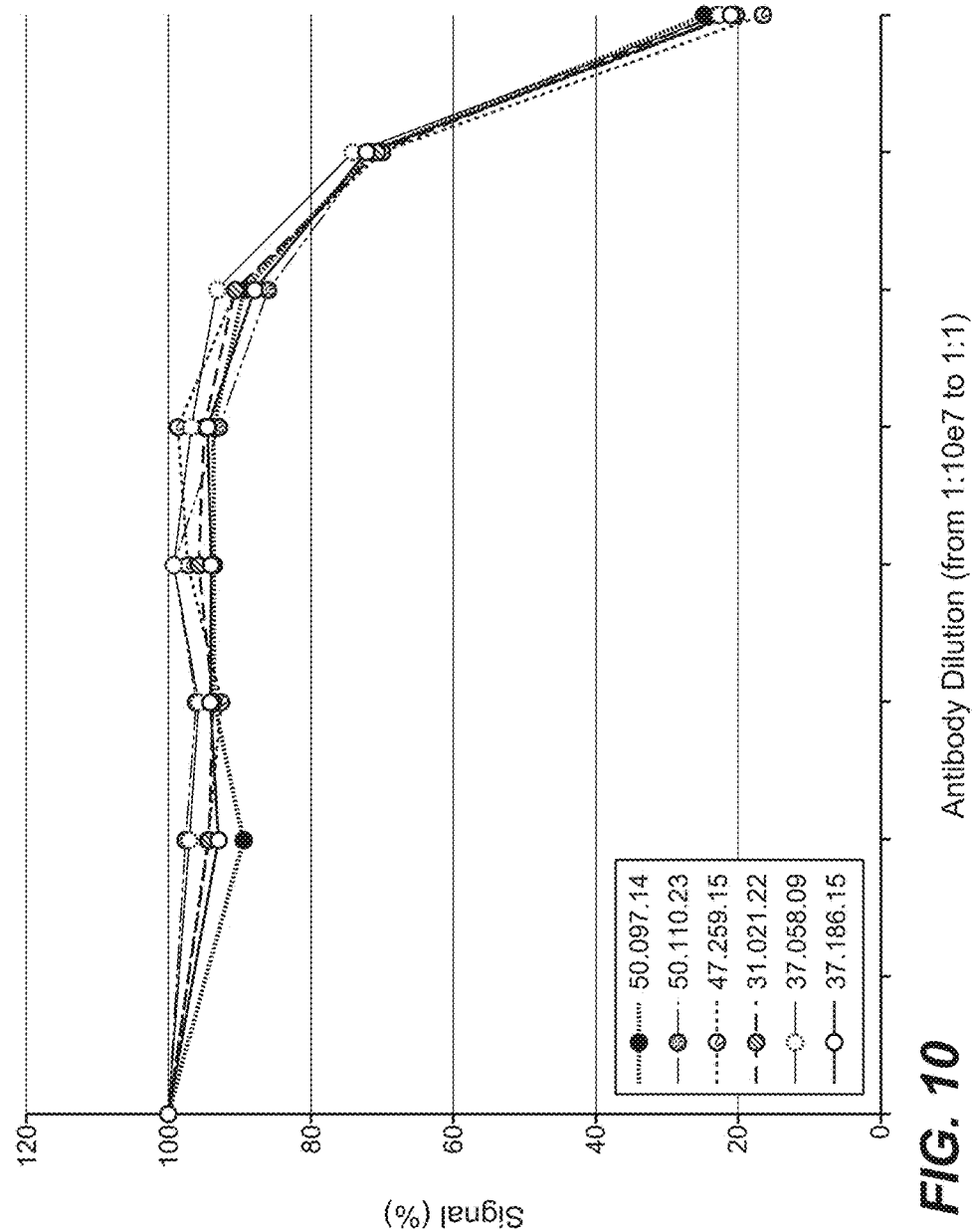

FIG. 10 Binding of different antibodies of the invention to HER1-ECD in the presence of EGF.

DETAILED DESCRIPTION OF EMBODIMENTS OF THE INVENTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "antigen binding protein" as used herein refers to an antibody as described herein or to a scaffold antigen binding protein. In one preferred embodiment the antigen binding protein is an antibody as described herein. Scaffold antigen binding proteins are known in the art, for example, fibronectin and designed ankyrin-repeat proteins (DARPins) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discov Today 13: 695-701 (2008), both of which are incorporated herein by reference in their entirety. B. Criteria for Selecting Parent Variable Domains and Receptors for antigen binding proteins of the invention. In one embodiment a scaffold antigen binding protein is selected from the group consisting of CTLA-4 (Evibody); lipocalin; Protein A derived molecules such as Z-domain of Protein A (Affibody, SpA), A-domain (Avimer/Maxibody); Heat shock proteins such as GroEI and GroES; transferrin (trans-body); ankyrin repeat protein (DARPin); peptide aptamer; C-type lectin domain (Tetranectin); human .gamma.-crystallin and human ubiquitin (affilins); PDZ domains; scorpion toxinkunitz type domains of human protease inhibitors; and fibronectin (adnectin); which has been subjected to protein engineering in order to obtain binding to a ligand other than the natural ligand.

CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies. For further details see Journal of Immunological Methods 248 (1-2), 31-45 (2001).

Lipocalins are a family of extracellular proteins which transport small hydrophobic molecules such as steroids, bilins, retinoids and lipids. They have a rigid .beta.-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633.

An affibody is a scaffold derived from Protein A of *Staphylococcus aureus* which can be engineered to bind to antigen. The domain consists of a three-helical bundle of approximately 58 amino acids. Libraries have been generated by randomisation of surface residues. For further details see Protein Eng. Des. Sel. 17, 455-462 (2004) and EP1641818A1Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007).

A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999).

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two .alpha.-helices and a .beta.-turn. They can be engineered to bind different target antigens by randomising residues in the first .alpha.-helix and a .beta.-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

Fibronectin is a scaffold which can be engineered to bind to antigen. Adnectins consists of a backbone of the natural amino acid sequence of the 10th domain of the 15 repeating units of human fibronectin type III (FN3). Three loops at one end of the .beta.-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1.

Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005).

Microbodies are derived from naturally occurring microproteins of 25-50 amino acids in length which contain 3-4 cysteine bridges—examples of microproteins include KalataBI and conotoxin and knottins. The microproteins have a loop which can be engineered to include up to 25 amino acids without affecting the overall fold of the microprotein. For further details of engineered knottin domains, see WO2008098796.

Other antigen binding proteins include proteins which have been used as a scaffold to engineer different target antigen binding properties include human .gamma.-crystallin and human ubiquitin (affilins), kunitz type domains of human protease inhibitors, PDZ-domains of the Ras-binding protein AF-6, scorpion toxins (charybdotoxin), C-type lectin domain (tetranectins) are reviewed in Chapter 7—Non-Antibody Scaffolds from Handbook of Therapeutic Antibodies (2007, edited by Stefan Dubel) and Protein Science 15:14-27 (2006). Epitope binding domains of the present invention could be derived from any of these alternative protein domains.

The terms "anti-HER1 antigen binding protein", "an antigen binding protein that binds to (human) HER1" and "an antigen binding protein that binds specifically to human HER1" and refer to an antigen binding protein that is capable of binding HER1 with sufficient affinity such that the antigen binding protein is useful as a diagnostic and/or therapeutic agent in targeting HER1. In one embodiment, the extent of binding of an anti-HER1 antigen binding protein to an unrelated, non-HER1 protein is less than about 10% of the binding of the antigen binding protein to HER1 as measured, e.g., by a Surface Plasmon Resonance assay (e.g. BIACORE). In certain embodiments, an antigen binding protein that binds to human HER1 has a KD value of the binding affinity for binding to human HER1 of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M). In one preferred embodiment the respective KD value of the binding affinities is determined in a Surface Plasmon Resonance assay using the wildtype Extracellular domain (ECD) of human HER1 (HER1-ECD) for the HER1 binding affinity.

The terms "anti-HER1 antibody", "an antibody that binds to (human) HER1" and "an antibody that binds specifically to human HER1" and refer to an antibody that is capable of binding HER1 with sufficient affinity such that the antibody is useful as a diagnostic and/or therapeutic agent in targeting HER1. In one embodiment, the extent of binding of an anti-HER1 antibody to an unrelated, non-HER1 protein is less than about 10% of the binding of the antibody to HER1 as measured, e.g., by a Surface Plasmon Resonance assay (e.g. BIACORE). In certain embodiments, an antibody that binds to human HER1 has a KD value of the binding affinity for binding to human HER1 of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M). In one preferred embodiment the respective KD value of the binding affinities is determined in a Surface Plasmon Resonance assay using the wildtype Extracellular domain (ECD) of human HER1 (HER1-ECD) for the HER1 binding affinity.

The term "anti-HER1 antigen binding protein or anti-HER1 antibody that binds to the amino acid sequence SEQ ID NO:1 in activated HER1" as used herein refers to an anti-HER1 antigen binding protein or anti-HER1 antibody that binds to the amino acid sequence SEQ ID NO:1 comprised in the human HER1-ECD.

In one preferred embodiment the term "anti-HER1 antigen binding protein or anti-HER1 antibody that binds to the amino acid sequence SEQ ID NO:1" as used herein refers to an anti-HER1 antigen binding protein or anti-HER1 antibody that binds to the amino acid sequence SEQ ID NO:1 comprised in the polypeptide of SEQ ID NO: 13 (TtSlyD-cys-HER1).

In one embodiment the term "anti-HER1 antigen binding protein or anti-HER1 antibody that binds to the amino acid sequence SEQ ID NO:1 in activated HER1" refers to an anti-HER1 antigen binding protein or anti-HER1 antibody that binds to the amino acid sequence SEQ ID NO:1 comprised in the polypeptide of SEQ ID NO: 13 (TtSlyD-cys-HER1).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "antibody (or antigen binding protein) that has/shows crossreactivity to (or alternatively that crossreacts with) (human) HER2, HER3 and/or HER4, when it does not crossreacts with Extracellular domain (ECD) of) human HER2, HER3 and/or HER4, i.e. when the binding signal (in Relative Units (RU)) measured in a Surface Plasmon Resonance assay is below three times the background signal (noise) (e.g at 25° C. with immobilized (for example captured) antibody to which the human HER2, HER3 and/or HER4-ECD as antigen is injected as soluble analyte).

The term "cancer" as used herein may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers. In one preferred embodiment such cancer is a breast cancer, ovarian cancer, cervical cancer, lung cancer or prostate cancer. In one preferred embodiment such cancers are further characterized by HER1 expression or overexpression. One further embodiment the invention are the anti-HER1 antibodies of the present invention for use in the simultaneous treatment of primary tumors and new metastases.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ respectively.

The term "cytotoxic agent" as used herein refers to a substance that inhibits or prevents a cellular function and/or causes cell death or destruction. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below. In one preferred embodiment the "cytotoxic agent" is *Pseudomonas* exotoxin A or variants thereof. In one preferred embodiment the "cytotoxic agent" is amatoxin or a variants thereof.

The term "deposited antibody" as used herein refers to the antibody produced by the respective deposited hybridoma cells identified by the designation and deposition number. See also Deposit of biological material below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized variant" of an antibody, e.g., a non-human antibody, refers to an antibody that has undergone humanization. In one preferred embodiment, a murine HVR is grafted into the framework region of a human antibody to prepare the "humanized antibody." See e.g. Riechmann, L., et al., Nature 332 (1988) 323-327; and Neuberger, M. S., et al., Nature 314 (1985) 268-270. The murine variable region amino acid sequence is aligned to a collection of human germline antibody V-genes, and sorted according to sequence identity and homology. The acceptor sequence is selected based on high overall sequence homology and optionally also the presence of the right canonical residues already in the acceptor sequence (see Poul, M-A. and Lefranc, M-P., in "Ingénierie des anticorps banques combinatores" ed. by Lefranc, M-P. and Lefranc, G., Les Editions INSERM, 1997). The germline V-gene encodes only the region up to the beginning of HVR3 for the heavy chain, and till the middle of HVR3 of the light chain. Therefore, the genes of the germline V-genes are not aligned over the whole V-domain. The humanized construct comprises the human frameworks 1 to 3, the murine HVRs, and the human framework 4 sequence derived from the human JK4, and the JH4 sequences for light and heavy chain, respectively. Before selecting one particular acceptor sequence, the so-called canonical loop structures of the donor antibody can be determined (see Morea, V., et al., Methods, Vol 20, Issue 3 (2000) 267-279). These canonical loop structures are determined by the type of residues present at the so-called canonical positions. These positions lie (partially) outside of the HVR regions, and should be kept functionally equivalent in the final construct in order to retain the HVR conformation of the parental (donor) antibody. In WO 2004/006955 a method for humanizing antibodies is reported that comprises the steps of identifying the canonical HVR structure types of the HVRs in a non-human mature antibody; obtaining a library of peptide sequence for human antibody variable regions; determining the canonical HVR structure types of the variable regions in the library; and selecting the human sequences in which the canonical HVR structure is the same as the non-human antibody canonical HVR structure type at corresponding locations within the non-human and human variable regions. Summarizing, the potential acceptor sequence is selected based on high overall homology and optionally in addition the presence of the right canonical residues already in the acceptor sequence. In some cases simple HVR grafting only result in partial retention of the binding specificity of the non-human antibody. It has been found that at least some specific non-human framework residues are required for reconstituting the binding specificity and have also to be grafted into the human framework, i.e. so called "back mutations" have to be made in addition to the introduction of the non-human HVRs (see e.g. Queen et al., Proc. Natl. Acad. Sci. USA 86 (1989) 10,029-10,033; Co et al., Nature 351 (1991) 501-502). These specific framework amino acid residues participate in FR-HVR interactions and stabilized the conformation (loop) of the HVRs (see e.g. Kabat et al., J. Immunol. 147 (1991) 1709). In some cases also forward-mutations are introduced in order to adopt more closely the human germline sequence. Thus "humanized variant of an antibody according to the invention" (which is e.g. of mouse origin) refers to an antibody, which is based on the mouse antibody sequences in which the VH and VL are humanized by above described standard techniques (including HVR grafting and optionally subsequent mutagenesis of certain amino acids in the framework region and the HVR-H1, HVR-H2, HVR-L1 or HVR-L2, whereas HVR-H3 and HVR-L3 remain unmodified).

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

Preferably the HVRs refer to CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, Md. (1991)), i.e. the HVRs are determined according to Kabat.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-HER1 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "Mab" refers to monoclonal antibodies, whereas the term "hMab" refers to humanized variants of such monoclonal antibodies.

A "naked antibody" refers to an antibody that is not conjugated to a heterologous moiety (e.g., a cytotoxic moiety) or radiolabel. The naked antibody may be present in a pharmaceutical formulation. (Include if Prior art has immunoconjugates).

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject., A pharmaceutically acceptable carrier includes, but is not limited to, a buffer, excipient, stabilizer, or preservative.

The term "HER1," as used herein, refers to any native HER1 from any vertebrate source, including mammals such as primates (e.g. humans) and rodents (e.g., mice and rats), unless otherwise indicated. The term encompasses "full-length," unprocessed HER1 as well as any form of HER1 that results from processing in the cell. The term also encompasses naturally occurring variants of HER1, e.g., splice variants or allelic variants. The amino acid sequence of an exemplary human HER1 is shown in SEQ ID NO:2. "Human HER1 ((also known as epidermal growth factor receptor EGFR or Erb-B1) is a 170 kDa transmembrane receptor encoded by the c-erbB proto-oncogene, and exhibits intrinsic tyrosine kinase activity (Modjtahedi, H., et al., Br. J. Cancer 73 (1996) 228-235; Herbst, R. S., and Shin, D. M., Cancer 94 (2002) 1593-1611). SwissProt database entry P00533 provides the sequence of HER1 (SEQ ID NO: 2). There are also isoforms and variants of HER1 (e.g., alternative RNA transcripts, truncated versions, polymorphisms, etc.) including but not limited to those identified by Swissprot database entry numbers P00533-1, P00533-2, P00533-3, and P00533-4. HER1 is known to bind ligands including α), epidermal growth factor (EGF) (SEQ ID NO: 4), transforming growth factor-α (TGF), amphiregulin, heparin-binding EGF (hb-EGF), betacellulin, and epiregulin (Herbst, R. S., and Shin, D. M., Cancer 94 (2002) 1593-1611; Mendelsohn, J., and Baselga, J., Oncogene 19 (2000) 6550-6565). HER1 regulates numerous cellular processes via tyrosine-kinase mediated signal transduction pathways, including, but not limited to, activation of signal transduction pathways that control cell proliferation, differentiation, cell survival, apoptosis, angiogenesis, mitogenesis, and metastasis (Atalay, G., et al., Ann. Oncology 14 (2003) 1346-1363; Tsao, A. S., and Herbst, R. S., Signal 4 (2003)

4-9; Herbst, R. S., and Shin, D. M., Cancer 94 (2002) 1593-1611; Modjtahedi, H., et al., Br. J. Cancer 73 (1996) 228-235). The term "epidermal growth factor" (EGF) as used herein refers to human epidermal growth factor (EGF, hEGF) (SEQ ID NO: 4).

Interestingly in its equilibrium state, the HER1 receptors exists in its "closed confirmation", which does mean, the dimerization HER1 beta-hairpin motive is tethered via non-covalent interactions to the HER1 ECD domain IV (see FIG. 1 and Lemmon, M A, "Ligand-induced ErbB receptor dimerization" Exp Cell Res. Feb. 15, 2009; 315(4): 638-648, the whole article). It is supposed, that the "closed" HER1 conformation can be opened via the binding of the ligand EGF (SEQ ID NO: 4) at a specific HER1 EGF binding site. This takes place at the HER1 interface formed by the HER1 ECD domains I and domain III. By this interaction it is believed, that the HER1 receptor is activated and transferred into its "open conformation" (see FIG. 1). In this open conformation homodimerization with another HER1 molecule or heterodimerization with another member of the HER family and signal induction (Lemmon, M A, Exp Cell Res. Feb. 15, 2009; 315(4): 638-648).

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Compositions and Methods

In one aspect, the invention is based, in part, on the finding that using the beta-hairpins of HER1 functionally presented in a 3-dimensional orientation within SlyD scaffolds (see e.g FIG. 2, and the polypeptides of SEQ ID NOs. 12 to 16, and 18) it was possible to select antibodies which are specific for the beta-hairpin of HER1 (and do not crossreact of HER2, HER3 and/or HER4).

In certain embodiments, the invention provides an antibody that binds to human HER1, wherein the antibody binds within an amino acid sequence of PPLMLYNPTTYQMDVNPEGK (SEQ ID NO:1) of human HER1.

Antibodies of the invention are useful, e.g., for the diagnosis or treatment of cancer.

A. Exemplary Anti-HER1 Antigen Binding Proteins and Antibodies

The invention provides an isolated antigen binding protein that binds to human HER1, wherein the antigen binding protein binds to a polypeptide selected from the group consisting of:

TtSlyDcas-HER1, SEQ ID NO: 12

TtSlyDcys-HER1, SEQ ID NO: 13

TtSlyD(GSG)-HER1, SEQ ID NO: 14

TtSlyD(CC)-HER1, SEQ ID NO: 15

TtSlyD(SS)-HER1, SEQ ID NO: 16
and

TgSlyDcys-HER1. SEQ ID NO: 18

The invention further provides an isolated antigen binding protein that binds to human HER1, wherein the antigen binding protein binds within an amino acid sequence of PPLMLYNPTTYQMDVNPEGK (SEQ ID NO:1) which is comprised in a polypeptide selected from the group consisting of:

TtSlyDcas-HER1, SEQ ID NO: 12

TtSlyDcys-HER1, SEQ ID NO: 13

TtSlyD(GSG)-HER1, SEQ ID NO: 14

TtSlyD(CC)-HER1, SEQ ID NO: 15

TtSlyD(SS)-HER1, SEQ ID NO: 16
and

TgSlyDcys-HER1. SEQ ID NO: 18

The invention further provides an isolated antigen binding protein that binds to human HER1,
a) wherein the antigen binding protein binds to a polypeptide of TtSlyDcys-Her1. SEQ ID NO: 13

The invention further provides an isolated antigen binding protein that binds to human HER1, wherein the antigen binding protein binds to a polypeptide of SEQ ID NO: 13
TtSlyDcys-Her1 with an at least 50 times higher ELISA signal (in one preferred embodiment with an at least 100 times higher ELISA signal; in another preferred embodiment with an at least 500 times higher ELISA signal) when compared to the binding to a polypeptide of SEQ ID NO: 11
TtSlyDcas in an ELISA assay, wherein TtSlyDcys-HER1 and TtSlyDcas were immobilized at a concentration of 0.5 µg/ml.

Preferably the ELISA signal was detected with a Horse radish peroxidase (HRP)-labeled F(ab')₂ goat anti-mouse Fcγ and 2,2'-Azino-di-[3-ethylbenzthiazoline sulfonate (6)] diammonium salt (ABTS) was used as a HRP-substrate.

The invention further provides an isolated antigen binding protein that binds to human HER1,
a) wherein the antigen binding protein binds within an amino acid sequence of PPLMLYNPTTYQMDVNPEGK (SEQ ID NO:1) which is comprised in a polypeptide of SEQ ID NO: 13 (TtSlyDcys-Her1).

The invention provides an isolated antibody that binds to human HER1,
a) wherein the antibody binds to a polypeptide selected from the group consisting of:

SEQ ID NO: 12
TtSlyDcas-HER1,

SEQ ID NO: 13
TtSlyDcys-HER1,

SEQ ID NO: 14
TtSlyD(GSG)-HER1,

SEQ ID NO: 15
TtSlyD(CC)-HER1,

SEQ ID NO: 16
TtSlyD(SS)-HER1,
and

SEQ ID NO: 18
TgSlyDcys-HER1.

The invention further provides an isolated antibody that binds to human HER1,
a) wherein the antibody binds within an amino acid sequence of PPLMLYNPTTYQMDVNPEGK (SEQ ID NO:1) which is comprised in a polypeptide selected from the group consisting of:

SEQ ID NO: 12
TtSlyDcas-HER1,

SEQ ID NO: 13
TtSlyDcys-HER1,

SEQ ID NO: 14
TtSlyD(GSG)-HER1,

SEQ ID NO: 15
TtSlyD(CC)-HER1,

SEQ ID NO: 16
TtSlyD(SS)-HER1,
and

SEQ ID NO: 18
TgSlyDcys-HER1.

The invention further provides an isolated antibody that binds to human HER1,
a) wherein the antibody binds to a polypeptide of SEQ ID NO: 13
TtSlyDcys-Her1.

The invention further provides an isolated antibody that binds to human HER1,
a) wherein the antibody binds within an amino acid sequence of PPLMLYNPTTYQMDVNPEGK (SEQ ID NO:1) which is comprised in a polypeptide of SEQ ID NO: 13 (TtSlyDcys-Her1).

In one aspect, the invention provides an isolated antibody that binds to human HER1, wherein the antibody binds within an amino acid sequence of PPLMLYNPTTYQMDVNPEGK (SEQ ID NO:1) of human HER1.

In certain embodiments, the invention provides an isolated antibody that binds to human HER1, wherein the antibody has one or more of the following properties (also each combination of each single property is contemplated herein):
a) the antibody binds to the amino acid sequence of SEQ ID NO:1; and/or
b) the antibody binds to the amino acid sequence SEQ ID NO:1 in activated HER1; and/or
c) the antibody binds within an amino acid sequence of PPLMLYNPTTYQMDVNPEGK (SEQ ID NO:1) which is comprised in a polypeptide selected from the group consisting of:

SEQ ID NO: 12
TtSlyDcas-HER1,

SEQ ID NO: 13
TtSlyDcys-HER1,

SEQ ID NO: 14
TtSlyD(GSG)-HER1,

SEQ ID NO: 15
TtSlyD(CC)-HER1,

SEQ ID NO: 16
TtSlyD(SS)-HER1,
and

SEQ ID NO: 18
TgSlyDcys-HER1, and/or
d) binds to the β-hairpin region of HER1; and/or
e) inhibits the heterodimerisation of HER1/HER2 heterodimers; and/or
f) has no crossreactivity with HER2, HER3 and/or HER4; and/or
g) the antibody binds to a polypeptide with a length of 15 amino acids comprising the amino acid sequence TYQMDVNPEG (SEQ ID NO:19); and/or
h) binds to a polypeptide consisting of TYQMDVNPEG (SEQ ID NO:19); and/or
i) the antibody binds to a polypeptide with a length of 15 amino acids comprising the amino acid sequence MLYNPTTYQ (SEQ ID NO:20); and/or j) binds to a polypeptide consisting of MLYNPTTYQ (SEQ ID NO:20); and/or
k) does not induce phosphorylation of HER1 in A549 cancer cells in the absence of EGF (see Example 6); and/or
l) is a non-agonistic antibody with respect to the phosphorylation of HER1 in the absence of EGF (see Example 6); and/or
m) shows more than 70 percent internalization of HER1 in the presence of EGF after 2 h after incubation with the antibody in a Western Blot assay with HER1 expressing A549 cells and shows less than 55 percent internalization of HER1 in the absence of EGF after 2 h after incubation with the antibody in a Western Blot assay with HER1 expressing A549 cells (see Example 5).

In certain embodiments, the invention provides an isolated antibody that binds to human HER1, wherein the antibody the antibody binds to a polypeptide with a length of 15 amino acids comprising the amino acid sequence MLYNPTTYQ (SEQ ID NO:20).

In certain embodiments, the invention provides an isolated antibody that binds to human HER1, wherein the antibody the antibody binds to a polypeptide with a length of 15 amino acids comprising the amino acid sequence TYQMDVNPEG (SEQ ID NO:19).

In one aspect, the invention provides an anti-HER1 antibody comprising all six HVRs selected from the group consisting of:
i) deposited antibody MAK <HER1-DIB> M-50.097.14 (DSM ACC3240);
ii) deposited antibody MAK <HER1-DIB> M-50.110.23 (DSM ACC3241);
iii) deposited antibody MAK <HER1-DIB> M-37.058.09 (DSM ACC3238); and
iv) deposited antibody MAK <HER1-DIB> M-37.186.15 (DSM ACC3239).

Preferably the HVRs are determined according to Kabat.
In one preferred embodiment the invention provides an anti-HER1 antibody comprising all six HVRs selected from the group consisting of:
i) deposited antibody MAK <HER1-DIB> M-50.097.14 (DSM ACC3240); and
ii) deposited antibody MAK <HER1-DIB> M-50.110.23 (DSM ACC3241).

Preferably the HVRs are determined according to Kabat.
In one aspect, the invention provides an anti-HER1 antibody comprising all six HVRs selected from the group consisting of:
i) deposited antibody MAK <HER1-DIB> M-50.097.14 (DSM ACC3240);
ii) deposited antibody MAK <HER1-DIB> M-50.110.23 (DSM ACC3241);
iii) deposited antibody MAK <HER1-DIB> M-37.058.09 (DSM ACC3238); and
iv) deposited antibody MAK <HER1-DIB> M-37.186.15 (DSM ACC3239);
wherein the antibody has one or more of the following properties:
a) the antibody binds to the amino acid sequence of SEQ ID NO:1; and/or
b) the antibody binds to the amino acid sequence SEQ ID NO:1 in activated HER1; and/or
c) the antibody binds within an amino acid sequence of PPLMLYNPTTYQMDVNPEGK (SEQ ID NO:1) which is comprised in a polypeptide selected from the group consisting of:

TtSlyDcas-HER1, SEQ ID NO: 12
TtSlyDcys-HER1, SEQ ID NO: 13
TtSlyD(GSG)-HER1, SEQ ID NO: 14
TtSlyD(CC)-HER1, SEQ ID NO: 15
TtSlyD(SS)-HER1, and SEQ ID NO: 16
TgSlyDcys-HER1, SEQ ID NO: 18 and/or
d) binds to the β-hairpin region of HER1; and/or
e) inhibits the heterodimerisation of HER1/HER2 heterodimers; and/or
f) has no crossreactivity with HER2, HER3 and/or HER4; and/or
g) the antibody binds to a polypeptide with a length of 15 amino acids comprising the amino acid sequence TYQMDVNPEG (SEQ ID NO:19); and/or
h) binds to a polypeptide consisting of TYQMDVNPEG (SEQ ID NO:19); and/or
i) the antibody binds to a polypeptide with a length of 15 amino acids comprising the amino acid sequence MLYNPTTYQ (SEQ ID NO:20); and/or
j) binds to a polypeptide consisting of MLYNPTTYQ (SEQ ID NO:20); and/or
k) does not induce phosphorylation of HER1 in A549 cancer cells in the absence of EGF (see Example 6); and/or
l) is a non-agonistic antibody with respect to the phosphorylation of HER1 in the absence of EGF (see Example 6); and/or
m) shows more than 70 percent internalization of HER1 in the presence of EGF after 2 h after incubation with the antibody in a Western Blot assay with HER1 expressing A549 cells and shows less than 55 percent internalization of HER1 in the absence of EGF after 2 h after incubation with the antibody in a Western Blot assay with HER1 expressing A549 cells (see Example 5).

Preferably the HVRs are determined according to Kabat.
In a further aspect, the invention provides an antibody that binds to the same epitope as an anti-HER1 antibody provided herein. For example, in certain embodiments, an antibody is provided that binds to the same epitope as an anti-HER1 antibody selected from the group consisting of:
i) deposited antibody MAK <HER1-DIB> M-50.097.14 (DSM ACC3240);
ii) deposited antibody MAK <HER1-DIB> M-50.110.23 (DSM ACC3241);
iii) deposited antibody MAK <HER1-DIB> M-37.058.09 (DSM ACC3238); and
iv) deposited antibody MAK <HER1-DIB> M-37.186.15 (DSM ACC3239).

In one preferred embodiment an antibody is provided that binds to the same epitope as anti-HER1 antibody:
i) deposited antibody MAK <HER1-DIB> M-50.097.14 (DSM ACC3240); or
ii) deposited antibody MAK <HER1-DIB> M-50.110.23 (DSM ACC3241).

In a further aspect, the invention provides an antibody that competes for binding to human HER1 with an anti-HER1 antibody provided herein. For example, in certain embodiments, an antibody is provided that competes for binding to human HER1 with an anti-HER1 antibody selected from the group consisting of:
 i) deposited antibody MAK <HER1-DIB> M-50.097.14 (DSM ACC3240);
 ii) deposited antibody MAK <HER1-DIB> M-50.110.23 (DSM ACC3241);
 iii) deposited antibody MAK <HER1-DIB> M-37.058.09 (DSM ACC3238); and
 iv) deposited antibody MAK <HER1-DIB> M-37.186.15 (DSM ACC3239).

In one preferred embodiment an antibody is provided that competes for binding to human HER1 with anti-HER1 antibody:
 i) deposited antibody MAK <HER1-DIB> M-50.097.14 (DSM ACC3240); and
 ii) deposited antibody MAK <HER1-DIB> M-50.110.23 (DSM ACC3241).

In certain embodiments, an antibody is provided that binds to an epitope within a fragment of human HER1 consisting of amino acids MLYNPTTYQ (SEQ ID NO:20).

In certain embodiments, an antibody is provided that binds to an epitope within a fragment of human HER1 consisting of amino acids TYQMDVNPEG (SEQ ID NO:19).

In one preferred embodiment the antibody is of IgG1 or IgG4 isotype. In one preferred embodiment the antibody comprises constant domains of human origin (human constant domains). Typical human constant regions within the meaning of the present invention comprising the respective human constant domains have the amino acid sequences of SEQ ID NO: 21 to SEQ ID NO:26 (which partly comprise amino acid substitutions).

1. Antibody Affinity

In certain embodiments, an antibody provided herein has a dissociation constant KD of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

In one preferred embodiment, KD is measured using surface plasmon resonance assays using a BIACORE® at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$ or ka) and dissociation rates ($k_{off}$ or kd) are calculated using a simple one-to-one Langmuir binding model (BIACORE® Evaluation Software version 3.2) by simultaneously fitting the association and dissociation sensorgrams. The equilibrium dissociation constant KD is calculated as the ratio kd/ka ($k_{off}/k_{on}$). See, e.g., Chen, Y. et al., J. Mol. Biol. 293 (1999) 865-881. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing SDR (a-CDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling). Morea, V., et al., Methods, Vol 20, Issue 3 (2000) 267-279) and WO2004/006955 (approach via canonical structures).

4. Human Antibodies

In certain embodiments, an antibody provided herein is a human antibody. Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, D., J. Immunol. 133 (1984) 3001-3005; Brodeur, B. R. et al., Monoclonal Antibody Production Techniques and Applications, Marcel Dekker, Inc., New York (1987), pp. 51-63; and Boerner, P. et al., J. Immunol. 147 (1991) 86-95) Human antibodies generated via human B-cell hybridoma technology are also described in Li, J. et al., Proc. Natl. Acad. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G. et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths, A. D. et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for HER1 and the other is for any other antigen. Bispecific antibodies may also be used to localize cytotoxic agents to cells which express HER1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to HER1 as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions". More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |

TABLE 1-continued

| Original Residue | Exemplary Substitutions | Preferred Substitutions |
| --- | --- | --- |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or SDRs (a-CDRs), with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc (RIII only, whereas monocytes express FcgammaRI, FcgammaRII and FcgammaRIII. FcR expression on hematopoietic cells is summarized in Table 3 on page 464 of Ravetch, J. V. and Kinet, J. P., Annu Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and Cyto-Tox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006: 1759-1769).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan, A. R. and Winter, G., Nature 322 (1988) 738-740; U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-HER1 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-HER1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-HER1 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. No. 5,648,237, U.S. Pat. No. 5,789,199, and U.S. Pat. No. 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays and Antibody (or Antigen Binding Protein) Selection Methods

Anti-HER1 antibodies provided herein may be identified, screened for, or characterized for their physical/chemical properties and/or biological activities by various assays known in the art.

One aspect of the invention is a method for selecting an antibody (or antigen binding protein) that binds to human HER1, wherein the antibody (or antigen binding protein) binds within an amino acid sequence of PPLMLYNPTTYQMDVNPEGK (SEQ ID NO:1) of human HER1; wherein a) at least one polypeptide selected from the group consisting of:

|  |  |
|---|---|
| TtSlyDcas-HER1, | SEQ ID NO: 12 |
| TtSlyDcys-HER1, | SEQ ID NO: 13 |
| TtSlyD(GSG)-HER1, | SEQ ID NO: 14 |
| TtSlyD(CC)-HER1, | SEQ ID NO: 15 |
| TtSlyD(SS)-HER1, and | SEQ ID NO: 16 |
| TgSlyDcys-HER1, | SEQ ID NO: 18 | which comprises the amino acid sequence of SEQ ID NO:1;

is used to select (in a binding assay) antibodies (or antigen binding proteins), which show binding to the at least one polypeptide under a), and thereby selecting an antigen binding protein, in particular an antibody that binds within an amino acid sequence of PPLMLYNPTTYQMDVNPEGK (SEQ ID NO:1) of human HER1.

In one embodiment such selection methods further comprises a step wherein the selected antibodies are counter-screened with the polypeptides (tested for binding to the polypeptides) selected from the group consisting of:

|  |  |
|---|---|
| TtSlyDcas | SEQ ID NO: 11 |
| TgSlyDΔIF | SEQ ID NO: 17 | to confirm that the selected antibodies do not bind to the polypeptide scaffolds which are not comprising amino acid sequence of PPLMLYNPTTYQMDVNPEGK (SEQ ID NO:1).

The invention provides an antibody (or antigen binding protein) obtained by such selection method.

A method for selecting an antibody (or antigen binding protein) that specifically binds to a human HER1, comprising the following steps:

a) determining the binding affinity of a plurality of antibodies (or antigen binding proteins) to the β-hairpin of HER1 with the amino acid sequence of SEQ ID NO:1, whereby β-hairpin of HER1 is presented as polypeptide selected from the group consisting of:

i) TtSlyDcas-HER1, SEQ ID NO: 12 ii) TtSlyDcys-HER1, SEQ ID NO: 13 iii) TtSlyD(GSG)-HER1, SEQ ID NO: 14 iv) TtSlyD(CC)-HER1, SEQ ID NO: 15 v) TtSlyD(SS)-HER1, SEQ ID NO: 16
and vi) TgSlyDcys-HER1, SEQ ID NO: 18 which comprise the β-hairpin of HER1 with the amino acid sequence of SEQ ID NO:1,
b) selecting the antibody (or antigen binding protein) having an apparent complex stability above a pre-defined threshold level.

1. Binding Assays and Other Assays

In one aspect, an antibody (or antigen binding protein) of the invention is tested for its antigen binding activity, e.g., by known methods such as ELISA, Western blot, including surface plasmon resonance (e.g. BIACORE), etc.

In another aspect, competition assays may be used to identify an antibody that competes with
i) deposited antibody MAK <HER1-DIB> M-50.097.14 (DSM ACC3240);
ii) deposited antibody MAK <HER1-DIB> M-50.110.23 (DSM ACC3241);
iii) deposited antibody MAK <HER1-DIB> M-37.058.09 (DSM ACC3238); or
iv) deposited antibody MAK <HER1-DIB> M-37.186.15 (DSM ACC3239);
for binding to HER1.

In certain embodiments, such a competing antibody binds to the same epitope (e.g., a linear or a conformational epitope) that is bound by
i) deposited antibody MAK <HER1-DIB> M-50.097.14 (DSM ACC3240;
ii) deposited antibody MAK <HER1-DIB> M-50.110.23 (DSM ACC3241);
iii) deposited antibody MAK <HER1-DIB> M-37.058.09 (DSM ACC3238); or
iv) deposited antibody MAK <HER1-DIB> M-37.186.15 (DSM ACC3239).

Detailed exemplary methods for mapping an epitope to which an antibody binds are provided in Morris, G. E. (ed.), Epitope Mapping Protocols, In: Methods in Molecular Biology, Vol. 66, Humana Press, Totowa, N.J. (1996). Further methods are described in detail in Example 4 using the CelluSpot™ technology.

In an exemplary competition assay, immobilized HER1 is incubated in a solution comprising a first labeled antibody that binds to HER1, respectively (e.g. deposited antibodies MAK <HER1-DIB> M-50.097.14 (DSM ACC3240MAK <HER1-DIB> M-50.110.23 (DSM ACC3241); MAK <HER1-DIB> M-37.058.09 (DSM ACC3238); MAK <HER1-DIB> M-37.186.15 (DSM ACC3239)) and a second unlabeled antibody that is being tested for its ability to compete with the first antibody for binding to HER1. The second antibody may be present in a hybridoma supernatant. As a control, immobilized HER1 is incubated in a solution comprising the first labeled antibody but not the second unlabeled antibody. After incubation under conditions permissive for binding of the first antibody to HER1, excess unbound antibody is removed, and the amount of label associated with immobilized HER1 is measured. If the amount of label associated with immobilized HER1 is substantially reduced in the test sample relative to the control sample, then that indicates that the second antibody is competing with the first antibody for binding to HER1. See Harlow, E. and Lane, D., Antibodies: A Laboratory Manual, Chapter 14, Cold Spring Harbor Laboratory, Cold Spring Harbor, N.Y. (1988).

2. Activity Assays

In one aspect, assays are provided for identifying anti-HER1 antibodies (or antigen binding proteins) thereof having biological activity. Biological activity may include, e g, inhibition of HER1 phosphorylation, non-agonistic activity with respect to HER1 phosphorylation in the absence of EGF, inhibition of cancer cell proliferation of HER1 expressing or overexpressing cancer cells, inhibition of HER1/HER1 homodimerization inhibition of HERVHER2 heterodimerization, (time-dependent) internalization via Western Blot or FACS assay, in vivo tumor growth inhibition in xenograft animal (e.g. mouse or rat) models with xenografted HER1 expressing or overexpressing cancer cells. Antibodies having such biological activity either alone or as immunoconjugates with a cytotoxic agent in vivo and/or in vitro are also provided.

In certain embodiments, an antibody of the invention is tested for such biological activity. Exemplary vitro or in vivo assays for specified biological activities are described in Example 2e, and Examples 5, 6 and 8.

D. Immunoconjugates

The invention also provides immunoconjugates comprising an anti-HER1 antibody (or antigen binding protein) described herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. No. 5,208,020, U.S. Pat. No. 5,416,064 and EP 0 425 235 B1); an auristatin such as monomethyl auristatin drug moieties DE and DF (MMAE and MMAF) (see U.S. Pat. No. 5,635,483, U.S. Pat. No. 5,780,588, and U.S. Pat. No. 7,498,298); a dolastatin; a calicheamicin or derivative thereof (see U.S. Pat. No. 5,712,374, U.S. Pat. No. 5,714,586, U.S. Pat. No. 5,739,116, U.S. Pat. No. 5,767,285, U.S. Pat. No. 5,770,701, U.S. Pat. No. 5,770,710, U.S. Pat. No. 5,773,001, and U.S. Pat. No. 5,877,296; Hinman, L. M. et al., Cancer Res. 53 (1993) 3336-3342; and Lode, H. N. et al., Cancer Res. 58 (1998) 2925-2928); an anthracycline such as daunomycin or doxorubicin (see Kratz, F. et al., Curr. Med. Chem. 13 (2006) 477-523; Jeffrey, S. C. et al., Bioorg. Med. Chem. Lett. 16 (2006) 358-362; Torgov, M. Y. et al., Bioconjug. Chem. 16 (2005) 717-721; Nagy, A. et al., Proc. Natl. Acad. Sci. USA 97 (2000) 829-834; Dubowchik, G. M. et al., Bioorg. & Med.

Chem. Letters 12 (2002) 1529-1532; King, H. D. et al., J. Med. Chem. 45 (20029 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a *Pseudomonas* exotoxin A or variants thereof. *Pseudomonas* exotoxin A or variants thereof are described e.g in WO2011/32022, WO2009/32954, WO2007/031741, WO2007/016150, WO2005/052006 and Liu W, et al, PNAS 109 (2012) 11782-11787.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made a) either using recombination expression techniques (e.g for the expression of amino acid sequence based toxins fused to a Fab or Fv antibody fragment e.g. in *E. coli*) or b) using polypeptide coupling techniques (like sortase enzyme based coupling of amino acid sequence based toxins to a Fab or Fv antibody fragment) or c) using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S. et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V. et al., Cancer Res. 52 (1992) 127-131; U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-HER1 antibodies (or antigen binding proteins) provided herein is useful for detecting the presence of HER1, respectively in a biological sample. The term "detecting" as used herein encompasses quantitative or qualitative detection. In certain embodiments, a biological sample comprises a cell or tissue, such as tumor tissues.

In one embodiment, an anti-HER1 antibody for use in a method of diagnosis or detection is provided. In a further aspect, a method of detecting the presence of HER1, respectively, in a biological sample is provided. In certain embodiments, the method comprises contacting the biological sample with an anti-HER1 antibody as described herein under conditions permissive for binding of the anti-HER1 antibody to HER1, respectively, and detecting whether a complex is formed between the anti-HER1 antibody and HER1, respectively. Such method may be an in vitro or in vivo method. In one embodiment, an anti-HER1 antibody is used to select subjects eligible for therapy with an the anti-HER1 antibodies antibody, e.g. where HER1, respectively are both biomarkers for selection of patients.

Exemplary disorders that may be diagnosed using an antibody of the invention include cancer.

In certain embodiments, labeled anti-HER1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-HER1 antibody (or antigen binding protein) as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-HER1 antibodies (or antigen binding proteins) or immunoconjugates of the anti-HER1 antibodies (or antigen binding protein) conjugated to a cytotoxic agent, provided herein may be used in therapeutic methods.

In one aspect, an anti-HER1 antibody or immunoconjugate of the anti-HER1 antibody conjugated to a cytotoxic agent for use as a medicament is provided. In further aspects, an anti-HER1 antibody or immunoconjugate of the anti-HER1 antibody conjugated to a cytotoxic agent for use in treating cancer is provided. In certain embodiments, an anti-HER1 antibody or immunoconjugates of the anti-HER1 antibody conjugated to a cytotoxic agent for use in a method of treatment is provided. In certain embodiments, the invention provides an anti-HER1 antibody or immunoconjugate of the anti-HER1 antibody conjugated to a cytotoxic agent for use in a method of treating an individual having cancer comprising administering to the individual an effective amount of the anti-HER1 antibody or the immunoconjugate of the anti-HER1 antibody conjugated to a cytotoxic agent. In further embodiments, the invention provides an anti-HER1 antibody or immunoconjugate of the anti-HER1 antibody conjugated to a cytotoxic agent for use in inducing apoptosis in a cancer cell/or inhibiting cancer cell proliferation. In certain embodiments, the invention provides an anti-HER1 antibody or immunoconjugate of the anti-HER1 antibody conjugated to a cytotoxic agent for use in a method of inducing apoptosis in a cancer cell/or inhibiting cancer cell proliferation in an individual comprising administering to the individual an effective of the anti-HER1 antibody or immunoconjugate of the anti-HER1 antibodies conjugated to a cytotoxic agent to induce apoptosis in a cancer cell/or to inhibit cancer cell proliferation. An "individual" according to any of the above embodiments is preferably a human.

In a further aspect, the invention provides for the use of an anti-HER1 antibody or an immunoconjugate of the anti-HER1 antibody conjugated to a cytotoxic agent in the manufacture or preparation of a medicament. In one embodiment, the medicament is for treatment of cancer. In a further embodiment, the medicament is for use in a method of treating cancer comprising administering to an individual having cancer an effective amount of the medicament. In a further embodiment, the medicament is for inducing apoptosis in a cancer cell/or inhibiting cancer cell proliferation. In a further embodiment, the medicament is for use in a method of inducing apoptosis in a cancer cell/or inhibiting cancer cell proliferation in an individual suffering from cancer comprising administering to the individual an amount effective of the medicament to induce apoptosis in a cancer cell/or to inhibit cancer cell proliferation. An "individual" according to any of the above embodiments may be a human.

In a further aspect, the invention provides a method for treating cancer. In one embodiment, the method comprises administering to an individual having cancer an effective amount of an anti-HER1 antibody. An "individual" according to any of the above embodiments may be a human.

In a further aspect, the invention provides a method for inducing apoptosis in a cancer cell/or inhibiting cancer cell proliferation in an individual suffering from cancer. In one embodiment, the method comprises administering to the individual an effective amount of an anti-HER1 antibody or an immunoconjugate of the anti-HER1 antibody conjugated to a cytotoxic compound to induce apoptosis in a cancer cell/or to inhibit cancer cell proliferation in the individual suffering from cancer. In one embodiment, an "individual" is a human.

In a further aspect, the invention provides pharmaceutical formulations comprising any of the anti-HER1 antibodies provided herein, e.g., for use in any of the above therapeutic methods. In one embodiment, a pharmaceutical formulation comprises any of the anti-HER1 antibodies provided herein and a pharmaceutically acceptable carrier.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-HER1 antibody.

III. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-HER1 antibody.

Description of the Amino Acid Sequences

SEQ ID NO: 1 β-Hairpin of human HER1
SEQ ID NO: 2 human HER1
SEQ ID NO: 3 human HER1 Extracellular Domain (ECD)
SEQ ID NO: 4 human EGF
SEQ ID NO: 5 human HER2
SEQ ID NO: 6 human HER2 Extracellular Domain (ECD)
SEQ ID NO: 7 human HER3
SEQ ID NO: 8 human HER3 Extracellular Domain (ECD)
SEQ ID NO: 9 human HER4
SEQ ID NO: 10 human HER4 Extracellular Domain (ECD)
SEQ ID NO: 11 TtSlyDcas
SEQ ID NO: 12 TtSlyDcas-HER1
SEQ ID NO: 13 TtSlyDcys-HER1
SEQ ID NO: 14 TtSlyD(GSG)-HER1
SEQ ID NO: 15 TtSlyD(CC)-HER1
SEQ ID NO: 16 TtSlyD(SS)-HER1
SEQ ID NO: 17 TgSlyDΔIF
SEQ ID NO: 18 TgSlyDcys-HER1
SEQ ID NO: 19 HER1 binding epitope of HER1 antibody M-47-13
SEQ ID NO: 20 HER1 binding epitope of HER1 antibodies M-50-14 (deposited MAK <HER1-DIB> M-50.097.14) and M-50-23 (deposited MAK <HER1-DIB> M-50.110.23)
SEQ ID NO: 21 human kappa light chain constant region
SEQ ID NO: 22 human lambda light chain constant region
SEQ ID NO: 23 human heavy chain constant region derived from IgG1
SEQ ID NO: 24 human heavy chain constant region derived from IgG1 mutated on L234A and L235A
SEQ ID NO: 25 human heavy chain constant region derived from IgG1 mutated on L234A, L235A and P329G
SEQ ID NO: 26 human heavy chain constant region derived from IgG4

The following examples and figures are provided to aid the understanding of the present invention, the true scope of which is set forth in the appended claims. It is understood that modifications can be made in the procedures set forth without departing from the spirit of the invention.

In the following several embodiments of the invention are listed:

1. A method for selecting an antigen binding protein that binds to human HER1, wherein the antigen binding protein binds within an amino acid sequence of PPLMLYNPTTYQMDVNPEGK (SEQ ID NO:1) of human HER1;
   wherein
   a) at least one polypeptide selected from the group consisting of:

TtSlyDcas-HER1, SEQ ID NO: 12
   TtSlyDcys-HER1, SEQ ID NO: 13
   TtSlyD(GSG)-HER1, SEQ ID NO: 14
   TtSlyD(CC)-HER1, SEQ ID NO: 15
   TtSlyD(SS)-HER1, SEQ ID NO: 16
   and
   TgSlyDcys-HER1, SEQ ID NO: 18 which comprises the amino acid sequence of SEQ ID NO: 1;
   is used to select antigen binding proteins, which show binding to the at least one polypeptide under a)
   and thereby selecting an antigen binding protein that binds within an amino acid sequence of PPLMLYNPTTYQMDVNPEGK (SEQ ID NO:1) of human HER1.

2. An antigen binding protein obtained by the selection method of embodiment 1.

3. The method of embodiment 1, or the antigen binding protein of embodiment 2 wherein the antigen binding protein is an antibody.

4. An isolated antigen binding protein that binds to human HER1
   wherein the antigen binding protein binds to a polypeptide of TtSlyDcys-Her1 SEQ ID NO: 13 with an at least 50 times higher ELISA signal when compared to the binding to a polypeptide of TtSlyDcas SEQ ID NO: 11 in an ELISA assay, wherein TtSlyDcys-HER1 and TtSlyDcas were immobilized at a concentration of 0.5 µg/ml.

5. An isolated antigen binding protein that binds to human HER1, wherein the antigen binding protein binds within an amino acid sequence of PPLMLYNPTTYQMDVNPEGK (SEQ ID NO:1) which is comprised in a polypeptide of SEQ ID NO: 13 (TtSlyDcys-Her1).

6. The antigen binding protein of embodiments 4 or 5 wherein the antigen binding protein is an antibody.

7. An isolated antigen binding protein or antibody of any one of the preceding embodiments, wherein the antibody does not induce phosphorylation of HER1 in A549 cancer cells (ATCC CCL-185) in the absence of EGF (is a non-agonistic antibody with respect to the phosphorylation of HER1 in the absence of EGF in A549 cancer cells (ATCC CCL-185)).

8. An isolated antibody of any one of the preceding embodiments, wherein the antibody
   shows more than 70 percent internalization of HER1 in the presence of EGF after 2 h after incubation with the antibody in a Western Blot assay with HER1 expressing A549 cells (ATCC CCL-185) and shows less than 55 percent internalization of HER1 in the absence of EGF after 2 h after incubation with the antibody in a Western Blot assay with HER1 expressing A549 cells.

9. An isolated antibody that binds to human HER1, wherein the antibody binds to a polypeptide with a length of 15 amino acids, the polypeptide comprising the amino acid sequence of TYQMDVNPEG (SEQ ID NO:19).

10. An isolated antibody that binds to human HER1, wherein the antibody binds to a polypeptide with a length of 15 amino acids, the polypeptide comprising the amino acid sequence of MLYNPTTYQ (SEQ ID NO:20).

11. The antibody of embodiments 6 to 10, which is a human, humanized, or chimeric antibody.

12. The antibody of embodiments 6 to 10, which is an antibody fragment that binds human HER1.

13. An isolated antibody that binds to human HER1, wherein the antibody comprises
   i) (a) HVR-H1; (b) HVR-H2; (c) HVR-H3; (d) HVR-L1; (e) HVR-L2; and (f) HVR-L3 of deposited antibody MAK <HER1-DIB> M-50.097.14 (DSM ACC3240);
   ii) (a) HVR-H1; (b) HVR-H2; (c) HVR-H3; (d) HVR-L1; (e) HVR-L2; and (f) HVR-L3 of deposited antibody MAK <HER1-DIB> M-50.110.23 (DSM ACC3241);
   iii) (a) HVR-H1; (b) HVR-H2; (c) HVR-H3; (d) HVR-L1; (e) HVR-L2; and (f) HVR-L3 of deposited antibody MAK <HER1-DIB> M-37.058.09 (DSM ACC3238);
   iv) (a) HVR-H1; (b) HVR-H2; (c) HVR-H3; (d) HVR-L1; (e) HVR-L2; and (f) HVR-L3 of deposited antibody MAK <HER1-DIB> M-37.186.15 (DSM ACC3239);
   wherein the all HVRs are determined according to Kabat.

14. The antibody of any one of embodiments 6 to 13, which is a full length IgG1 antibody or IgG4 antibody.

15. The antibody of any one of embodiments 6 to 13, which is a Fab fragment.

16. An immunoconjugate comprising the antibody of any one of embodiments 6 to 13 and a cytotoxic agent.

17. A pharmaceutical formulation comprising the antibody of any one of embodiments 6 to 13, or the immunoconjugate of embodiment 16, and a pharmaceutically acceptable carrier.

18. The antibody of any one of embodiments 6 to 13, or the immunoconjugate of embodiment 16, for use as a medicament.

19. The antibody of any one of embodiments 6 to 13, or the immunoconjugate of embodiment 16, for use in treating cancer.

20. The antibody of any one of embodiments 6 to 13 for use in inhibition of HER1/HER2 and/or HER1/HER1 dimerization.

21. Use of the antibody of any one of embodiments 6 to 13, or the immunoconjugate of embodiment 16, in the manufacture of a medicament.

22. The use of embodiment 20, wherein the medicament is for treatment of cancer.
23. The use the antibody of any one of embodiments 6 to 13 in the manufacture of a medicament, wherein the medicament is for the inhibition of HER1/HER2 and/or HER1/HER1 dimerization.
24. A method of treating an individual having cancer comprising administering to the individual an effective amount of the antibody of any one of the preceding embodiments, or an immunoconjugate comprising the antibody of any one of the preceding embodiments and a cytotoxic agent.
25. A method of inducing apoptosis in a cancer cell in an individual suffering from cancer comprising administering to the individual an effective amount of an immunoconjugate comprising the antibody of any one of the preceding embodiments and a cytotoxic agent, thereby inducing apoptosis in a cancer cell in the individual.
26. Isolated nucleic acid encoding the antibody of any one of embodiments 6 to 11.
27. A host cell comprising the nucleic acid of embodiment 26.
28. A method of producing an antibody comprising culturing the host cell of embodiment 27 so that the antibody is produced.
29. A polypeptide selected from the group consisting of:

i)
TtSlyDcas-HER1,  SEQ ID NO: 12 ii)
TtSlyDcys-HER1,  SEQ ID NO: 13 iii)
TtSlyD(GSG)-HER1,  SEQ ID NO: 14 iv)
TtSlyD(CC)-HER1,  SEQ ID NO: 15 v)
TtSlyD(SS)-HER1,  SEQ ID NO: 16
and vi)
TgSlyDcys-HER1,  SEQ ID NO: 18 which polypeptide comprises the amino acid sequence of SEQ ID NO:1.

Deposit of Biological Material

The following biological material has been deposited with Leibniz-Institut Deutsche Sammlung von Mikroorganismen and Zellkulturen GmbH (DSMZ), Inhoffenstr. 7 B, 38124 Braunschweig, Germany according to the Budapest treaty.

| Antibody Designation (hybridoma cell line) | Deposition No. | Date of deposit |
|---|---|---|
| MAK <HER1-DIB> M-50.097.14 | DSM ACC3240 | 8 May 2014 |
| MAK <HER1-DIB> M-50.110.23 | DSM ACC3241 | 8 May 2014 |
| MAK <HER1-DIB> M-37.058.09 | DSM ACC3238 | 8 May 2014 |
| MAK <HER1-DIB> M-37.186.15 | DSM ACC3239 | 8 May 2014 |

EXAMPLES

Materials & General Methods
Recombinant DNA Techniques

Standard methods were used to manipulate DNA as described in Sambrook, J. et al., Molecular Cloning: A laboratory manual; Cold Spring Harbor Laboratory Press, Cold Spring Harbor, N.Y., 1989. The molecular biological reagents were used according to the manufacturer's instructions.

Gene Synthesis

Desired gene segments were prepared from oligonucleotides made by chemical synthesis. The 400-1600 bp long gene segments, which were flanked by singular restriction endonuclease cleavage sites, were assembled by annealing and ligating oligonucleotides including PCR amplification and subsequently cloned via the indicated restriction sites e.g. EcoRI/BlpI or BsmI/XhoI into the expression vectors described below. The DNA sequences of the subcloned gene fragments were confirmed by DNA sequencing. Gene synthesis fragments were ordered according to given specifications at Geneart (Regensburg, Germany).

DNA Sequence Determination

DNA sequences were determined by double strand sequencing performed at Sequiserve GmbH (Vaterstetten, Germany).

DNA and Protein Sequence Analysis and Sequence Data Management

Infomax's Vector NT1 Advance suite version 11.5.0 was used for sequence creation, mapping, analysis, annotation and illustration.

Example 1

Preparation of Antigen and Screening Proteins—Generation of Functional β-Hairpin HER1 Constructs for Selecting Antibodies Binding to the β-Hairpin of HER1

To generate functional β-Hairpin HER1 constructs, the amino acid sequences of the HER1 β-HairpinHER1, was grafted into a SlyD polypeptide framework comprising a FKBP domain. In such constructs the grafted β-Hairpins are freely accessible in contrast to the hidden structure in the native unactivated conformation of HER1 (in the absence of ligand as e.g. EGF) (see FIGS. 1 and 2, where the β-Hairpin of HER1 is hidden).

All fused SlyD polypeptides can be purified and refolded by using almost identical protocols. E. coli BL21 (DE3) cells transformed with the particular expression plasmid were grown at 37° C. in LB medium containing the respective antibiotic for selective growth (Kanamycin 30 μg/ml, or Ampicillin (100 μg/ml)) to an OD600 of 1.5, and cytosolic overexpression was induced by adding 1 mM isopropyl-β-D-thiogalactoside (IPTG). Three hours after induction, cells were harvested by centrifugation (20 min at 5,000 g), frozen and stored at −20° C. For cell lysis, the frozen pellet was resuspended in chilled 50 mM sodium phosphate buffer (pH 8.0) supplemented with 7 M GdmCl and 5 mM imidazole. Thereafter the suspension was stirred for 2-10 hours on ice to complete cell lysis. After centrifugation (25,000 g, 1 h) and filtration (cellulose nitrate membrane, 8.0 μm, 1.2 μm, 0.2 μm), the lysate was applied onto a Ni-NTA column equilibrated with the lysis buffer. In the subsequent washing step the imidazole concentration was raised to 10 mM (in 50 mM sodium phosphate buffer (pH 8.0) comprising 7 M GdmCl) and 5 mM TCEP was added in order to keep the thiol moieties in a reduced form and to prevent premature disulfide bridging. At least 15 to 20 volumes of the reducing washing buffer were applied. Thereafter, the GdmCl solution was replaced by 50 mM sodium phosphate buffer (pH 8.0) comprising 100 mM NaCl, 10 mM imidazole, and 5 mM TCEP to induce conformational refolding of the matrixbound SlyD fusion polypeptide. In order to avoid reactivation of co-purifying proteases, a protease inhibitor cocktail (Complete® EDTA-free, Roche) was added to the refolding buffer. A total of 15 to 20 column volumes of refolding buffer were applied in an overnight procedure. Thereafter, both TCEP and the Complete® EDTA-free inhibitor cocktail were removed by washing with 10 column volumes 50 mM sodium phosphate buffer (pH 8.0) comprising 100 mM NaCl and 10 mM imidazole. In the last washing step, the imidazole concentration was raised to 30 mM (10 column volumes) in order to remove tenacious contaminants. The refolded polypeptide was then eluted by applying 250 mM imidazole in the same buffer. Protein-containing fractions were assessed for purity by Tricine-SDS-PAGE (Schaegger, H. and von Jagow, G., Anal. Biochem. 166 (1987) 368-379).

Figure 3:
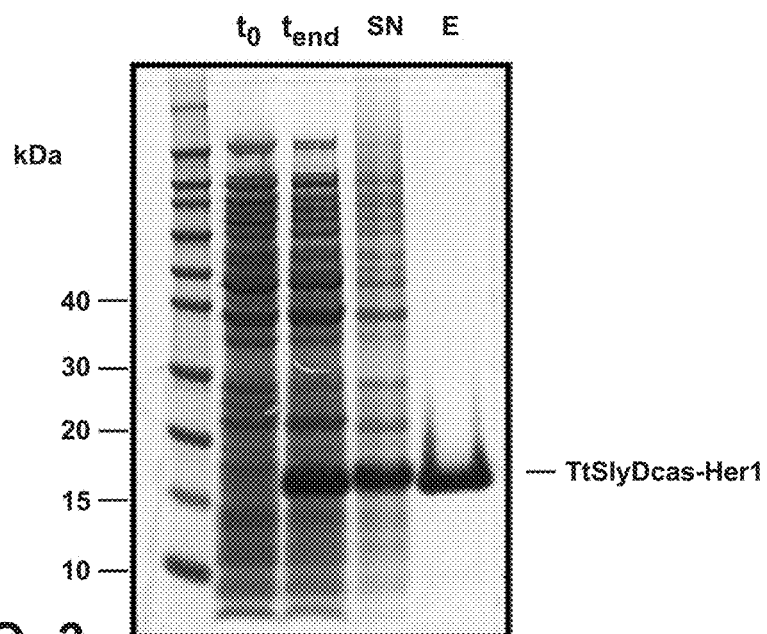
Figure 4:
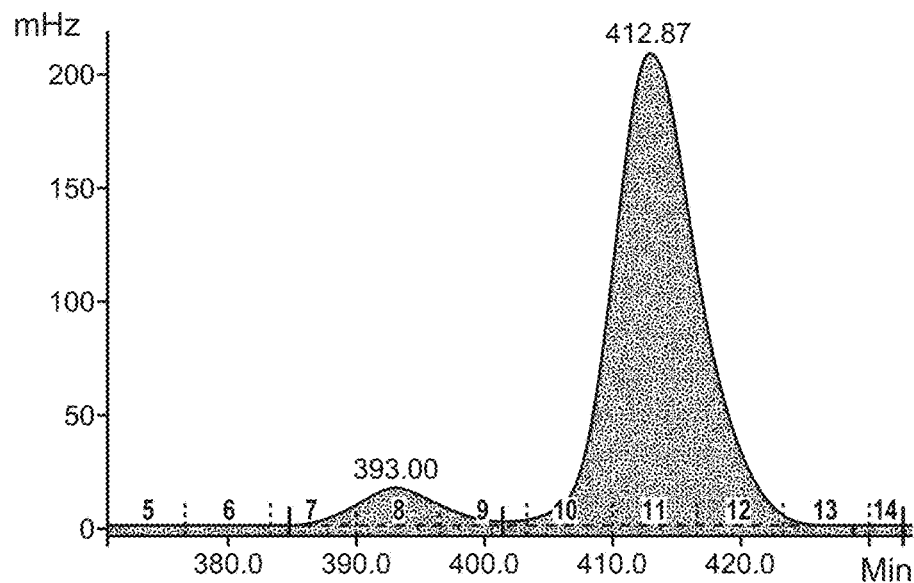

Subsequently, the protein was subjected to size-exclusion-chromatography (Superdex™ HiLoad, Amersham Pharmacia) using potassium phosphate as the buffer system (50 mM potassium phosphate buffer (pH 7.0), 100 mM KCl, 0.5 mM EDTA). Finally, the protein-containing fractions were pooled and concentrated in an Amicon cell (YM10) to a concentration of ~5 mg/ml. Exemplarily SDS-PAGE analysis of Ni-NTA purification of TtSlyDcas-HER1 is shown in FIG. 3 and SEC elution profile of a Ni-NTA purified fraction of *Thermus thermophilus* SlyDcas-HER1 is shown in FIG. 4. The TtSlyDcas-HER1 fusion polypeptide could be purified successfully as a soluble and stable polypeptide in its monomeric form. The final yield was quantified at 30 mg purified protein from fraction 11 and 12.

TABLE 2

Summary of the amino acid sequences of the developed
SlyD-based epitope scaffolds (which carry the HER1
dimerization domain fragment HER1 as insert.
*Thermus thermophilus* TtSlyDcas-HER1, TtSlyDcys-HER1,
TtSlyD(GSG)-HER1, TtSlyD(CC)-HER1, TtSlyD(SS)-HER1,
*Thermococcus gammatolerans* TgSlyDcys-HER1
carry the HER1 dimerization domain fragment (β-Hairpin
of HER1) as insert and were used as immunogens
and as positive controls in ELISA screening.
TtSlyDcas and TgSlyDΔIF were used as negative controls
in the ELISA screening (without the HER1 dimerization
domain fragment (β-Hairpin of HER1 as insert).
As the epitope scaffolds are expressed in *E. coli* the
N-terminal methionine residue can be present or not.
(Nt = N-terminal; Ct = C-terminal)

| | |
|---|---|
| TtSlyDcas SEQ ID NO: 11 | Nt-MRSKVGQDKVVTIRYTLQVEGEVLDQGELSYLHGHRNLIPGL EEALEGREEGEAFQAHVPAEKAYGAGSGSSGKDLDFQVEVV KVREATPEELLHGHAHGGGSRKHHHHHHHH-Ct |
| TtSlyDcas-HER1 SEQ ID NO: 12 | Nt-MRSKVGQDKVVTIRYTLQVEGEVLDQGELSYLHGHRNLIPGL EEALEGREEGEAFQAHVPAEKAYGAGSPPLMLYNPTTYQMD VNPEGKGSSGKDLDFQVEVVKVREATPEELLHGHAHGGGSR KHHHHHHHH-Ct |
| TtSlyDcys-HER1 SEQ ID NO: 13 | Nt-MRSKVGQDKVVTIRYTLQVEGEVLDQGELSYLHGHRNLIPGL EEALEGREEGEAFQAHVPAEKAYGPCGPPLMLYNPTTYQMD VNPEGGCGKDLDFQVEVVKVREATPEELLHGHAHGGGSRKH HHHHHHH-Ct |
| TtSlyD(GSG)-HER1 SEQ ID NO: 14 | Nt-MRSKVGQDKVVTIRYTLQVEGEVLDQGELSYLHGHRNLIPGL EEALEGREEGEAFQAHVPAEKAYGSGPPLMLYNPTTYQMDV NPEGKGSGKDLDFQVEVVKVREATPEELLHGHAHGGGSRKH HHHHHHH-Ct |
| TtSlyD(CC)-HER1 SEQ ID NO: 15 | Nt-MRSKVGQDKVVTIRYTLQVEGEVLDQGELSYLHGHRNLIPGL EEALEGREEGEAFQAHVPAEKAYGCPPLMLYNPTTYQMDVN PEGKCGKDLDFQVEVVKVREATPEELLHGHAHGGGSRKHHH HHHHH-Ct |
| TtSlyD(SS)-HER1 SEQ ID NO: 16 | Nt-MRSKVGQDKVVTIRYTLQVEGEVLDQGELSYLHGHRNLIPGL EEALEGREEGEAFQAHVPAEKAYGSPPLMLYNPTTYQMDVN PEGKSGKDLDFQVEVVKVREATPEELLHGHAHGGGSRKHHH HHHHH-Ct |
| TgSlyDΔIF SEQ ID NO: 17 | Nt-MKVERGDFVLFNYVGRYENGEVFDTSYESVAREQGIFVEERE YSPIGVTVGAGEIIPGIEEALLGMELGEKKEVVVPPEKGYGAT GHPGIIPPHATAIFEIEVVEIKKAGEALEHHHHHHLEHHHHHH-Ct |
| TgSlyDcys-HER1 SEQ ID NO: 18 | Nt-MRGSKVERGDFVLFNYVGRYENGEVFDTSYESVAREQ GIFVEEREYSPIGVTVGAGEIIPGIEEALLGMELGEKKEV VVPPEKGYGMPCGPPLMLYNPTTYQMDVNPEGGCAGK TAIFEIEVVEIKKAGEAGGGSHHHHHHHH-Ct |

Example 2 a) Immunisation and Selection of HER1 Antibodies

For the generation of antibodies against the β-hairpin of HER1, Balb/C, NMRI or SJL mice were immunized with different antigens. As antigens the following proteins were used: full length HER1 ECD, or the epitope scaffold proteins TtSlyDcas-HER1, TtSlyDcys-HER1 and TtSlyD(GSG)-HER1. The TtSlyDcas-HER1 variant represents the first generation epitope scaffold, used for generation of HER1 dimerization domain specific antibodies.

All mice were subjected to 3 immunizations at the time points 0, 6 and 10 weeks after start of the immunization campaign. At each time point each mouse was immunized with 100 μg endotoxin free immunogen dissolved in 100 μl PBS. For the first immunization the immunogen was mixed with 100 μl CFA. For the second and third immunization the immunogen was mixed with IFA. The first and the third immunization were applied via the intraperitoneal route, the second immunization was applied subcutaneously. 2 and 3 days prior to the preparation of spleenocyte for antibody development using hybridoma technology, the mice were subjected to intravenous booster immunizations with 12.5 μg immunogen in 100 μl PBS and without adjuvant.

Titer Analysis

For the determination of serum titers against the respective immunogen and against the screening proteins a small amount of serum of each mouse was collected in week 11 after start of the immunization campaign. For the ELISA the immunogen or the screening scaffold proteins were immobilized on the plate surface. HER1 ECD was immobilized at a concentration of 1 μg/ml and the scaffold proteins TtSlyDcas-HER1, TtSlyDcys-HER1, TtSlyD(GSG)-HER1, TtSlyDcas, TgSlyDΔIF and TgSlyDcys-HER1 were used at a concentration of 0.5 μg/ml. The scaffold proteins TtSlyDcas and TgSlyDΔIF were used as negative controls. The sera from each mouse were diluted in PBS with 1% BSA and the dilutions were added to the plates. The sera were tested at dilutions 1:300, 1:900, 1:2700, 1:8100, 1:24300, 1:72900, 1:218700 and 1:656100. Bound antibody was detected with a HRP-labeled F(ab')$_2$ goat anti-mouse Fcγ (Dianova) and ABTS (Roche) as a substrate.

Even on the level of serum titration it was already obvious that immunized mice developed antibodies against the HER1 β-hairpin domain. In mice immunized with HER1 ECD this can be shown by titration against one of the scaffold proteins containing the dimerization β-hairpin loop. The strongly reduced signal can be explained by the fact, that the majority of antibodies raised by immunization with HER1 ECD are targeting other parts within the ECD and only a small fraction is binding to the dimerization β-hairpin domain. In mice immunized with HER1 dimerization loop containing scaffolds the fraction of antibodies targeting the loop can be shown by titration against Her1 ECD (positive control) and titration against an control scaffold without HER1 insertion (negative control).

b) Antibody Development and ELISA Screening/Selection

The use of the here described epitope scaffold technology offers in principal two strategies for the development of antibodies targeting the HER1 dimerization domain (β-Hairpins of HER1). One strategy is to immunize with the full length HER1 ECD and to use the scaffolds to screen for the dimerization domain specific antibodies. The other strategy is the direct use of the scaffold for immunization and to use the HER1 ECD, a scaffold with another backbone or a scaffold without insertion for counter screening. Antibodies were developed with hybridoma technology by fusing primary B-cells with P3X63Ag8.653 myeloma cells. 2 days after the final booster immunization, immunized mice were sacrificed and spleen cell populations were prepared. The spleenocytes were fused with P3X63Ag8.653 by using the PEG fusion technology. The cellular batch culture from the fusion was incubated overnight at 37° C. under 5% CO$_2$. The following day the cellular batch containing fused cells was centrifuged for 10 min at 300 g. Thereafter, the cells were suspended in hybridoma selection media supplemented with 0.1× azaserine-hypoxanthine (Sigma) and were seeded at a concentration of 2.5×10$^4$ cells per well in 96 well plates. The plates were cultured for at least 1 week at 37° C. under 5% CO$_2$. 3 days prior to ELISA analysis the selection media was changed.

Primary culture supernatants were tested in ELISA against HER1 ECD and various scaffold proteins. The testing against the scaffold proteins was done to demonstrate that the selected clones are binding to the dimerization domain β-hairpin of native HER1 ECD. The testing against the control scaffolds TtSlyDcas and TgSlyDΔIF was done to show that the selected clones are binding the inserted HER1 derived sequence and not the scaffold backbone. For the ELISA screening an antigen down format was used. HER1 ECD was immobilized at a concentration of 1 μg/ml and the scaffold proteins TtSlyDcys-HER1, TgSlyDcys-Her1 and TtSlyDcas were immobilized at a concentration of 0.5 μg/ml. Hybridoma Supernatant was added to the plates and incubated for 1 h at room temperature. Bound antibody was detected with a Horse radish peroxidase (HRP)-labeled F(ab')$_2$ goat anti-mouse Fcγ (Dianova) and 2,2'-Azino-di-[3-ethylbenzthiazoline sulfonate (6)] diammonium salt (ABTS) (Roche) was used as a HRP-substrate.

HRP-labeled F(ab')$_2$ABTS (Roche) was used as a HRP-substrate.

TABLE 3

Evaluation of the selected clones by ELISA. The clones were tested against the scaffold proteins TtSlyDcys-HER1, TgSlyDcys-HER1 and the full length HER1 ECD to verify their HER1 dimerization domain insert (β-Hairpin of HER1 (SEQ ID NO: 1)) specificity. As a negative control the scaffold protein TtSlyDcas was used.

| Clones | TtSlyDcas | TtSlyDcys-HER1 | TgSlyDcys-HER1 | HER1 ECD |
|---|---|---|---|---|
| M-31-22 | 0.034 | 3.091 | 2.930 | 3.065 |
| M-47-01 | 0.032 | 0.759 | 0.893 | 1.497 |
| M-47-04 | 0.044 | 0.493 | 0.803 | 1.275 |
| M-47-06 | 0.064 | 1.790 | 2.270 | 1.848 |
| M-47-08 | 0.020 | 0.327 | 1.265 | 0.839 |
| M-47-09 | 0.023 | 0.478 | 0.138 | 0.603 |
| M-47-12 | 0.028 | 0.482 | 0.208 | 1.373 |
| M-47-13 | 0.023 | 0.732 | 1.098 | 2.168 |
| M-46-14 | 0.033 | 1.050 | 1.416 | 2.878 |
| M-47-15 | 0.039 | 1.035 | 0.586 | 1.169 |
| M-47-16 | 0.020 | 0.967 | 0.434 | 1.037 |
| M-50-14 (=deposited MAK <HER1-DIB> M-50.097.14) | 0.029 | 2.875 | 2.362 | 2.520 |
| M-50-21 | 0.032 | 2.061 | 1.099 | 1.039 |
| M-50-23 (=deposited MAK <HER1-DIB> M-50.110.23) | 0.019 | 1.470 | 1.478 | 1.180 |
| M-50-24 | 0.025 | 2.395 | 2.155 | 1.350 |
| M-50-37 | 0.030 | 2.778 | 2.527 | 2.101 |
| M-50-38 | 0.034 | 2.349 | 1.946 | 1.932 |
| M-50-40 | 0.033 | 2.136 | 1.604 | 1.896 | c) Immunohistochemistry

Figure 5:
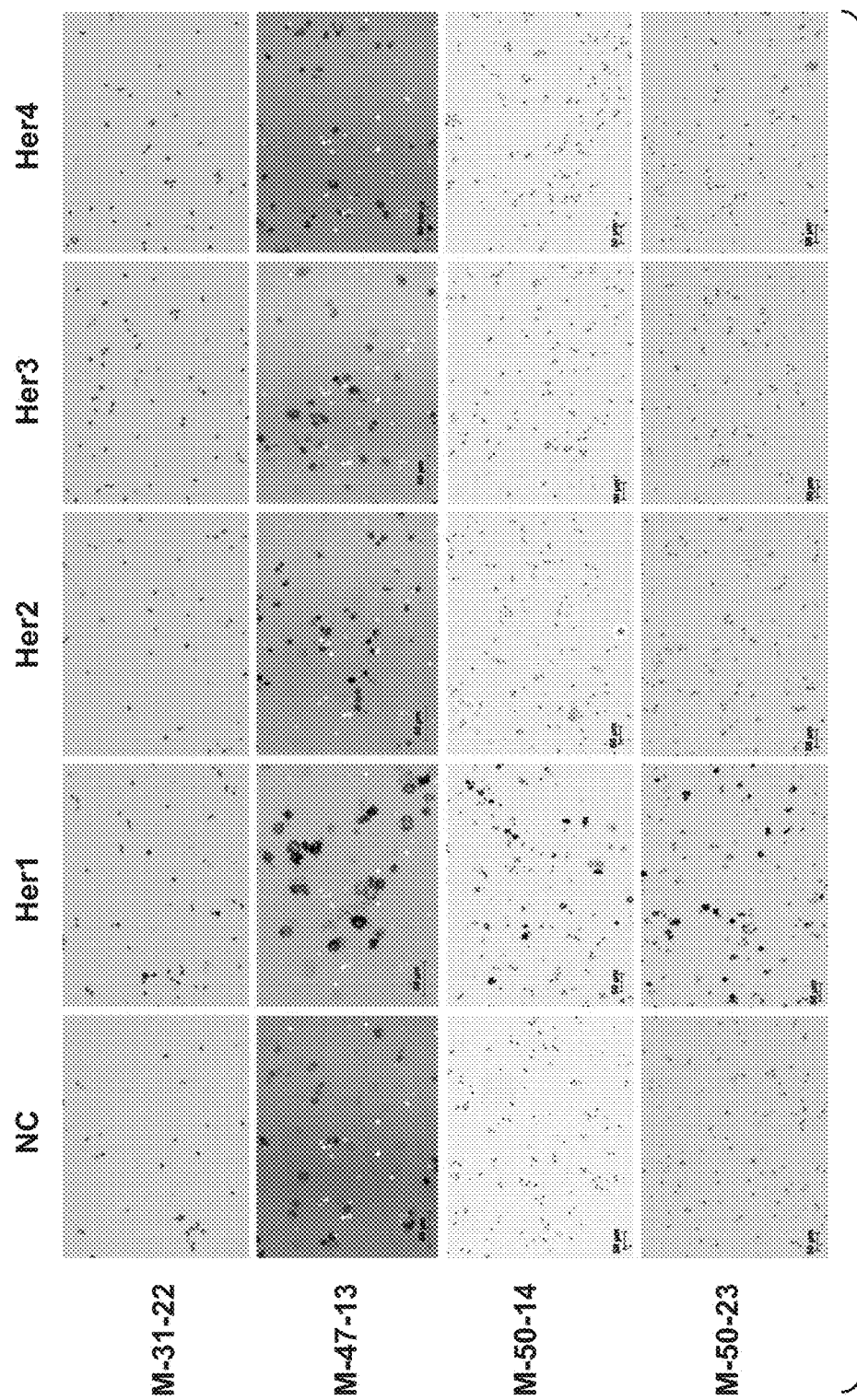

Selected clones were tested for reactivity and specificity in IHC. Therefore HEK293 cells were transiently transfected with plasmids coding for full length HER1, HER2, HER3 or HER4, respectively. 2 days after transfection the different cell lines now expressing HER1, HER2, HER3 or HER4 were harvested, subsequently fixed in formalin and embedded in Agarose for generation of IHC controls. After an additional fixation in formalin overnight the Agarose blocks were embedded in paraffin. Untransfected HEK293 cells were used as negative controls and treated accordingly to the transfected cells. After paraffin embedding 3 µm thin sections were prepared using a microtome. The sections were mounted on glass microscopy slides and dried for 2 h. All further steps of the immunohistochemical staining procedure were carried out using a Ventana Benchmark XT. The slides were dewaxed and antigen retrieval was performed by applying heat for 1 hour. For antigen retrieval the Ventana buffer CC1 was used. The antibodies were used at a concentration of 1 µg/ml. For the detection of bound antibody the Ventana UltraView detection kit was used. Results are shown in FIG. 5. All tested clones showed binding to HER1 and no cross reactivity against HER2, HER3 or HER4 was detectable.

d) DNA Sequencing of Selected Anti-Her1 Hybridoma

To obtain the DNA sequences of the selected hybridoma clones a 5' Race PCR was conducted. For the RT-PCR total RNA are prepared from $5 \times 10^6$ cells by using a total RNA purification kit (Qiagen). The reverse transcription and the PCR were conducted using a 5'prime RACE PCR kit (Roche). The resulting PCR fragments from heavy and light chain are purified by gel electrophoresis and subsequent gel purification. The PCR fragments are cloned using the Topo Zero-Blunt cloning kit (Invitrogen) and transformed into competent cells. Several clones from each hybridoma (e.g Clones M-31-22, M-37.058.09 (MAK <HER1-DIB> M-37.058.09 (DSM ACC3238)), M-37-15 (MAK <HER1-DIB> M-37.186.15 (DSM ACC3239)), M-47-01, M-47-04, M-47-06, M-47-08, M-47-09, M-47-12, M-47-13, M-46-14, M-47-15, M-47-16, M-50-14 (MAK <HER1-DIB> M-50.097.14 (DSM ACC3240)), M-50-21, M-50-23 (MAK <HER1-DIB> M-50.110.23 (DSM ACC3241)), M-50-24, M-50-37, M-50-38 and M-50-40) are submitted for sequencing to obtain a consensus sequences for the selected clones.

Example 3

Figure 6:
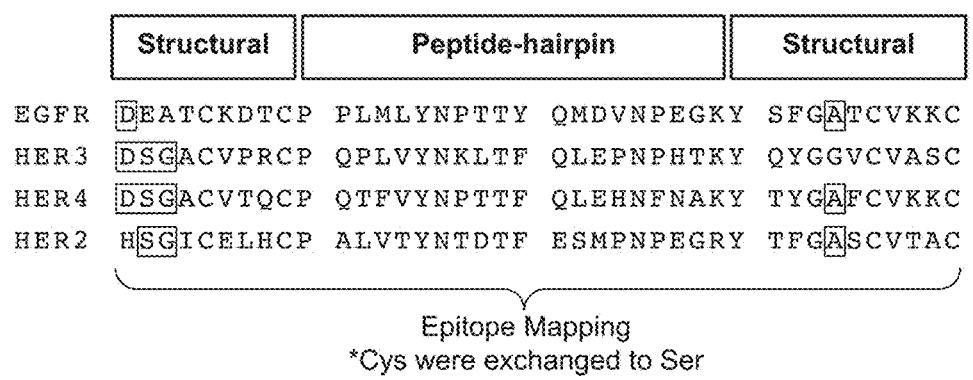

Exemplary Epitope Mapping of an Anti-HER1 Antibody (M-47-13) Peptide-Based 2D Epitope Mapping In another embodiment a peptide-based epitope mapping experiment was done to characterize the HER1 ECD epitopes by using the CelluSpots™ Synthesis and Epitope Mapping technology. Epitope mappings were carried out by means of a library of overlapping, immobilized peptide fragments (length: 15 amino acids) corresponding to the sequences of human HER1 ECD, HER2 ECD, HER3 ECD and HER4 ECD peptide hairpins. In FIG. 6, the strategy of the epitope mapping is shown. The peptide hairpin sequences (β-hairpin) of HER1(EGFR) ECD, HER2 ECD, HER3 ECD and HER4 ECD including their structural embeddings (structural) were investigated. Cysteines were replaced by serines. Each peptide synthesized was shifted by one amino acid, i.e. it had 14 amino acids overlap with the previous and the following peptide, respectively. For preparation of the peptide arrays the Intavis CelluSpots™ technology was employed. In this approach, peptides are synthesized with an automated synthesizer (Intavis MultiPep RS) on modified cellulose disks which are dissolved after synthesis. The solutions of individual peptides covalently linked to macromolecular cellulose are then spotted onto coated microscope slides. The CelluSpots™ synthesis was carried out stepwise utilizing 9-fluorenylmethoxycarbonyl (Fmoc) chemistry on amino-modified cellulose disks in a 384-well synthesis plate. In each coupling cycle, the corresponding amino acids were activated with a solution of DIC/HOBt in DMF. Between coupling steps un-reacted amino groups were capped with a mixture of acetic anhydride, diisopropylethyl amine and 1-hydroxybenzotriazole. Upon completion of the synthesis, the cellulose disks were transferred to a 96-well plate and treated with a mixture of trifluoroacetic acid (TFA), dichloromethane, triisoproylsilane (TIS) and water for side chain deprotection. After removal of the cleavage solution, the cellulose bound peptides are dissolved with a mixture of TFA, TFMSA, TIS and water, precipitated with diisopropyl ether and re-suspended in DMSO. The peptide solutions were subsequently spotted onto Intavis CelluSpots™ slides using an Intavis slide spotting robot.

For epitope analysis, the slides prepared as described above were washed with ethanol and then with Tris-buffered saline (TBS; 50 mM Tris, 137 mM NaCl, 2.7 mM KCl, pH 8) before blocking for 16 h at 4° C. with 5 mL 10× Western Blocking Reagent (Roche Applied Science), 2.5 g sucrose in TBS, 0.1% Tween 20. The slide was washed with TBS and 0.1% Tween 20 and incubated afterward with 1 µg/mL of the corresponding IGF1 antibodies in TBS and 0.1% Tween 20 at ambient temperature for 2 h and subsequently washed with TBS+0.1% Tween 20. For detection, the slide was incubated with anti-rabbit/anti-mouse secondary HRP-antibody (1:20000 in TBS-T) followed by incubation with chemiluminescence substrate luminol and visualized with a Lumilmager (Roche Applied Science). ELISA-positive SPOTs were quantified and through assignment of the corresponding peptide sequences the antibody binding epitopes were identified.

Figure 7:
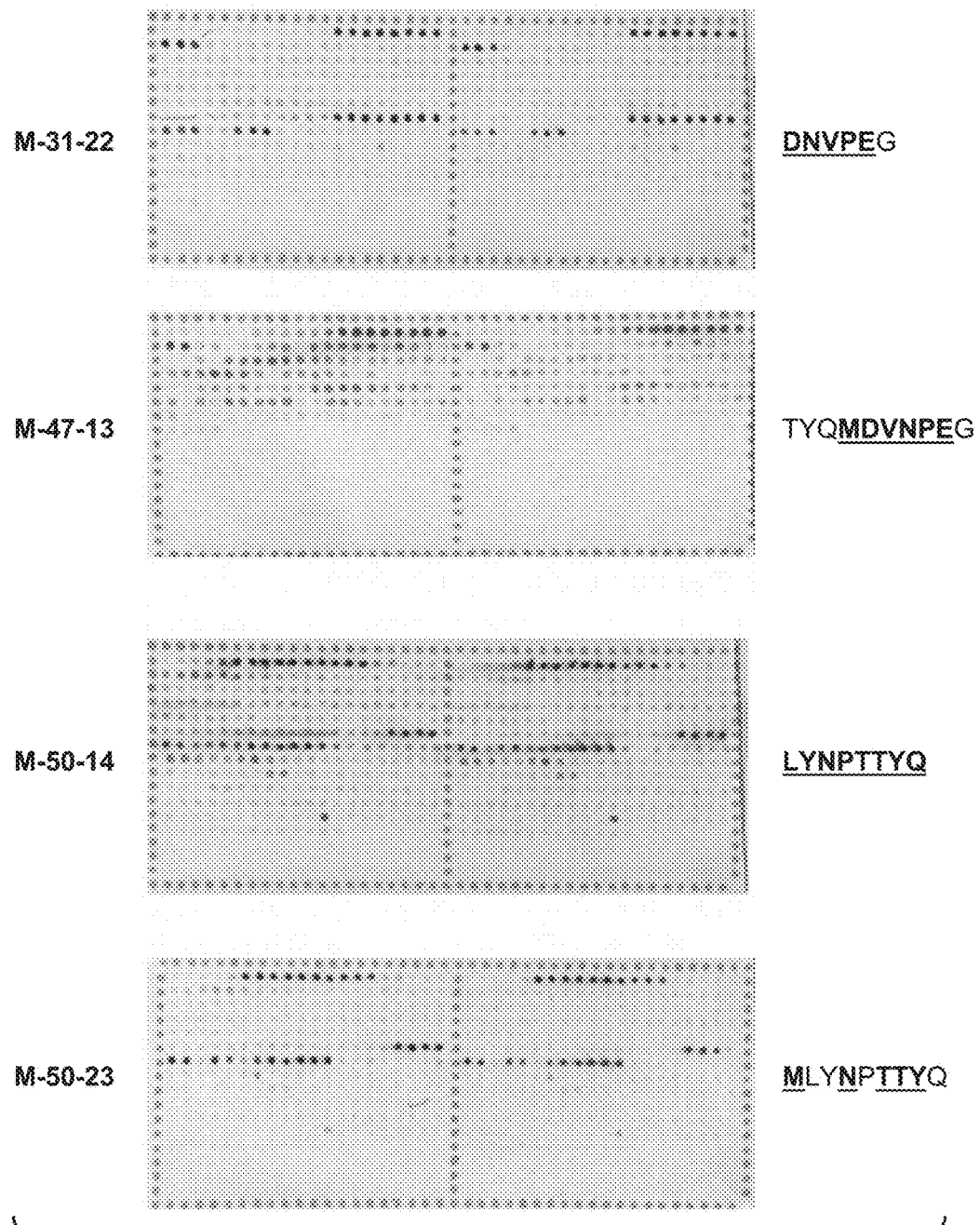

As depicted in FIG. 7, M-47-13 shows a HER1 ECD epitope with the amino acid sequence TYQMDVNPEG (SEQ ID NO: 19) with no detectable signals versus the hairpin motives in the HER2 ECD, the HER3 ECD or the HER4 ECD M31-22 shows a slightly different epitope. M-50-14 (deposited MAK <HER1-DIB> M-50.097.14 (DSM ACC3240)) and M-50-23 (deposited MAK <HER1-DIB> M-50.110.23 (DSM ACC3241)) show a HER1 ECD epitope with the amino acid sequence MLYNPTTYQ (SEQ ID NO:20) with no detectable signals versus the hairpin motives in the HER2 ECD, the HER3 ECD or the HER4 ECD.

Example 4

Kinetic Screening/Binding Properties of Anti-HER1 β-Hairpin Antibodies

The kinetic screening is performed according to Schraeml et al. (Schraml, M. and M. Biehl, Methods Mol Biol 901 (2012) 171-181) on a BIAcore 4000 instrument, mounted with a Biacore CM5 sensor. In all assay the test antibodies are captured. The system is under the control of the software version V1.1. The instrument buffer was HBS-EP (10 mM HEPES (pH 7.4), 150 mM NaCl, 1 mM EDTA, 0.05% (w/v) P20). The system is operated at 25° C. 30 µg/ml Rabbit polyclonal antibody (RAM IgG, (Rabbit anti Mouse IgG with Fc gamma specificity) GE Healthcare) in 10 mM sodium acetate buffer (pH 4.5) is immobilized using EDC/NHS chemistry according to the manufacturer's instructions on the spots 1, 2, 4 and 5 in the flow cells 1, 2, 3 and 4. The sensor is saturated using 1M ethanolamine. In each flow cell, referenced signals are calculated using spots 1-2 and spots 5-4, spot 3 served as a blanc control. The antigen (human recombinant HER1 ECD, and one of the recombinant *Thermus thermophilus* TtSlyDcas-HER1, TtSlyDcys-HER1, TtSlyD(GSG)-HER1, TtSlyD(CC)-HER1, TtSlyD(SS)-HER1, *Thermococcus gammatolerans* TgSlyDcys-HER1 comprising the β-hairpin peptide of HER1 (SEQ ID NO:1)) is diluted at 150 nM in instrument buffer supplemented with 1 mg/ml CMD (Carboxymethyldextran, Sigma). to suppress unspecific binding. Prior to their application the hybridoma culture supernatants are diluted 1:5 in instrument buffer. The diluted mixtures are injected at a flow rate of 30 µl/min for 2 min. The antibody capture level (CL) in response units is monitored. Immediately thereafter the respective antigen is injected at a flow rate of 30 µl/min for 3 min association time. Thereafter, the antibody-antigen complex dissociation signal is recorded for 5 min. The sensor is regenerated by injecting a 10 mM glycine-HCl solution (pH 1.7) for 2 min at a flow rate of 30 µl/min. The recorded signal shortly before the end of the injection of the antigen is denoted as binding late (BL) in response units. The recorded signal shortly before the end of the recording of the dissociation is denoted as stability late (SL) in response units. The dissociation rate constants are determined calculated The antibody-antigen complex stability in minutes is calculated with the following formula: ln(2)/60*kd. The Molar Ratio was calculated with the formula: MW (antibody)/MW (antigen) *BL (antigen)/CL (antibody).

Binding Late (BL) represents the response units at the end of the analyte injection. The amount of antibody captured as a ligand on the sensor surface is measured as Capture Level (CL) in response units. Together with the information of the molecular weights of the tested analytes, the antibody and the analyte in solution, the Molar Ratio can be calculated. In case the sensor is configured with a suitable amount of antibody ligand capture level, each antibody should be able to functionally bind at least to one analyte in solution, which is represented by a Molar Ratio of MR=1.0. Then, the Molar Ratio is also an indicator for the valence mode of analyte binding. The maximum valence can be MR=2 for an antibody binding two analytes, one with each Fab valence. In case of steric limitations or a dysfunctional analyte binding, the Molar Ratio can indicate understoichiometric binding, like it is the case when the HER1 ECD is being bound in its "closed" conformation by the anti HER1 β-hairpin antibodies of the invention (as this B hairpin is hidden in the closed conformation. The maximum assay deviation in the determination of the Molar Ratio is MR=0.2.

Example 5

Time Dependent Internalization Analyses of Anti-HER1 β-Hairpin Antibodies Via Western Blot!

Binding of anti-HER1 β-hairpin antibodies to and internalization of anti-HER1 β-hairpin antibodies was analyzed in Western Blot using the HER1 expressing cancer cell line A549.

HER1 expressing A549 (ATCC® CCL-185™ lung carcinoma) cells were seeded into 24-well-plates (3×105 cells/well, media containing 10% FCS). On the next day the media was replaced by starving media (0.5% FCS). Four hours later (24 hours before cell lysis), antibody M-50-14 (=deposited MAK <HER1-DIB> M-50.097.14) was added to two wells of each cell line to a final concentration of 185 µg/ml. On the next day antibody M-50-14 (=deposited MAK <HER1-DIB> M-50.097.14) was added again at the following times: cell lysis minus 6 hours, minus 4 hours, minus 2 hours, minus 1 hour. Ten minutes before cell lysis one well of each time point was stimulated with hEGF (final concentration 200 ng/ml). The cells were lysed with 40 µl Triton Lysis Buffer. SDS-PAGE was performed, followed by semi-dry Western Blotting. The membranes were incubated with antibodies against HER1 (Upstate #06-847), PhosphoHER1 (Epitomics #1139-1) and Phosphotyrosine (Millipore #16-105).

Figure 9:
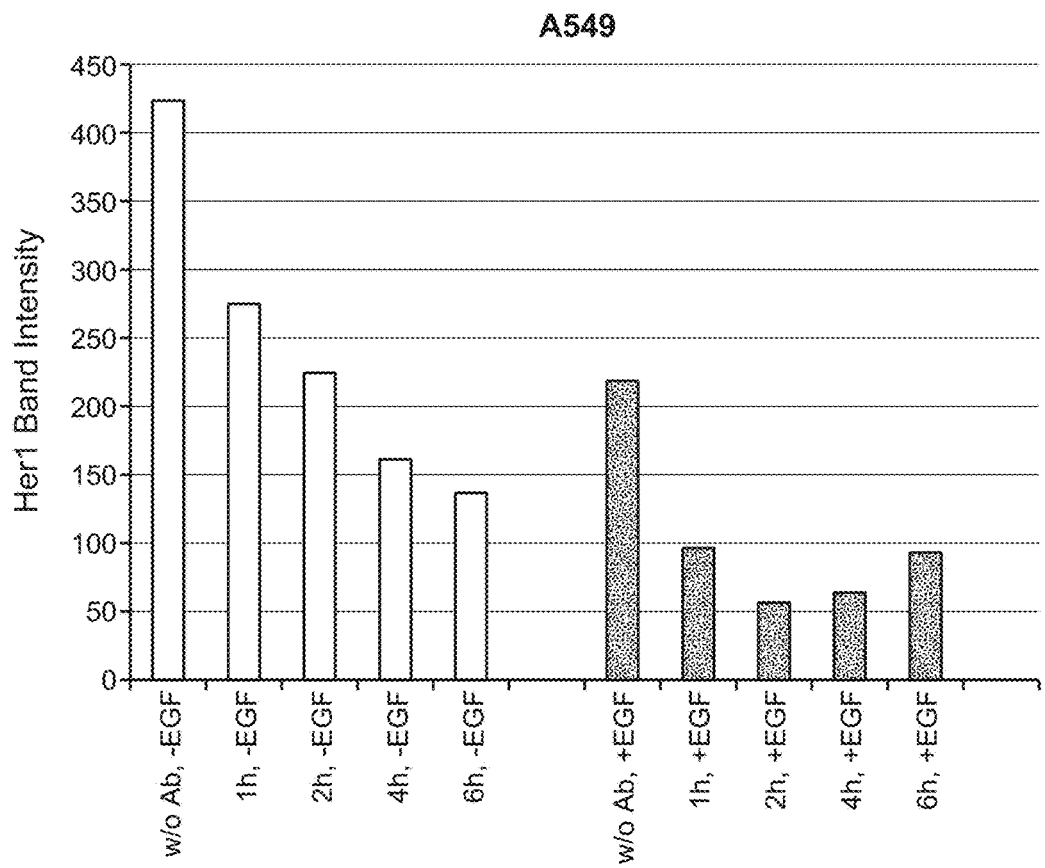

Results are shown in FIG. 9 (A549 cells) Left side shows time dependent HER1 detection in the absence of EGF, right side shows time dependent HER1 detection in the presence of EGF. Antibody M-50-14 shows a clearly stronger HER1 internalization in the presence than in the absence of EGF. (more than 70 percent internalization of HER1 in the presence of EGF after 2 h after incubation with the antibody in a Western Blot assay with HER1 expressing A549 cells and less than 55 percent internalization of HER1 in the absence of EGF after 2 h after incubation with the antibody in a Western Blot assay with HER1 expressing A549 cells).

Example 6

Inhibition (No Induction of) HER1 Phosphorylation by antiHER1 Antibody Binding in HER1 Expressing A549 and A431 Cancer Cells HER1 expressing A549 (ATCC® CCL-185™ lung carcinoma) cells and A431 (ATCC® CRL-1555™—skin cancer/epidermoid carcinoma) cells were seeded into 24-well-plates (3×105 cells/well, media containing 10% FCS). On the next day the media was replaced by starving media (0.5% FCS). Four hours later (24 hours before cell lysis), antibody was added to two wells of each cell line to a final concentration of 185 µg/ml. On the next day antibody was added again at the following times: cell lysis minus 6 hours, minus 4 hours, minus 2 hours, minus 1 hour. Ten minutes before cell lysis one well of each time point was stimulated with hEGF (final concentration 200 ng/ml). The cells were lysed with 40 µl Triton Lysis Buffer. SDS-PAGE was performed, followed by semi-dry Western Blotting. The membranes were incubated with antibodies against HER1 (Upstate #06-847), PhosphoHER1 (Epitomics #1139-1) and Phosphotyrosine (Millipore #16-105).

Figure 8A:
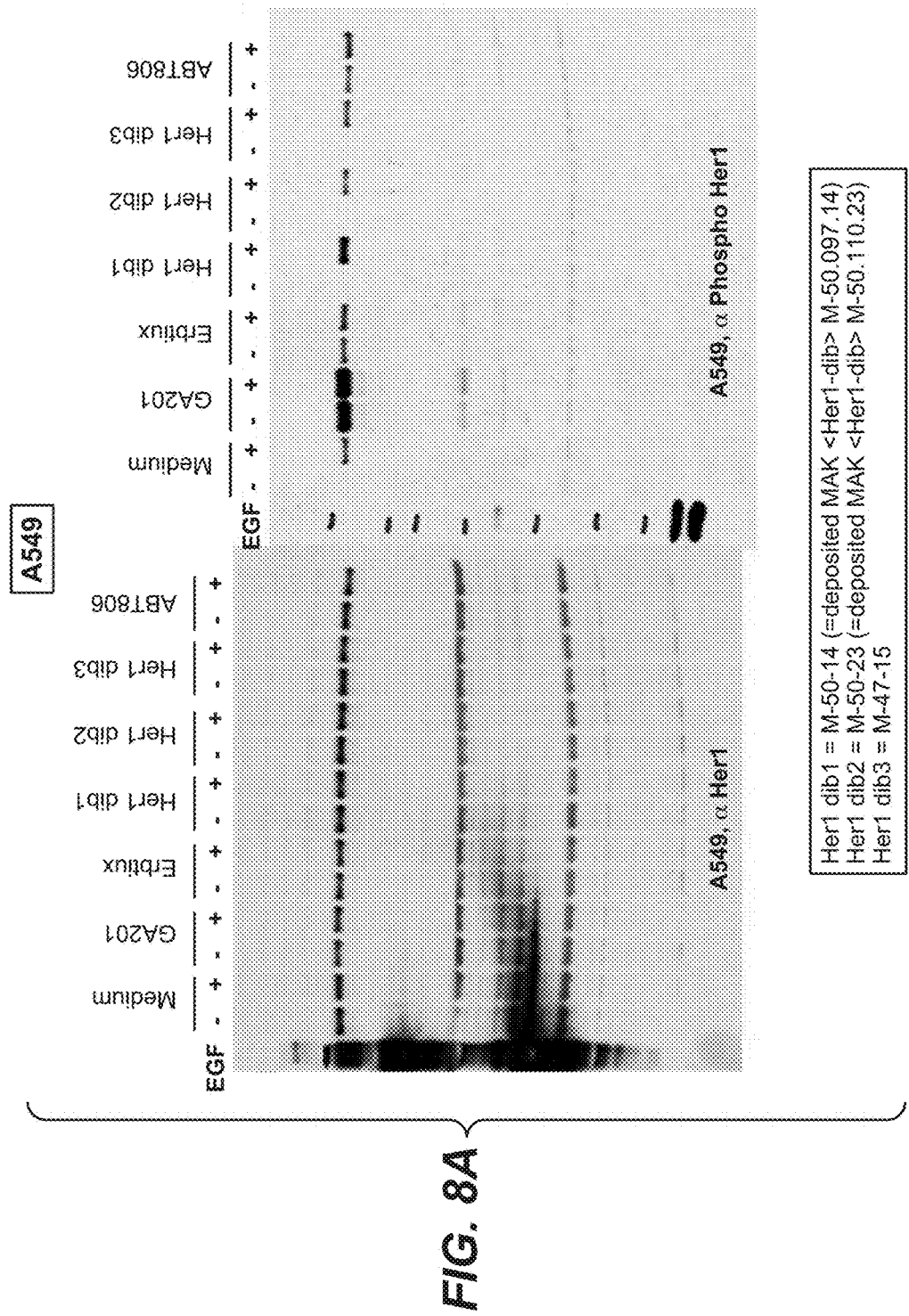
Figure 8B:
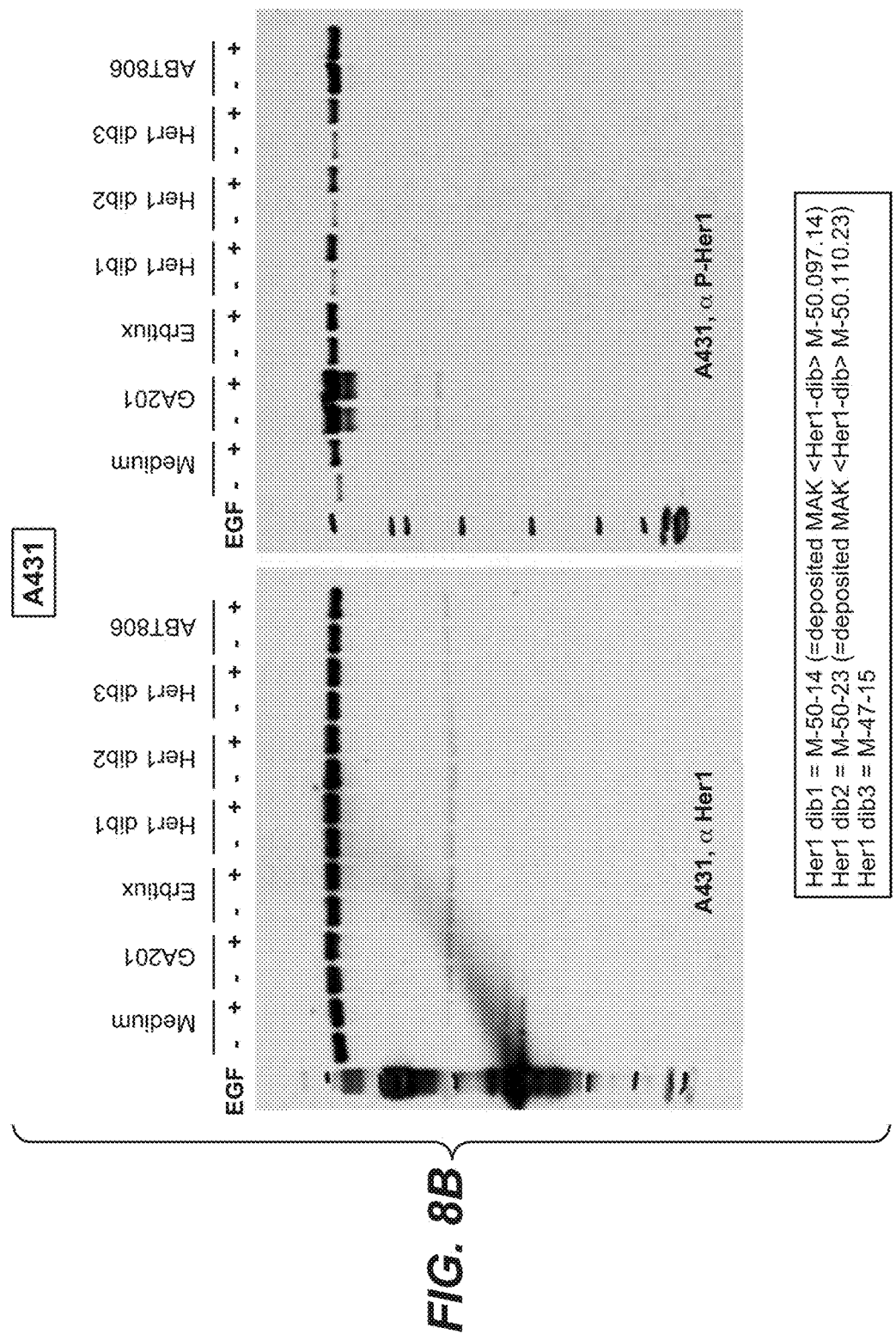

Results are shown in FIGS. 8A (A549 cells) and 8B (A431 cells, strong HER1 expression with slight constitutively activated/phosphorylated HER1). Left lane shows HER1 detection, right lane the phosphorylated HER1 detection in the absence or presence of EGF In both cancer cell lines the anti-HER1 β-hairpin antibodies HER1 dib1=M-50-14 (=deposited MAK <HER1-DIB> M-50.097.14 ((DSM ACC3240)), HER1 dib2=M-50-23 (=deposited MAK <HER1-DIB> M-50.110.23 (DSM ACC3241)) and HER1 dib3=M-47-15 show no induction of phosphorylation and act as non-agonistic HER1 antibodies (in the absence of EGF ligand, -lane), while other HER1 antibodies like cetuximab, GA201 (imgatuzumab, CAS number 959963-46-3 a humanized, glycoengineered IgG1 mAb derived by humanization of the parental ICR62 rat antibody, described e.g. in WO 2006/082515), or ABT806 (mAb806, targets the EGFR deletion variant, de2-7 EGFR as well as wild-type, described e.g in US2011/0076232) were induced strong phosphorylation (in the absence of EGF, compared to medium without antibody or to the antibodies of the present invention).

Example 7

Binding of Ligand EGF to HER1(EGFR)-ECD in the Presence of Anti-HER1 β-Hairpin Antibodies (ELISA)

A Streptavidin-coated 96-well plate was incubated at 4° C. with cell culture supernatant containing SBP-tagged HER1-ECD. On the next day the wells were washed three times with washing buffer (PBS+0.05% Tween-20) and blocked with PBS containing 1% BSA for one hour. After another three washes with washing buffer, 40 µl antibody solution (in Delfia Binding Buffer) was added to each well as a 2× stock of the desired final concentrations ($10^{-3}$ to $10^3$ nM). Immediately 40 µl of 20 nM Europium-labeled EGF was added to achieve a final concentration of 10 nM. The plates were incubated on a shaker at room temperature for two hours. Following three washes with Delfia Wash Buffer, Delfia Enhancement Solution was added and incubated on a shaker for 15 minutes (light protected). Finally, the plates were measured in a Tecan Infinite F200 reader using a time-resolved fluorescence measurement protocol. The HER1dib-supernatants were used in dilutions from 1:1 to 1:10e7. Results for anti-HER1 antibodies M-50-14 (50.097.14=MAK <HER1-DIB> M-50.097.14 (DSM ACC3240); M-50-23 (50.110.23=MAK <HER1-DIB> M-50.110.23 (DSM ACC3241); M-47-15 (M-47.259.15); M-31-22 (M-31.021.22); M-37-09 (MAK <HER1-DIB> M-37.058.09 (DSM ACC3238); M-37-15 (MAK <HER1-DIB> M-37.186.15 (DSM ACC3239) are shown in FIG. 10.

What is claimed is:

1. An isolated antibody that binds to human HER1, wherein the antibody comprises
   i) (a) HVR-H1; (b) HVR-H2; (c) HVR-H3; (d) HVR-L1; (e) HVR-L2; and (f) HVR-L3 of deposited antibody MAK <HER1-DIB> M-50.097.14 (DSM ACC3240);
   ii) (a) HVR-H1; (b) HVR-H2; (c) HVR-H3; (d) HVR-L1; (e) HVR-L2; and (f) HVR-L3 of deposited antibody MAK <HER1-DIB>M-50.110.23(DSM ACC3241);
   iii) (a) HVR-H1; (b) HVR-H2; (c) HVR-H3; (d) HVR-L1; (e) HVR-L2; and (f) HVR-L3 of deposited antibody MAK <HER1-DIB> M-37.058.09 (DSM ACC3238); or
   iv) (a) HVR-H1; (b) HVR-H2; (c) HVR-H3; (d) HVR-L1; (e) HVR-L2; and (f) HVR-L3 of deposited antibody MAK <HER1-DIB> M-37.186.15 (DSM ACC3239);
   wherein the all HVRs are determined according to Kabat.

2. The antibody of claim 1, which is a full length IgG1 antibody or IgG4 antibody.

3. The antibody of claim 1, which is a Fab fragment.

4. An immunoconjugate comprising the antibody of claim 1 and a cytotoxic agent.

5. A pharmaceutical formulation comprising the antibody of claim 1, and a pharmaceutically acceptable carrier.

6. The antibody claim 1, wherein the antibody comprises
   i) (a) HVR-H1; (b) HVR-H2; (c) HVR-H3; (d) HVR-L1; (e) HVR-L2; and (f) HVR-L3 of deposited antibody MAK <HER1-DIB> M-50.097.14 (DSM ACC3240); or
   ii) (a) HVR-H1; (b) HVR-H2; (c) HVR-H3; (d) HVR-L1; (e) HVR-L2; and (f) HVR-L3 of deposited antibody MAK <HER1-DIB>M-50.110.23(DSM ACC3241).

7. The antibody of claim 6, which is a full length IgG1 antibody or IgG4 antibody.

8. The antibody of claim 6, which is a Fab fragment.

9. An immunoconjugate comprising the antibody of claim 6 and a cytotoxic agent.

10. A pharmaceutical formulation comprising the antibody of claim 6, and a pharmaceutically acceptable carrier.

11. The antibody of claim 1 or claim 6 which is a humanized or chimeric antibody.

12. The antibody of claim 1 or claim 6, wherein the antibody does not induce phosphorylation of HER1 in A549 cancer cells in the absence of EGF.

13. The antibody of claim 1 or claim 6 wherein the antibody inhibits dimerization of HER1/HER2.

14. The antibody of claim 1 or claim 6 wherein the antibody inhibits dimerization of HER1/HER1.

* * * * *

```
                         SEQUENCE LISTING

<160> NUMBER OF SEQ ID NOS: 26

<210> SEQ ID NO 1
<211> LENGTH: 20
<212> TYPE: PRT
<213> ORGANISM: Homo Sapiens

<400> SEQUENCE: 1

Pro Pro Leu Met Leu Tyr Asn Pro Thr Thr Tyr Gln Met Asp Val Asn
1               5                   10                  15

Pro Glu Gly Lys
            20

<210> SEQ ID NO 2
<211> LENGTH: 1186
<212> TYPE: PRT
<213> ORGANISM: Homo Sapiens

<400> SEQUENCE: 2

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
                20                  25                  30

Asn Cys Glu Val Val Leu Gly Asn Leu Glu Ile Thr Tyr Val Gln Arg
            35                  40                  45

Asn Tyr Asp Leu Ser Phe Leu Lys Thr Ile Gln Glu Val Ala Gly Tyr
        50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205
```

```
His Asn Gln Cys Ala Ala Gly Cys Thr Gly Pro Arg Glu Ser Asp Cys
    210                 215                 220
Leu Val Cys Arg Lys Phe Arg Asp Glu Ala Thr Cys Lys Asp Thr Cys
225                 230                 235                 240
Pro Pro Leu Met Leu Tyr Asn Pro Thr Thr Tyr Gln Met Asp Val Asn
                245                 250                 255
Pro Glu Gly Lys Tyr Ser Phe Gly Ala Thr Cys Val Lys Lys Cys Pro
                260                 265                 270
Arg Asn Tyr Val Val Thr Asp His Gly Ser Cys Val Arg Ala Cys Gly
            275                 280                 285
Ala Asp Ser Tyr Glu Met Glu Glu Asp Gly Val Arg Lys Cys Lys Lys
    290                 295                 300
Cys Glu Gly Pro Cys Arg Lys Val Cys Asn Gly Ile Gly Ile Gly Glu
305                 310                 315                 320
Phe Lys Asp Ser Leu Ser Ile Asn Ala Thr Asn Ile Lys His Phe Lys
                325                 330                 335
Asn Cys Thr Ser Ile Ser Gly Asp Leu His Ile Leu Pro Val Ala Phe
                340                 345                 350
Arg Gly Asp Ser Phe Thr His Thr Pro Pro Leu Asp Pro Gln Glu Leu
            355                 360                 365
Asp Ile Leu Lys Thr Val Lys Glu Ile Thr Gly Phe Leu Leu Ile Gln
    370                 375                 380
Ala Trp Pro Glu Asn Arg Thr Asp Leu His Ala Phe Glu Asn Leu Glu
385                 390                 395                 400
Ile Ile Arg Gly Arg Thr Lys Gln His Gly Gln Phe Ser Leu Ala Val
                405                 410                 415
Val Ser Leu Asn Ile Thr Ser Leu Gly Leu Arg Ser Leu Lys Glu Ile
                420                 425                 430
Ser Asp Gly Asp Val Ile Ile Ser Gly Asn Lys Asn Leu Cys Tyr Ala
            435                 440                 445
Asn Thr Ile Asn Trp Lys Lys Leu Phe Gly Thr Ser Gly Gln Lys Thr
    450                 455                 460
Lys Ile Ile Ser Asn Arg Gly Glu Asn Ser Cys Lys Ala Thr Gly Gln
465                 470                 475                 480
Val Cys His Ala Leu Cys Ser Pro Glu Gly Cys Trp Gly Pro Glu Pro
                485                 490                 495
Arg Asp Cys Val Ser Cys Arg Asn Val Ser Arg Gly Arg Glu Cys Val
                500                 505                 510
Asp Lys Cys Asn Leu Leu Glu Gly Glu Pro Arg Glu Phe Val Glu Asn
            515                 520                 525
Ser Glu Cys Ile Gln Cys His Pro Glu Cys Leu Pro Gln Ala Met Asn
    530                 535                 540
Ile Thr Cys Thr Gly Arg Gly Pro Asp Asn Cys Ile Gln Cys Ala His
545                 550                 555                 560
Tyr Ile Asp Gly Pro His Cys Val Lys Thr Cys Pro Ala Gly Val Met
                565                 570                 575
Gly Glu Asn Asn Thr Leu Val Trp Lys Tyr Ala Asp Ala Gly His Val
                580                 585                 590
Cys His Leu Cys His Pro Asn Cys Thr Tyr Gly Cys Thr Gly Pro Gly
            595                 600                 605
Leu Glu Gly Cys Pro Thr Asn Gly Pro Lys Ile Pro Ser Ile Ala Thr
    610                 615                 620
Gly Met Val Gly Ala Leu Leu Leu Leu Leu Val Val Ala Leu Gly Ile
```

-continued

```
        625                 630                 635                 640
Gly Leu Phe Met Arg Arg His Ile Val Arg Lys Arg Thr Leu Arg
                645                 650                 655
Arg Leu Leu Gln Glu Arg Glu Leu Val Glu Pro Leu Thr Pro Ser Gly
                660                 665                 670
Glu Ala Pro Asn Gln Ala Leu Leu Arg Ile Leu Lys Glu Thr Glu Phe
                675                 680                 685
Lys Lys Ile Lys Val Leu Gly Ser Gly Ala Phe Gly Thr Val Tyr Lys
                690                 695                 700
Gly Leu Trp Ile Pro Glu Gly Glu Lys Val Lys Ile Pro Val Ala Ile
705                 710                 715                 720
Lys Glu Leu Arg Glu Ala Thr Ser Pro Lys Ala Asn Lys Glu Ile Leu
                725                 730                 735
Asp Glu Ala Tyr Val Met Ala Ser Val Asp Asn Pro His Val Cys Arg
                740                 745                 750
Leu Leu Gly Ile Cys Leu Thr Ser Thr Val Gln Leu Ile Thr Gln Leu
                755                 760                 765
Met Pro Phe Gly Cys Leu Leu Asp Tyr Val Arg Glu His Lys Asp Asn
                770                 775                 780
Ile Gly Ser Gln Tyr Leu Leu Asn Trp Cys Val Gln Ile Ala Lys Gly
785                 790                 795                 800
Met Asn Tyr Leu Glu Asp Arg Arg Leu Val His Arg Asp Leu Ala Ala
                805                 810                 815
Arg Asn Val Leu Val Lys Thr Pro Gln His Val Lys Ile Thr Asp Phe
                820                 825                 830
Gly Leu Ala Lys Leu Leu Gly Ala Glu Glu Lys Glu Tyr His Ala Glu
                835                 840                 845
Gly Gly Lys Val Pro Ile Lys Trp Met Ala Leu Glu Ser Ile Leu His
                850                 855                 860
Arg Ile Tyr Thr His Gln Ser Asp Val Trp Ser Tyr Gly Val Thr Val
865                 870                 875                 880
Trp Glu Leu Met Thr Phe Gly Ser Lys Pro Tyr Asp Gly Ile Pro Ala
                885                 890                 895
Ser Glu Ile Ser Ser Ile Leu Glu Lys Gly Glu Arg Leu Pro Gln Pro
                900                 905                 910
Pro Ile Cys Thr Ile Asp Val Tyr Met Ile Met Val Lys Cys Trp Met
                915                 920                 925
Ile Asp Ala Asp Ser Arg Pro Lys Phe Arg Glu Leu Ile Ile Glu Phe
930                 935                 940
Ser Lys Met Ala Arg Asp Pro Gln Arg Tyr Leu Val Ile Gln Gly Asp
945                 950                 955                 960
Glu Arg Met His Leu Pro Ser Pro Thr Asp Ser Asn Phe Tyr Arg Ala
                965                 970                 975
Leu Met Asp Glu Glu Asp Met Asp Asp Val Val Asp Ala Asp Glu Tyr
                980                 985                 990
Leu Ile Pro Gln Gln Gly Phe Phe Ser Ser Pro Ser Thr Ser Arg Thr
                995                 1000                1005
Pro Leu Leu Ser Ser Leu Ser Ala Thr Ser Asn Asn Ser Thr Val
                1010                1015                1020
Ala Cys Ile Asp Arg Asn Gly Leu Gln Ser Cys Pro Ile Lys Glu
                1025                1030                1035
Asp Ser Phe Leu Gln Arg Tyr Ser Ser Asp Pro Thr Gly Ala Leu
                1040                1045                1050
```

```
Thr Glu Asp Ser Ile Asp Asp Thr Phe Leu Pro Val Pro Glu Tyr
    1055            1060                1065

Ile Asn Gln Ser Val Pro Lys Arg Pro Ala Gly Ser Val Gln Asn
    1070            1075                1080

Pro Val Tyr His Asn Gln Pro Leu Asn Pro Ala Pro Ser Arg Asp
    1085            1090                1095

Pro His Tyr Gln Asp Pro His Ser Thr Ala Val Gly Asn Pro Glu
    1100            1105                1110

Tyr Leu Asn Thr Val Gln Pro Thr Cys Val Asn Ser Thr Phe Asp
    1115            1120                1125

Ser Pro Ala His Trp Ala Gln Lys Gly Ser His Gln Ile Ser Leu
    1130            1135                1140

Asp Asn Pro Asp Tyr Gln Gln Asp Phe Phe Pro Lys Glu Ala Lys
    1145            1150                1155

Pro Asn Gly Ile Phe Lys Gly Ser Thr Ala Glu Asn Ala Glu Tyr
    1160            1165                1170

Leu Arg Val Ala Pro Gln Ser Ser Glu Phe Ile Gly Ala
    1175            1180                1185

<210> SEQ ID NO 3
<211> LENGTH: 621
<212> TYPE: PRT
<213> ORGANISM: Homo Sapiens

<400> SEQUENCE: 3

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
```

-continued

```
            225                 230                 235                 240
Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
        355                 360                 365

Asp Ile Leu Lys Thr Val Lys Glu Ile Thr Gly Phe Leu Leu Ile Gln
    370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
        435                 440                 445

Asn Thr Ile Asn Trp Lys Lys Leu Phe Gly Thr Ser Gly Gln Lys Thr
    450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
        515                 520                 525

Ser Glu Cys Ile Gln Cys His Pro Glu Cys Leu Pro Gln Ala Met Asn
    530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
        595                 600                 605

Leu Glu Gly Cys Pro Thr Asn Gly Pro Lys Ile Pro Ser
    610                 615                 620

<210> SEQ ID NO 4
<211> LENGTH: 1185
<212> TYPE: PRT
<213> ORGANISM: Homo Sapiens
```

<400> SEQUENCE: 4

```
Pro Gln His Trp Ser Cys Pro Glu Gly Thr Leu Ala Gly Asn Gly Asn
1               5                   10                  15

Ser Thr Cys Val Gly Pro Ala Pro Phe Leu Ile Phe Ser His Gly Asn
            20                  25                  30

Ser Ile Phe Arg Ile Asp Thr Glu Gly Thr Asn Tyr Glu Gln Leu Val
                35                  40                  45

Val Asp Ala Gly Val Ser Val Ile Met Asp Phe His Tyr Asn Glu Lys
    50                  55                  60

Arg Ile Tyr Trp Val Asp Leu Glu Arg Gln Leu Leu Gln Arg Val Phe
65                  70                  75                  80

Leu Asn Gly Ser Arg Gln Glu Arg Val Cys Asn Ile Glu Lys Asn Val
                85                  90                  95

Ser Gly Met Ala Ile Asn Trp Ile Asn Glu Glu Val Ile Trp Ser Asn
            100                 105                 110

Gln Gln Glu Gly Ile Ile Thr Val Thr Asp Met Lys Gly Asn Asn Ser
        115                 120                 125

His Ile Leu Leu Ser Ala Leu Lys Tyr Pro Ala Asn Val Ala Val Asp
130                 135                 140

Pro Val Glu Arg Phe Ile Phe Trp Ser Ser Glu Val Ala Gly Ser Leu
145                 150                 155                 160

Tyr Arg Ala Asp Leu Asp Gly Val Gly Val Lys Ala Leu Leu Glu Thr
                165                 170                 175

Ser Glu Lys Ile Thr Ala Val Ser Leu Asp Val Leu Asp Lys Arg Leu
            180                 185                 190

Phe Trp Ile Gln Tyr Asn Arg Glu Gly Ser Asn Ser Leu Ile Cys Ser
        195                 200                 205

Cys Asp Tyr Asp Gly Gly Ser Val His Ile Ser Lys His Pro Thr Gln
210                 215                 220

His Asn Leu Phe Ala Met Ser Leu Phe Gly Asp Arg Ile Phe Tyr Ser
225                 230                 235                 240

Thr Trp Lys Met Lys Thr Ile Trp Ile Ala Asn Lys His Thr Gly Lys
                245                 250                 255

Asp Met Val Arg Ile Asn Leu His Ser Ser Phe Val Pro Leu Gly Glu
            260                 265                 270

Leu Lys Val Val His Pro Leu Ala Gln Pro Lys Ala Glu Asp Asp Thr
        275                 280                 285

Trp Glu Pro Glu Gln Lys Leu Cys Lys Leu Arg Lys Gly Asn Cys Ser
290                 295                 300

Ser Thr Val Cys Gly Gln Asp Leu Gln Ser His Leu Cys Met Cys Ala
305                 310                 315                 320

Glu Gly Tyr Ala Leu Ser Arg Asp Arg Lys Tyr Cys Glu Asp Val Asn
                325                 330                 335

Glu Cys Ala Phe Trp Asn His Gly Cys Thr Leu Gly Cys Lys Asn Thr
            340                 345                 350

Pro Gly Ser Tyr Tyr Cys Thr Cys Pro Val Gly Phe Val Leu Leu Pro
        355                 360                 365

Asp Gly Lys Arg Cys His Gln Leu Val Ser Cys Pro Arg Asn Val Ser
370                 375                 380

Glu Cys Ser His Asp Cys Val Leu Thr Ser Glu Gly Pro Leu Cys Phe
385                 390                 395                 400

Cys Pro Glu Gly Ser Val Leu Glu Arg Asp Gly Lys Thr Cys Ser Gly
```

```
                405                 410                 415
Cys Ser Ser Pro Asp Asn Gly Gly Cys Ser Gln Leu Cys Val Pro Leu
            420                 425                 430

Ser Pro Val Ser Trp Glu Cys Asp Cys Phe Pro Gly Tyr Asp Leu Gln
            435                 440                 445

Leu Asp Glu Lys Ser Cys Ala Ala Ser Gly Pro Gln Pro Phe Leu Leu
            450                 455                 460

Phe Ala Asn Ser Gln Asp Ile Arg His Met His Phe Asp Gly Thr Asp
465                 470                 475                 480

Tyr Gly Thr Leu Leu Ser Gln Gln Met Gly Met Val Tyr Ala Leu Asp
            485                 490                 495

His Asp Pro Val Glu Asn Lys Ile Tyr Phe Ala His Thr Ala Leu Lys
            500                 505                 510

Trp Ile Glu Arg Ala Asn Met Asp Gly Ser Gln Arg Glu Arg Leu Ile
            515                 520                 525

Glu Glu Gly Val Asp Val Pro Glu Gly Leu Ala Val Asp Trp Ile Gly
            530                 535                 540

Arg Arg Phe Tyr Trp Thr Asp Arg Gly Lys Ser Leu Ile Gly Arg Ser
545                 550                 555                 560

Asp Leu Asn Gly Lys Arg Ser Lys Ile Ile Thr Lys Glu Asn Ile Ser
                565                 570                 575

Gln Pro Arg Gly Ile Ala Val His Pro Met Ala Lys Arg Leu Phe Trp
            580                 585                 590

Thr Asp Thr Gly Ile Asn Pro Arg Ile Glu Ser Ser Ser Leu Gln Gly
            595                 600                 605

Leu Gly Arg Leu Val Ile Ala Ser Ser Asp Leu Ile Trp Pro Ser Gly
            610                 615                 620

Ile Thr Ile Asp Phe Leu Thr Asp Lys Leu Tyr Trp Cys Asp Ala Lys
625                 630                 635                 640

Gln Ser Val Ile Glu Met Ala Asn Leu Asp Gly Ser Lys Arg Arg Arg
                645                 650                 655

Leu Thr Gln Asn Asp Val Gly His Pro Phe Ala Val Ala Val Phe Glu
            660                 665                 670

Asp Tyr Val Trp Phe Ser Asp Trp Ala Met Pro Ser Val Met Arg Val
            675                 680                 685

Asn Lys Arg Thr Gly Lys Asp Arg Val Arg Leu Gln Gly Ser Met Leu
            690                 695                 700

Lys Pro Ser Ser Leu Val Val Val His Pro Leu Ala Lys Pro Gly Ala
705                 710                 715                 720

Asp Pro Cys Leu Tyr Gln Asn Gly Gly Cys Glu His Ile Cys Lys Lys
                725                 730                 735

Arg Leu Gly Thr Ala Trp Cys Ser Cys Arg Glu Gly Phe Met Lys Ala
            740                 745                 750

Ser Asp Gly Lys Thr Cys Leu Ala Leu Asp Gly His Gln Leu Leu Ala
            755                 760                 765

Gly Gly Glu Val Asp Leu Lys Asn Gln Val Thr Pro Leu Asp Ile Leu
            770                 775                 780

Ser Lys Thr Arg Val Ser Glu Asp Asn Ile Thr Glu Ser Gln His Met
785                 790                 795                 800

Leu Val Ala Glu Ile Met Val Ser Asp Gln Asp Cys Ala Pro Val
                805                 810                 815

Gly Cys Ser Met Tyr Ala Arg Cys Ile Ser Glu Gly Glu Asp Ala Thr
            820                 825                 830
```

```
Cys Gln Cys Leu Lys Gly Phe Ala Gly Asp Gly Lys Leu Cys Ser Asp
        835                 840                 845

Ile Asp Glu Cys Glu Met Gly Val Pro Val Cys Pro Pro Ala Ser Ser
    850                 855                 860

Lys Cys Ile Asn Thr Glu Gly Gly Tyr Val Cys Arg Cys Ser Glu Gly
865                 870                 875                 880

Tyr Gln Gly Asp Gly Ile His Cys Leu Asp Ile Asp Glu Cys Gln Leu
                885                 890                 895

Gly Glu His Ser Cys Gly Glu Asn Ala Ser Cys Thr Asn Thr Glu Gly
                900                 905                 910

Gly Tyr Thr Cys Met Cys Ala Gly Arg Leu Ser Glu Pro Gly Leu Ile
                915                 920                 925

Cys Pro Asp Ser Thr Pro Pro His Leu Arg Glu Asp Asp His His
    930                 935                 940

Tyr Ser Val Arg Asn Ser Asp Ser Glu Cys Pro Leu Ser His Asp Gly
945                 950                 955                 960

Tyr Cys Leu His Asp Gly Val Cys Met Tyr Ile Glu Ala Leu Asp Lys
                965                 970                 975

Tyr Ala Cys Asn Cys Val Val Gly Tyr Ile Gly Glu Arg Cys Gln Tyr
                980                 985                 990

Arg Asp Leu Lys Trp Trp Glu Leu Arg His Ala Gly His Gly Gln Gln
            995                 1000                1005

Gln Lys Val Ile Val Val Ala Val Cys Val Val Val Leu Val Met
    1010                1015                1020

Leu Leu Leu Leu Ser Leu Trp Gly Ala His Tyr Tyr Arg Thr Gln
    1025                1030                1035

Lys Leu Leu Ser Lys Asn Pro Lys Asn Pro Tyr Glu Glu Ser Ser
    1040                1045                1050

Arg Asp Val Arg Ser Arg Arg Pro Ala Asp Thr Glu Asp Gly Met
    1055                1060                1065

Ser Ser Cys Pro Gln Pro Trp Phe Val Val Ile Lys Glu His Gln
    1070                1075                1080

Asp Leu Lys Asn Gly Gly Gln Pro Val Ala Gly Glu Asp Gly Gln
    1085                1090                1095

Ala Ala Asp Gly Ser Met Gln Pro Thr Ser Trp Arg Gln Glu Pro
    1100                1105                1110

Gln Leu Cys Gly Met Gly Thr Glu Gln Gly Cys Trp Ile Pro Val
    1115                1120                1125

Ser Ser Asp Lys Gly Ser Cys Pro Gln Val Met Glu Arg Ser Phe
    1130                1135                1140

His Met Pro Ser Tyr Gly Thr Gln Thr Leu Glu Gly Gly Val Glu
    1145                1150                1155

Lys Pro His Ser Leu Leu Ser Ala Asn Pro Leu Trp Gln Gln Arg
    1160                1165                1170

Ala Leu Asp Pro Pro His Gln Met Glu Leu Thr Gln
    1175                1180                1185

<210> SEQ ID NO 5
<211> LENGTH: 1233
<212> TYPE: PRT
<213> ORGANISM: Homo Sapiens

<400> SEQUENCE: 5

Thr Gln Val Cys Thr Gly Thr Asp Met Lys Leu Arg Leu Pro Ala Ser
```

-continued

```
1               5                   10                  15
Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
                35                  40                  45

Leu Ser Phe Leu Gln Asp Ile Gln Glu Val Gln Gly Tyr Val Leu Ile
                50                  55                  60

Ala His Asn Gln Val Arg Gln Val Pro Leu Gln Arg Leu Arg Ile Val
65              70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
                100                 105                 110

Gly Gly Leu Arg Glu Leu Gln Leu Arg Ser Leu Thr Glu Ile Leu Lys
                115                 120                 125

Gly Gly Val Leu Ile Gln Arg Asn Pro Gln Leu Cys Tyr Gln Asp Thr
                130                 135                 140

Ile Leu Trp Lys Asp Ile Phe His Lys Asn Asn Gln Leu Ala Leu Thr
145             150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
                180                 185                 190

Leu Thr Arg Thr Val Cys Ala Gly Gly Cys Ala Arg Cys Lys Gly Pro
                195                 200                 205

Leu Pro Thr Asp Cys Cys His Glu Gln Cys Ala Ala Gly Cys Thr Gly
                210                 215                 220

Pro Lys His Ser Asp Cys Leu Ala Cys Leu His Phe Asn His Ser Gly
225             230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
                260                 265                 270

Cys Val Thr Ala Cys Pro Tyr Asn Tyr Leu Ser Thr Asp Val Gly Ser
                275                 280                 285

Cys Thr Leu Val Cys Pro Leu His Asn Gln Glu Val Thr Ala Glu Asp
                290                 295                 300

Gly Thr Gln Arg Cys Glu Lys Cys Ser Lys Pro Cys Ala Arg Val Cys
305             310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
                340                 345                 350

Ala Phe Leu Pro Glu Ser Phe Asp Gly Asp Pro Ala Ser Asn Thr Ala
                355                 360                 365

Pro Leu Gln Pro Glu Gln Leu Gln Val Phe Glu Thr Leu Glu Glu Ile
                370                 375                 380

Thr Gly Tyr Leu Tyr Ile Ser Ala Trp Pro Asp Ser Leu Pro Asp Leu
385             390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
                420                 425                 430
```

```
Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                    485                 490                 495

His Cys Trp Gly Pro Gly Pro Thr Gln Cys Val Asn Cys Ser Gln Phe
                500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
    610                 615                 620

Arg Ala Ser Pro Leu Thr Ser Ile Ile Ser Ala Val Val Gly Ile Leu
625                 630                 635                 640

Leu Val Val Val Leu Gly Val Val Phe Gly Ile Leu Ile Lys Arg Arg
                645                 650                 655

Gln Gln Lys Ile Arg Lys Tyr Thr Met Arg Arg Leu Leu Gln Glu Thr
            660                 665                 670

Glu Leu Val Glu Pro Leu Thr Pro Ser Gly Ala Met Pro Asn Gln Ala
        675                 680                 685

Gln Met Arg Ile Leu Lys Glu Thr Glu Leu Arg Lys Val Lys Val Leu
    690                 695                 700

Gly Ser Gly Ala Phe Gly Thr Val Tyr Lys Gly Ile Trp Ile Pro Asp
705                 710                 715                 720

Gly Glu Asn Val Lys Ile Pro Val Ala Ile Lys Val Leu Arg Glu Asn
                725                 730                 735

Thr Ser Pro Lys Ala Asn Lys Glu Ile Leu Asp Glu Ala Tyr Val Met
            740                 745                 750

Ala Gly Val Gly Ser Pro Tyr Val Ser Arg Leu Leu Gly Ile Cys Leu
        755                 760                 765

Thr Ser Thr Val Gln Leu Val Thr Gln Leu Met Pro Tyr Gly Cys Leu
    770                 775                 780

Leu Asp His Val Arg Glu Asn Arg Gly Arg Leu Gly Ser Gln Asp Leu
785                 790                 795                 800

Leu Asn Trp Cys Met Gln Ile Ala Lys Gly Met Ser Tyr Leu Glu Asp
                805                 810                 815

Val Arg Leu Val His Arg Asp Leu Ala Ala Arg Asn Val Leu Val Lys
            820                 825                 830

Ser Pro Asn His Val Lys Ile Thr Asp Phe Gly Leu Ala Arg Leu Leu
        835                 840                 845
```

```
Asp Ile Asp Glu Thr Glu Tyr His Ala Asp Gly Gly Lys Val Pro Ile
850                 855                 860

Lys Trp Met Ala Leu Glu Ser Ile Leu Arg Arg Phe Thr His Gln
865                 870                 875                 880

Ser Asp Val Trp Ser Tyr Gly Val Thr Val Trp Glu Leu Met Thr Phe
                885                 890                 895

Gly Ala Lys Pro Tyr Asp Gly Ile Pro Ala Arg Glu Ile Pro Asp Leu
                900                 905                 910

Leu Glu Lys Gly Glu Arg Leu Pro Gln Pro Ile Cys Thr Ile Asp
            915                 920                 925

Val Tyr Met Ile Met Val Lys Cys Trp Met Ile Asp Ser Glu Cys Arg
930                 935                 940

Pro Arg Phe Arg Glu Leu Val Ser Glu Phe Ser Arg Met Ala Arg Asp
945                 950                 955                 960

Pro Gln Arg Phe Val Val Ile Gln Asn Glu Asp Leu Gly Pro Ala Ser
                965                 970                 975

Pro Leu Asp Ser Thr Phe Tyr Arg Ser Leu Leu Glu Asp Asp Met
                980                 985                 990

Gly Asp Leu Val Asp Ala Glu Glu Tyr Leu Val Pro Gln Gln Gly Phe
                995                 1000                1005

Phe Cys Pro Asp Pro Ala Pro Gly Ala Gly Gly Met Val His His
    1010                1015                1020

Arg His Arg Ser Ser Ser Thr Arg Ser Gly Gly Gly Asp Leu Thr
    1025                1030                1035

Leu Gly Leu Glu Pro Ser Glu Glu Ala Pro Arg Ser Pro Leu
    1040                1045                1050

Ala Pro Ser Glu Gly Ala Gly Ser Asp Val Phe Asp Gly Asp Leu
    1055                1060                1065

Gly Met Gly Ala Ala Lys Gly Leu Gln Ser Leu Pro Thr His Asp
    1070                1075                1080

Pro Ser Pro Leu Gln Arg Tyr Ser Glu Asp Pro Thr Val Pro Leu
    1085                1090                1095

Pro Ser Glu Thr Asp Gly Tyr Val Ala Pro Leu Thr Cys Ser Pro
    1100                1105                1110

Gln Pro Glu Tyr Val Asn Gln Pro Asp Val Arg Pro Gln Pro Pro
    1115                1120                1125

Ser Pro Arg Glu Gly Pro Leu Pro Ala Ala Arg Pro Ala Gly Ala
    1130                1135                1140

Thr Leu Glu Arg Pro Lys Thr Leu Ser Pro Gly Lys Asn Gly Val
    1145                1150                1155

Val Lys Asp Val Phe Ala Phe Gly Gly Ala Val Glu Asn Pro Glu
    1160                1165                1170

Tyr Leu Thr Pro Gln Gly Gly Ala Ala Pro Gln Pro His Pro Pro
    1175                1180                1185

Pro Ala Phe Ser Pro Ala Phe Asp Asn Leu Tyr Tyr Trp Asp Gln
    1190                1195                1200

Asp Pro Pro Glu Arg Gly Ala Pro Pro Ser Thr Phe Lys Gly Thr
    1205                1210                1215

Pro Thr Ala Glu Asn Pro Glu Tyr Leu Gly Leu Asp Val Pro Val
    1220                1225                1230

<210> SEQ ID NO 6
<211> LENGTH: 630
<212> TYPE: PRT
```

<213> ORGANISM: Homo Sapiens

<400> SEQUENCE: 6

| | | | | | | | | | | | | | | |
|---|---|---|---|---|---|---|---|---|---|---|---|---|---|---|
| Thr | Gln | Val | Cys | Thr | Gly | Thr | Asp | Met | Lys | Leu | Arg | Leu | Pro | Ala | Ser |
| 1 | | | | 5 | | | | | 10 | | | | | 15 | |
| Pro | Glu | Thr | His | Leu | Asp | Met | Leu | Arg | His | Leu | Tyr | Gln | Gly | Cys | Gln |
| | | | 20 | | | | | 25 | | | | | 30 | | |
| Val | Val | Gln | Gly | Asn | Leu | Glu | Leu | Thr | Tyr | Leu | Pro | Thr | Asn | Ala | Ser |
| | | 35 | | | | | 40 | | | | | 45 | | | |
| Leu | Ser | Phe | Leu | Gln | Asp | Ile | Gln | Glu | Val | Gln | Gly | Tyr | Val | Leu | Ile |
| | 50 | | | | | 55 | | | | | 60 | | | | |
| Ala | His | Asn | Gln | Val | Arg | Gln | Val | Pro | Leu | Gln | Arg | Leu | Arg | Ile | Val |
| 65 | | | | | 70 | | | | | 75 | | | | | 80 |
| Arg | Gly | Thr | Gln | Leu | Phe | Glu | Asp | Asn | Tyr | Ala | Leu | Ala | Val | Leu | Asp |
| | | | | 85 | | | | | 90 | | | | | 95 | |
| Asn | Gly | Asp | Pro | Leu | Asn | Asn | Thr | Thr | Pro | Val | Thr | Gly | Ala | Ser | Pro |
| | | | 100 | | | | | 105 | | | | | 110 | | |
| Gly | Gly | Leu | Arg | Glu | Leu | Gln | Leu | Arg | Ser | Leu | Thr | Glu | Ile | Leu | Lys |
| | | 115 | | | | | 120 | | | | | 125 | | | |
| Gly | Gly | Val | Leu | Ile | Gln | Arg | Asn | Pro | Gln | Leu | Cys | Tyr | Gln | Asp | Thr |
| | 130 | | | | | 135 | | | | | 140 | | | | |
| Ile | Leu | Trp | Lys | Asp | Ile | Phe | His | Lys | Asn | Asn | Gln | Leu | Ala | Leu | Thr |
| 145 | | | | | 150 | | | | | 155 | | | | | 160 |
| Leu | Ile | Asp | Thr | Asn | Arg | Ser | Arg | Ala | Cys | His | Pro | Cys | Ser | Pro | Met |
| | | | | 165 | | | | | 170 | | | | | 175 | |
| Cys | Lys | Gly | Ser | Arg | Cys | Trp | Gly | Glu | Ser | Ser | Glu | Asp | Cys | Gln | Ser |
| | | | 180 | | | | | 185 | | | | | 190 | | |
| Leu | Thr | Arg | Thr | Val | Cys | Ala | Gly | Gly | Cys | Ala | Arg | Cys | Lys | Gly | Pro |
| | | 195 | | | | | 200 | | | | | 205 | | | |
| Leu | Pro | Thr | Asp | Cys | Cys | His | Glu | Gln | Cys | Ala | Ala | Gly | Cys | Thr | Gly |
| | 210 | | | | | 215 | | | | | 220 | | | | |
| Pro | Lys | His | Ser | Asp | Cys | Leu | Ala | Cys | Leu | His | Phe | Asn | His | Ser | Gly |
| 225 | | | | | 230 | | | | | 235 | | | | | 240 |
| Ile | Cys | Glu | Leu | His | Cys | Pro | Ala | Leu | Val | Thr | Tyr | Asn | Thr | Asp | Thr |
| | | | | 245 | | | | | 250 | | | | | 255 | |
| Phe | Glu | Ser | Met | Pro | Asn | Pro | Glu | Gly | Arg | Tyr | Thr | Phe | Gly | Ala | Ser |
| | | | 260 | | | | | 265 | | | | | 270 | | |
| Cys | Val | Thr | Ala | Cys | Pro | Tyr | Asn | Tyr | Leu | Ser | Thr | Asp | Val | Gly | Ser |
| | | 275 | | | | | 280 | | | | | 285 | | | |
| Cys | Thr | Leu | Val | Cys | Pro | Leu | His | Asn | Gln | Glu | Val | Thr | Ala | Glu | Asp |
| | 290 | | | | | 295 | | | | | 300 | | | | |
| Gly | Thr | Gln | Arg | Cys | Glu | Lys | Cys | Ser | Lys | Pro | Cys | Ala | Arg | Val | Cys |
| 305 | | | | | 310 | | | | | 315 | | | | | 320 |
| Tyr | Gly | Leu | Gly | Met | Glu | His | Leu | Arg | Glu | Val | Arg | Ala | Val | Thr | Ser |
| | | | | 325 | | | | | 330 | | | | | 335 | |
| Ala | Asn | Ile | Gln | Glu | Phe | Ala | Gly | Cys | Lys | Lys | Ile | Phe | Gly | Ser | Leu |
| | | | 340 | | | | | 345 | | | | | 350 | | |
| Ala | Phe | Leu | Pro | Glu | Ser | Phe | Asp | Gly | Asp | Pro | Ala | Ser | Asn | Thr | Ala |
| | | 355 | | | | | 360 | | | | | 365 | | | |
| Pro | Leu | Gln | Pro | Glu | Gln | Leu | Gln | Val | Phe | Glu | Thr | Leu | Glu | Glu | Ile |
| | 370 | | | | | 375 | | | | | 380 | | | | |
| Thr | Gly | Tyr | Leu | Tyr | Ile | Ser | Ala | Trp | Pro | Asp | Ser | Leu | Pro | Asp | Leu |
| 385 | | | | | 390 | | | | | 395 | | | | | 400 |

```
Ser Val Phe Gln Asn Leu Gln Val Ile Arg Gly Arg Ile Leu His Asn
                405                 410                 415
Gly Ala Tyr Ser Leu Thr Leu Gln Gly Leu Gly Ile Ser Trp Leu Gly
            420                 425                 430
Leu Arg Ser Leu Arg Glu Leu Gly Ser Gly Leu Ala Leu Ile His His
        435                 440                 445
Asn Thr His Leu Cys Phe Val His Thr Val Pro Trp Asp Gln Leu Phe
450                 455                 460
Arg Asn Pro His Gln Ala Leu Leu His Thr Ala Asn Arg Pro Glu Asp
465                 470                 475                 480
Glu Cys Val Gly Glu Gly Leu Ala Cys His Gln Leu Cys Ala Arg Gly
                485                 490                 495
His Cys Trp Gly Pro Gly Pro Thr Gln Cys Val Asn Cys Ser Gln Phe
            500                 505                 510
Leu Arg Gly Gln Glu Cys Val Glu Glu Cys Arg Val Leu Gln Gly Leu
        515                 520                 525
Pro Arg Glu Tyr Val Asn Ala Arg His Cys Leu Pro Cys His Pro Glu
530                 535                 540
Cys Gln Pro Gln Asn Gly Ser Val Thr Cys Phe Gly Pro Glu Ala Asp
545                 550                 555                 560
Gln Cys Val Ala Cys Ala His Tyr Lys Asp Pro Pro Phe Cys Val Ala
                565                 570                 575
Arg Cys Pro Ser Gly Val Lys Pro Asp Leu Ser Tyr Met Pro Ile Trp
            580                 585                 590
Lys Phe Pro Asp Glu Glu Gly Ala Cys Gln Pro Cys Pro Ile Asn Cys
        595                 600                 605
Thr His Ser Cys Val Asp Leu Asp Asp Lys Gly Cys Pro Ala Glu Gln
610                 615                 620
Arg Ala Ser Pro Leu Thr
625                 630

<210> SEQ ID NO 7
<211> LENGTH: 1323
<212> TYPE: PRT
<213> ORGANISM: Homo Sapiens

<400> SEQUENCE: 7

Ser Glu Val Gly Asn Ser Gln Ala Val Cys Pro Gly Thr Leu Asn Gly
1               5                   10                  15
Leu Ser Val Thr Gly Asp Ala Glu Asn Gln Tyr Gln Thr Leu Tyr Lys
            20                  25                  30
Leu Tyr Glu Arg Cys Glu Val Val Met Gly Asn Leu Glu Ile Val Leu
        35                  40                  45
Thr Gly His Asn Ala Asp Leu Ser Phe Leu Gln Trp Ile Arg Glu Val
    50                  55                  60
Thr Gly Tyr Val Leu Val Ala Met Asn Glu Phe Ser Thr Leu Pro Leu
65                  70                  75                  80
Pro Asn Leu Arg Val Val Arg Gly Thr Gln Val Tyr Asp Gly Lys Phe
                85                  90                  95
Ala Ile Phe Val Met Leu Asn Tyr Asn Thr Asn Ser Ser His Ala Leu
            100                 105                 110
Arg Gln Leu Arg Leu Thr Gln Leu Thr Glu Ile Leu Ser Gly Gly Val
        115                 120                 125
Tyr Ile Glu Lys Asn Asp Lys Leu Cys His Met Asp Thr Ile Asp Trp
    130                 135                 140
```

-continued

```
Arg Asp Ile Val Arg Asp Arg Asp Ala Glu Ile Val Lys Asp Asn
145                 150                 155                 160

Gly Arg Ser Cys Pro Pro Cys His Glu Val Cys Lys Gly Arg Cys Trp
            165                 170                 175

Gly Pro Gly Ser Glu Asp Cys Gln Thr Leu Thr Lys Thr Ile Cys Ala
            180                 185                 190

Pro Gln Cys Asn Gly His Cys Phe Gly Pro Asn Pro Asn Gln Cys Cys
            195                 200                 205

His Asp Glu Cys Ala Gly Gly Cys Ser Gly Pro Gln Asp Thr Asp Cys
        210                 215                 220

Phe Ala Cys Arg His Phe Asn Asp Ser Gly Ala Cys Val Pro Arg Cys
225                 230                 235                 240

Pro Gln Pro Leu Val Tyr Asn Lys Leu Thr Phe Gln Leu Glu Pro Asn
                245                 250                 255

Pro His Thr Lys Tyr Gln Tyr Gly Gly Val Cys Val Ala Ser Cys Pro
            260                 265                 270

His Asn Phe Val Val Asp Gln Thr Ser Cys Val Arg Ala Cys Pro Pro
            275                 280                 285

Asp Lys Met Glu Val Asp Lys Asn Gly Leu Lys Met Cys Glu Pro Cys
        290                 295                 300

Gly Gly Leu Cys Pro Lys Ala Cys Glu Gly Thr Gly Ser Gly Ser Arg
305                 310                 315                 320

Phe Gln Thr Val Asp Ser Ser Asn Ile Asp Gly Phe Val Asn Cys Thr
                325                 330                 335

Lys Ile Leu Gly Asn Leu Asp Phe Leu Ile Thr Gly Leu Asn Gly Asp
            340                 345                 350

Pro Trp His Lys Ile Pro Ala Leu Asp Pro Glu Lys Leu Asn Val Phe
            355                 360                 365

Arg Thr Val Arg Glu Ile Thr Gly Tyr Leu Asn Ile Gln Ser Trp Pro
        370                 375                 380

Pro His Met His Asn Phe Ser Val Phe Ser Asn Leu Thr Thr Ile Gly
385                 390                 395                 400

Gly Arg Ser Leu Tyr Asn Arg Gly Phe Ser Leu Leu Ile Met Lys Asn
                405                 410                 415

Leu Asn Val Thr Ser Leu Gly Phe Arg Ser Leu Lys Glu Ile Ser Ala
            420                 425                 430

Gly Arg Ile Tyr Ile Ser Ala Asn Arg Gln Leu Cys Tyr His His Ser
            435                 440                 445

Leu Asn Trp Thr Lys Val Leu Arg Gly Pro Thr Glu Glu Arg Leu Asp
        450                 455                 460

Ile Lys His Asn Arg Pro Arg Arg Asp Cys Val Ala Glu Gly Lys Val
465                 470                 475                 480

Cys Asp Pro Leu Cys Ser Ser Gly Gly Cys Trp Gly Pro Gly Pro Gly
                485                 490                 495

Gln Cys Leu Ser Cys Arg Asn Tyr Ser Arg Gly Gly Val Cys Val Thr
            500                 505                 510

His Cys Asn Phe Leu Asn Gly Glu Pro Arg Glu Phe Ala His Glu Ala
            515                 520                 525

Glu Cys Phe Ser Cys His Pro Glu Cys Gln Pro Met Glu Gly Thr Ala
        530                 535                 540

Thr Cys Asn Gly Ser Gly Ser Asp Thr Cys Ala Gln Cys Ala His Phe
545                 550                 555                 560
```

```
Arg Asp Gly Pro His Cys Val Ser Ser Cys Pro His Gly Val Leu Gly
            565                 570                 575

Ala Lys Gly Pro Ile Tyr Lys Tyr Pro Asp Val Gln Asn Glu Cys Arg
            580                 585                 590

Pro Cys His Glu Asn Cys Thr Gln Gly Cys Lys Gly Pro Glu Leu Gln
            595                 600                 605

Asp Cys Leu Gly Gln Thr Leu Val Leu Ile Gly Lys Thr His Leu Thr
            610                 615                 620

Met Ala Leu Thr Val Ile Ala Gly Leu Val Val Ile Phe Met Met Leu
625                 630                 635                 640

Gly Gly Thr Phe Leu Tyr Trp Arg Gly Arg Arg Ile Gln Asn Lys Arg
            645                 650                 655

Ala Met Arg Arg Tyr Leu Glu Arg Gly Glu Ser Ile Glu Pro Leu Asp
            660                 665                 670

Pro Ser Glu Lys Ala Asn Lys Val Leu Ala Arg Ile Phe Lys Glu Thr
            675                 680                 685

Glu Leu Arg Lys Leu Lys Val Leu Gly Ser Gly Val Phe Gly Thr Val
            690                 695                 700

His Lys Gly Val Trp Ile Pro Glu Gly Glu Ser Ile Lys Ile Pro Val
705                 710                 715                 720

Cys Ile Lys Val Ile Glu Asp Lys Ser Gly Arg Gln Ser Phe Gln Ala
            725                 730                 735

Val Thr Asp His Met Leu Ala Ile Gly Ser Leu Asp His Ala His Ile
            740                 745                 750

Val Arg Leu Leu Gly Leu Cys Pro Gly Ser Ser Leu Gln Leu Val Thr
            755                 760                 765

Gln Tyr Leu Pro Leu Gly Ser Leu Leu Asp His Val Arg Gln His Arg
            770                 775                 780

Gly Ala Leu Gly Pro Gln Leu Leu Leu Asn Trp Gly Val Gln Ile Ala
785                 790                 795                 800

Lys Gly Met Tyr Tyr Leu Glu Glu His Gly Met Val His Arg Asn Leu
            805                 810                 815

Ala Ala Arg Asn Val Leu Leu Lys Ser Pro Ser Gln Val Gln Val Ala
            820                 825                 830

Asp Phe Gly Val Ala Asp Leu Leu Pro Pro Asp Asp Lys Gln Leu Leu
            835                 840                 845

Tyr Ser Glu Ala Lys Thr Pro Ile Lys Trp Met Ala Leu Glu Ser Ile
            850                 855                 860

His Phe Gly Lys Tyr Thr His Gln Ser Asp Val Trp Ser Tyr Gly Val
865                 870                 875                 880

Thr Val Trp Glu Leu Met Thr Phe Gly Ala Glu Pro Tyr Ala Gly Leu
            885                 890                 895

Arg Leu Ala Glu Val Pro Asp Leu Leu Glu Lys Gly Glu Arg Leu Ala
            900                 905                 910

Gln Pro Gln Ile Cys Thr Ile Asp Val Tyr Met Val Met Val Lys Cys
            915                 920                 925

Trp Met Ile Asp Glu Asn Ile Arg Pro Thr Phe Lys Glu Leu Ala Asn
930                 935                 940

Glu Phe Thr Arg Met Ala Arg Asp Pro Pro Arg Tyr Leu Val Ile Lys
945                 950                 955                 960

Arg Glu Ser Gly Pro Gly Ile Ala Pro Gly Pro Glu Pro His Gly Leu
            965                 970                 975

Thr Asn Lys Lys Leu Glu Glu Val Glu Leu Glu Pro Glu Leu Asp Leu
```

```
                980             985             990
Asp Leu Asp Leu Glu Ala Glu Glu  Asp Asn Leu Ala Thr  Thr Thr Leu
            995             1000            1005

Gly Ser  Ala Leu Ser Leu Pro  Val Gly Thr Leu Asn  Arg Pro Arg
    1010             1015            1020

Gly Ser  Gln Ser Leu Leu Ser  Pro Ser Ser Gly Tyr  Met Pro Met
    1025             1030            1035

Asn Gln  Gly Asn Leu Gly Glu  Ser Cys Gln Glu Ser  Ala Val Ser
    1040             1045            1050

Gly Ser  Ser Glu Arg Cys Pro  Arg Pro Val Ser Leu  His Pro Met
    1055             1060            1065

Pro Arg  Gly Cys Leu Ala Ser  Glu Ser Ser Glu Gly  His Val Thr
    1070             1075            1080

Gly Ser  Glu Ala Glu Leu Gln  Glu Lys Val Ser Met  Cys Arg Ser
    1085             1090            1095

Arg Ser  Arg Ser Arg Ser Pro  Arg Pro Arg Gly Asp  Ser Ala Tyr
    1100             1105            1110

His Ser  Gln Arg His Ser Leu  Leu Thr Pro Val Thr  Pro Leu Ser
    1115             1120            1125

Pro Pro  Gly Leu Glu Glu Glu  Asp Val Asn Gly Tyr  Val Met Pro
    1130             1135            1140

Asp Thr  His Leu Lys Gly Thr  Pro Ser Ser Arg Glu  Gly Thr Leu
    1145             1150            1155

Ser Ser  Val Gly Leu Ser Ser  Val Leu Gly Thr Glu  Glu Glu Asp
    1160             1165            1170

Glu Asp  Glu Glu Tyr Glu Tyr  Met Asn Arg Arg Arg  Arg His Ser
    1175             1180            1185

Pro Pro  His Pro Pro Arg Pro  Ser Ser Leu Glu Glu  Leu Gly Tyr
    1190             1195            1200

Glu Tyr  Met Asp Val Gly Ser  Asp Leu Ser Ala Ser  Leu Gly Ser
    1205             1210            1215

Thr Gln  Ser Cys Pro Leu His  Pro Val Pro Ile Met  Pro Thr Ala
    1220             1225            1230

Gly Thr  Thr Pro Asp Glu Asp  Tyr Glu Tyr Met Asn  Arg Gln Arg
    1235             1240            1245

Asp Gly  Gly Gly Pro Gly Gly  Asp Tyr Ala Ala Met  Gly Ala Cys
    1250             1255            1260

Pro Ala  Ser Glu Gln Gly Tyr  Glu Glu Met Arg Ala  Phe Gln Gly
    1265             1270            1275

Pro Gly  His Gln Ala Pro His  Val His Tyr Ala Arg  Leu Lys Thr
    1280             1285            1290

Leu Arg  Ser Leu Glu Ala Thr  Asp Ser Ala Phe Asp  Asn Pro Asp
    1295             1300            1305

Tyr Trp  His Ser Arg Leu Phe  Pro Lys Ala Asn Ala  Gln Arg Thr
    1310             1315            1320

<210> SEQ ID NO 8
<211> LENGTH: 624
<212> TYPE: PRT
<213> ORGANISM: Homo Sapiens

<400> SEQUENCE: 8

Ser Glu Val Gly Asn Ser Gln Ala Val Cys Pro Gly Thr Leu Asn Gly
1               5                   10                  15
```

```
Leu Ser Val Thr Gly Asp Ala Glu Asn Gln Tyr Gln Thr Leu Tyr Lys
             20                  25                  30

Leu Tyr Glu Arg Cys Glu Val Val Met Gly Asn Leu Glu Ile Val Leu
         35                  40                  45

Thr Gly His Asn Ala Asp Leu Ser Phe Leu Gln Trp Ile Arg Glu Val
     50                  55                  60

Thr Gly Tyr Val Leu Val Ala Met Asn Glu Phe Ser Thr Leu Pro Leu
 65                  70                  75                  80

Pro Asn Leu Arg Val Arg Gly Thr Gln Val Tyr Asp Gly Lys Phe
                 85                  90                  95

Ala Ile Phe Val Met Leu Asn Tyr Asn Thr Asn Ser Ser His Ala Leu
                100                 105                 110

Arg Gln Leu Arg Leu Thr Gln Leu Thr Glu Ile Leu Ser Gly Gly Val
             115                 120                 125

Tyr Ile Glu Lys Asn Asp Lys Leu Cys His Met Asp Thr Ile Asp Trp
    130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
                165                 170                 175

Gly Pro Gly Ser Glu Asp Cys Gln Thr Leu Thr Lys Thr Ile Cys Ala
                180                 185                 190

Pro Gln Cys Asn Gly His Cys Phe Gly Pro Asn Pro Asn Gln Cys Cys
            195                 200                 205

His Asp Glu Cys Ala Gly Gly Cys Ser Gly Pro Gln Asp Thr Asp Cys
210                 215                 220

Phe Ala Cys Arg His Phe Asn Asp Ser Gly Ala Cys Val Pro Arg Cys
225                 230                 235                 240

Pro Gln Pro Leu Val Tyr Asn Lys Leu Thr Phe Gln Leu Glu Pro Asn
                245                 250                 255

Pro His Thr Lys Tyr Gln Tyr Gly Gly Val Cys Val Ala Ser Cys Pro
            260                 265                 270

His Asn Phe Val Val Asp Gln Thr Ser Cys Val Arg Ala Cys Pro Pro
            275                 280                 285

Asp Lys Met Glu Val Asp Lys Asn Gly Leu Lys Met Cys Glu Pro Cys
290                 295                 300

Gly Gly Leu Cys Pro Lys Ala Cys Glu Gly Thr Gly Ser Gly Ser Arg
305                 310                 315                 320

Phe Gln Thr Val Asp Ser Ser Asn Ile Asp Gly Phe Val Asn Cys Thr
            325                 330                 335

Lys Ile Leu Gly Asn Leu Asp Phe Leu Ile Thr Gly Leu Asn Gly Asp
            340                 345                 350

Pro Trp His Lys Ile Pro Ala Leu Asp Pro Glu Lys Leu Asn Val Phe
        355                 360                 365

Arg Thr Val Arg Glu Ile Thr Gly Tyr Leu Asn Ile Gln Ser Trp Pro
370                 375                 380

Pro His Met His Asn Phe Ser Val Phe Ser Asn Leu Thr Thr Ile Gly
385                 390                 395                 400

Gly Arg Ser Leu Tyr Asn Arg Gly Phe Ser Leu Leu Ile Met Lys Asn
                405                 410                 415

Leu Asn Val Thr Ser Leu Gly Phe Arg Ser Leu Lys Glu Ile Ser Ala
            420                 425                 430

Gly Arg Ile Tyr Ile Ser Ala Asn Arg Gln Leu Cys Tyr His His Ser
```

```
                435                 440                 445
Leu Asn Trp Thr Lys Val Leu Arg Gly Pro Thr Glu Glu Arg Leu Asp
450                 455                 460

Ile Lys His Asn Arg Pro Arg Arg Asp Cys Val Ala Glu Gly Lys Val
465                 470                 475                 480

Cys Asp Pro Leu Cys Ser Ser Gly Gly Cys Trp Gly Pro Gly Pro Gly
                485                 490                 495

Gln Cys Leu Ser Cys Arg Asn Tyr Ser Arg Gly Gly Val Cys Val Thr
                500                 505                 510

His Cys Asn Phe Leu Asn Gly Glu Pro Arg Glu Phe Ala His Glu Ala
                515                 520                 525

Glu Cys Phe Ser Cys His Pro Glu Cys Gln Pro Met Glu Gly Thr Ala
                530                 535                 540

Thr Cys Asn Gly Ser Gly Ser Asp Thr Cys Ala Gln Cys Ala His Phe
545                 550                 555                 560

Arg Asp Gly Pro His Cys Val Ser Ser Cys Pro His Gly Val Leu Gly
                565                 570                 575

Ala Lys Gly Pro Ile Tyr Lys Tyr Pro Asp Val Gln Asn Glu Cys Arg
                580                 585                 590

Pro Cys His Glu Asn Cys Thr Gln Gly Cys Lys Gly Pro Glu Leu Gln
                595                 600                 605

Asp Cys Leu Gly Gln Thr Leu Val Leu Ile Gly Lys Thr His Leu Thr
610                 615                 620

<210> SEQ ID NO 9
<211> LENGTH: 1283
<212> TYPE: PRT
<213> ORGANISM: Homo Sapiens

<400> SEQUENCE: 9

Gln Ser Val Cys Ala Gly Thr Glu Asn Lys Leu Ser Ser Leu Ser Asp
1               5                   10                  15

Leu Glu Gln Gln Tyr Arg Ala Leu Arg Lys Tyr Tyr Glu Asn Cys Glu
                20                  25                  30

Val Val Met Gly Asn Leu Glu Ile Thr Ser Ile Glu His Asn Arg Asp
            35                  40                  45

Leu Ser Phe Leu Arg Ser Val Arg Glu Val Thr Gly Tyr Val Leu Val
        50                  55                  60

Ala Leu Asn Gln Phe Arg Tyr Leu Pro Leu Glu Asn Leu Arg Ile Ile
65                  70                  75                  80

Arg Gly Thr Lys Leu Tyr Glu Asp Arg Tyr Ala Leu Ala Ile Phe Leu
                85                  90                  95

Asn Tyr Arg Lys Asp Gly Asn Phe Gly Leu Gln Glu Leu Gly Leu Lys
            100                 105                 110

Asn Leu Thr Glu Ile Leu Asn Gly Gly Val Tyr Val Asp Gln Asn Lys
        115                 120                 125

Phe Leu Cys Tyr Ala Asp Thr Ile His Trp Gln Asp Ile Val Arg Asn
130                 135                 140

Pro Trp Pro Ser Asn Leu Thr Leu Val Ser Thr Asn Gly Ser Ser Gly
145                 150                 155                 160

Cys Gly Arg Cys His Lys Ser Cys Thr Gly Arg Cys Trp Gly Pro Thr
                165                 170                 175

Glu Asn His Cys Gln Thr Leu Thr Arg Thr Val Cys Ala Glu Gln Cys
            180                 185                 190
```

-continued

```
Asp Gly Arg Cys Tyr Gly Pro Tyr Val Ser Asp Cys Cys His Arg Glu
            195                 200                 205
Cys Ala Gly Cys Ser Gly Pro Lys Asp Thr Asp Cys Phe Ala Cys
    210                 215                 220
Met Asn Phe Asn Asp Ser Gly Ala Cys Val Thr Gln Cys Pro Gln Thr
225                 230                 235                 240
Phe Val Tyr Asn Pro Thr Thr Phe Gln Leu Glu His Asn Phe Asn Ala
                245                 250                 255
Lys Tyr Thr Tyr Gly Ala Phe Cys Val Lys Lys Cys Pro His Asn Phe
                260                 265                 270
Val Val Asp Ser Ser Ser Cys Val Arg Ala Cys Pro Ser Ser Lys Met
            275                 280                 285
Glu Val Glu Glu Asn Gly Ile Lys Met Cys Lys Pro Cys Thr Asp Ile
    290                 295                 300
Cys Pro Lys Ala Cys Asp Gly Ile Gly Thr Gly Ser Leu Met Ser Ala
305                 310                 315                 320
Gln Thr Val Asp Ser Ser Asn Ile Asp Lys Phe Ile Asn Cys Thr Lys
                325                 330                 335
Ile Asn Gly Asn Leu Ile Phe Leu Val Thr Gly Ile His Gly Asp Pro
                340                 345                 350
Tyr Asn Ala Ile Glu Ala Ile Asp Pro Glu Lys Leu Asn Val Phe Arg
            355                 360                 365
Thr Val Arg Glu Ile Thr Gly Phe Leu Asn Ile Gln Ser Trp Pro Pro
    370                 375                 380
Asn Met Thr Asp Phe Ser Val Phe Ser Asn Leu Val Thr Ile Gly Gly
385                 390                 395                 400
Arg Val Leu Tyr Ser Gly Leu Ser Leu Leu Ile Leu Lys Gln Gln Gly
                405                 410                 415
Ile Thr Ser Leu Gln Phe Gln Ser Leu Lys Glu Ile Ser Ala Gly Asn
                420                 425                 430
Ile Tyr Ile Thr Asp Asn Ser Asn Leu Cys Tyr Tyr His Thr Ile Asn
            435                 440                 445
Trp Thr Thr Leu Phe Ser Thr Ile Asn Gln Arg Ile Val Ile Arg Asp
    450                 455                 460
Asn Arg Lys Ala Glu Asn Cys Thr Ala Glu Gly Met Val Cys Asn His
465                 470                 475                 480
Leu Cys Ser Ser Asp Gly Cys Trp Gly Pro Gly Pro Asp Gln Cys Leu
                485                 490                 495
Ser Cys Arg Arg Phe Ser Arg Gly Arg Ile Cys Ile Glu Ser Cys Asn
            500                 505                 510
Leu Tyr Asp Gly Glu Phe Arg Glu Phe Glu Asn Gly Ser Ile Cys Val
            515                 520                 525
Glu Cys Asp Pro Gln Cys Glu Lys Met Glu Asp Gly Leu Leu Thr Cys
    530                 535                 540
His Gly Pro Gly Pro Asp Asn Cys Thr Lys Cys Ser His Phe Lys Asp
545                 550                 555                 560
Gly Pro Asn Cys Val Glu Lys Cys Pro Asp Gly Leu Gln Gly Ala Asn
                565                 570                 575
Ser Phe Ile Phe Lys Tyr Ala Asp Pro Asp Arg Glu Cys His Pro Cys
                580                 585                 590
His Pro Asn Cys Thr Gln Gly Cys Asn Gly Pro Thr Ser His Asp Cys
            595                 600                 605
Ile Tyr Tyr Pro Trp Thr Gly His Ser Thr Leu Pro Gln His Ala Arg
```

```
                610                 615                 620
Thr Pro Leu Ile Ala Ala Gly Val Ile Gly Gly Leu Phe Ile Leu Val
625                 630                 635                 640

Ile Val Gly Leu Thr Phe Ala Val Tyr Val Arg Arg Lys Ser Ile Lys
                645                 650                 655

Lys Lys Arg Ala Leu Arg Arg Phe Leu Glu Thr Glu Leu Val Glu Pro
                660                 665                 670

Leu Thr Pro Ser Gly Thr Ala Pro Asn Gln Ala Gln Leu Arg Ile Leu
                675                 680                 685

Lys Glu Thr Glu Leu Lys Arg Val Lys Val Leu Gly Ser Gly Ala Phe
            690                 695                 700

Gly Thr Val Tyr Lys Gly Ile Trp Val Pro Glu Gly Glu Thr Val Lys
705                 710                 715                 720

Ile Pro Val Ala Ile Lys Ile Leu Asn Glu Thr Thr Gly Pro Lys Ala
                725                 730                 735

Asn Val Glu Phe Met Asp Glu Ala Leu Ile Met Ala Ser Met Asp His
                740                 745                 750

Pro His Leu Val Arg Leu Leu Gly Val Cys Leu Ser Pro Thr Ile Gln
            755                 760                 765

Leu Val Thr Gln Leu Met Pro His Gly Cys Leu Leu Glu Tyr Val His
770                 775                 780

Glu His Lys Asp Asn Ile Gly Ser Gln Leu Leu Leu Asn Trp Cys Val
785                 790                 795                 800

Gln Ile Ala Lys Gly Met Met Tyr Leu Glu Glu Arg Arg Leu Val His
                805                 810                 815

Arg Asp Leu Ala Ala Arg Asn Val Leu Val Lys Ser Pro Asn His Val
                820                 825                 830

Lys Ile Thr Asp Phe Gly Leu Ala Arg Leu Leu Glu Gly Asp Glu Lys
            835                 840                 845

Glu Tyr Asn Ala Asp Gly Gly Lys Met Pro Ile Lys Trp Met Ala Leu
            850                 855                 860

Glu Cys Ile His Tyr Arg Lys Phe Thr His Gln Ser Asp Val Trp Ser
865                 870                 875                 880

Tyr Gly Val Thr Ile Trp Glu Leu Met Thr Phe Gly Gly Lys Pro Tyr
                885                 890                 895

Asp Gly Ile Pro Thr Arg Glu Ile Pro Asp Leu Leu Glu Lys Gly Glu
                900                 905                 910

Arg Leu Pro Gln Pro Pro Ile Cys Thr Ile Asp Val Tyr Met Val Met
            915                 920                 925

Val Lys Cys Trp Met Ile Asp Ala Asp Ser Arg Pro Lys Phe Lys Glu
            930                 935                 940

Leu Ala Ala Glu Phe Ser Arg Met Ala Arg Asp Pro Gln Arg Tyr Leu
945                 950                 955                 960

Val Ile Gln Gly Asp Asp Arg Met Lys Leu Pro Ser Pro Asn Asp Ser
                965                 970                 975

Lys Phe Phe Gln Asn Leu Leu Asp Glu Glu Asp Leu Glu Asp Met Met
            980                 985                 990

Asp Ala Glu Glu Tyr Leu Val Pro  Gln Ala Phe Asn Ile  Pro Pro Pro
            995                 1000                1005

Ile Tyr  Thr Ser Arg Ala Arg  Ile Asp Ser Asn Arg  Ser Glu Ile
    1010                1015                1020

Gly His  Ser Pro Pro Pro Ala  Tyr Thr Pro Met Ser  Gly Asn Gln
    1025                1030                1035
```

Phe Val Tyr Arg Asp Gly Gly Phe Ala Ala Glu Gln Gly Val Ser
            1040                1045                1050

Val Pro Tyr Arg Ala Pro Thr Ser Thr Ile Pro Glu Ala Pro Val
            1055                1060                1065

Ala Gln Gly Ala Thr Ala Glu Ile Phe Asp Asp Ser Cys Cys Asn
            1070                1075                1080

Gly Thr Leu Arg Lys Pro Val Ala Pro His Val Gln Glu Asp Ser
            1085                1090                1095

Ser Thr Gln Arg Tyr Ser Ala Asp Pro Thr Val Phe Ala Pro Glu
            1100                1105                1110

Arg Ser Pro Arg Gly Glu Leu Asp Glu Glu Gly Tyr Met Thr Pro
            1115                1120                1125

Met Arg Asp Lys Pro Lys Gln Glu Tyr Leu Asn Pro Val Glu Glu
            1130                1135                1140

Asn Pro Phe Val Ser Arg Arg Lys Asn Gly Asp Leu Gln Ala Leu
            1145                1150                1155

Asp Asn Pro Glu Tyr His Asn Ala Ser Asn Gly Pro Pro Lys Ala
            1160                1165                1170

Glu Asp Glu Tyr Val Asn Glu Pro Leu Tyr Leu Asn Thr Phe Ala
            1175                1180                1185

Asn Thr Leu Gly Lys Ala Glu Tyr Leu Lys Asn Asn Ile Leu Ser
            1190                1195                1200

Met Pro Glu Lys Ala Lys Lys Ala Phe Asp Asn Pro Asp Tyr Trp
            1205                1210                1215

Asn His Ser Leu Pro Pro Arg Ser Thr Leu Gln His Pro Asp Tyr
            1220                1225                1230

Leu Gln Glu Tyr Ser Thr Lys Tyr Phe Tyr Lys Gln Asn Gly Arg
            1235                1240                1245

Ile Arg Pro Ile Val Ala Glu Asn Pro Glu Tyr Leu Ser Glu Phe
            1250                1255                1260

Ser Leu Lys Pro Gly Thr Val Leu Pro Pro Pro Tyr Arg His
            1265                1270                1275

Arg Asn Thr Val Val
            1280

<210> SEQ ID NO 10
<211> LENGTH: 626
<212> TYPE: PRT
<213> ORGANISM: Homo Sapiens

<400> SEQUENCE: 10

Gln Ser Val Cys Ala Gly Thr Glu Asn Lys Leu Ser Ser Leu Ser Asp
1               5                   10                  15

Leu Glu Gln Gln Tyr Arg Ala Leu Arg Lys Tyr Tyr Glu Asn Cys Glu
            20                  25                  30

Val Val Met Gly Asn Leu Glu Ile Thr Ser Ile Glu His Asn Arg Asp
        35                  40                  45

Leu Ser Phe Leu Arg Ser Val Arg Glu Val Thr Gly Tyr Val Leu Val
    50                  55                  60

Ala Leu Asn Gln Phe Arg Tyr Leu Pro Leu Glu Asn Leu Arg Ile Ile
65                  70                  75                  80

Arg Gly Thr Lys Leu Tyr Glu Asp Arg Tyr Ala Leu Ala Ile Phe Leu
                85                  90                  95

Asn Tyr Arg Lys Asp Gly Asn Phe Gly Leu Gln Glu Leu Gly Leu Lys

```
            100             105             110
Asn Leu Thr Glu Ile Leu Asn Gly Gly Val Tyr Val Asp Gln Asn Lys
        115             120             125
Phe Leu Cys Tyr Ala Asp Thr Ile His Trp Gln Asp Ile Val Arg Asn
130             135             140
Pro Trp Pro Ser Asn Leu Thr Leu Val Ser Thr Asn Gly Ser Ser Gly
145             150             155             160
Cys Gly Arg Cys His Lys Ser Cys Thr Gly Arg Cys Trp Gly Pro Thr
                165             170             175
Glu Asn His Cys Gln Thr Leu Thr Arg Thr Val Cys Ala Glu Gln Cys
            180             185             190
Asp Gly Arg Cys Tyr Gly Pro Tyr Val Ser Asp Cys His Arg Glu
        195             200             205
Cys Ala Gly Gly Cys Ser Gly Pro Lys Asp Thr Asp Cys Phe Ala Cys
        210             215             220
Met Asn Phe Asn Asp Ser Gly Ala Cys Val Thr Gln Cys Pro Gln Thr
225             230             235             240
Phe Val Tyr Asn Pro Thr Thr Phe Gln Leu Glu His Asn Phe Asn Ala
            245             250             255
Lys Tyr Thr Tyr Gly Ala Phe Cys Val Lys Lys Cys Pro His Asn Phe
            260             265             270
Val Val Asp Ser Ser Ser Cys Val Arg Ala Cys Pro Ser Ser Lys Met
            275             280             285
Glu Val Glu Glu Asn Gly Ile Lys Met Cys Lys Pro Cys Thr Asp Ile
            290             295             300
Cys Pro Lys Ala Cys Asp Gly Ile Gly Thr Gly Ser Leu Met Ser Ala
305             310             315             320
Gln Thr Val Asp Ser Ser Asn Ile Asp Lys Phe Ile Asn Cys Thr Lys
                325             330             335
Ile Asn Gly Asn Leu Ile Phe Leu Val Thr Gly Ile His Gly Asp Pro
            340             345             350
Tyr Asn Ala Ile Glu Ala Ile Asp Pro Glu Lys Leu Asn Val Phe Arg
            355             360             365
Thr Val Arg Glu Ile Thr Gly Phe Leu Asn Ile Gln Ser Trp Pro Pro
370             375             380
Asn Met Thr Asp Phe Ser Val Phe Ser Asn Leu Val Thr Ile Gly Gly
385             390             395             400
Arg Val Leu Tyr Ser Gly Leu Ser Leu Leu Ile Leu Lys Gln Gln Gly
                405             410             415
Ile Thr Ser Leu Gln Phe Gln Ser Leu Lys Glu Ile Ser Ala Gly Asn
            420             425             430
Ile Tyr Ile Thr Asp Asn Ser Asn Leu Cys Tyr Tyr His Thr Ile Asn
            435             440             445
Trp Thr Thr Leu Phe Ser Thr Ile Asn Gln Arg Ile Val Ile Arg Asp
            450             455             460
Asn Arg Lys Ala Glu Asn Cys Thr Ala Glu Gly Met Val Cys Asn His
465             470             475             480
Leu Cys Ser Ser Asp Gly Cys Trp Gly Pro Gly Pro Asp Gln Cys Leu
                485             490             495
Ser Cys Arg Arg Phe Ser Arg Gly Arg Ile Cys Ile Glu Ser Cys Asn
            500             505             510
Leu Tyr Asp Gly Glu Phe Arg Glu Phe Glu Asn Gly Ser Ile Cys Val
            515             520             525
```

```
Glu Cys Asp Pro Gln Cys Glu Lys Met Glu Asp Gly Leu Leu Thr Cys
            530                 535                 540

His Gly Pro Gly Pro Asp Asn Cys Thr Lys Cys Ser His Phe Lys Asp
545                 550                 555                 560

Gly Pro Asn Cys Val Glu Lys Cys Pro Asp Gly Leu Gln Gly Ala Asn
            565                 570                 575

Ser Phe Ile Phe Lys Tyr Ala Asp Pro Asp Arg Glu Cys His Pro Cys
            580                 585                 590

His Pro Asn Cys Thr Gln Gly Cys Asn Gly Pro Thr Ser His Asp Cys
            595                 600                 605

Ile Tyr Tyr Pro Trp Thr Gly His Ser Thr Leu Pro Gln His Ala Arg
            610                 615                 620

Thr Pro
625

<210> SEQ ID NO 11
<211> LENGTH: 113
<212> TYPE: PRT
<213> ORGANISM: Artificial
<220> FEATURE:
<223> OTHER INFORMATION: TtSlyDcas

<400> SEQUENCE: 11

Met Arg Ser Lys Val Gly Gln Asp Lys Val Val Thr Ile Arg Tyr Thr
1               5                   10                  15

Leu Gln Val Glu Gly Glu Val Leu Asp Gln Gly Glu Leu Ser Tyr Leu
            20                  25                  30

His Gly His Arg Asn Leu Ile Pro Gly Leu Glu Glu Ala Leu Glu Gly
        35                  40                  45

Arg Glu Glu Gly Glu Ala Phe Gln Ala His Val Pro Ala Glu Lys Ala
    50                  55                  60

Tyr Gly Ala Gly Ser Gly Ser Ser Gly Lys Asp Leu Asp Phe Gln Val
65                  70                  75                  80

Glu Val Val Lys Val Arg Glu Ala Thr Pro Glu Glu Leu Leu His Gly
                85                  90                  95

His Ala His Gly Gly Gly Ser Arg Lys His His His His His His
            100                 105                 110

His

<210> SEQ ID NO 12
<211> LENGTH: 133
<212> TYPE: PRT
<213> ORGANISM: Artificial
<220> FEATURE:
<223> OTHER INFORMATION: TtSlyDcas-HER1

<400> SEQUENCE: 12

Met Arg Ser Lys Val Gly Gln Asp Lys Val Val Thr Ile Arg Tyr Thr
1               5                   10                  15

Leu Gln Val Glu Gly Glu Val Leu Asp Gln Gly Glu Leu Ser Tyr Leu
            20                  25                  30

His Gly His Arg Asn Leu Ile Pro Gly Leu Glu Glu Ala Leu Glu Gly
        35                  40                  45

Arg Glu Glu Gly Glu Ala Phe Gln Ala His Val Pro Ala Glu Lys Ala
    50                  55                  60

Tyr Gly Ala Gly Ser Pro Pro Leu Met Leu Tyr Asn Pro Thr Thr Tyr
65                  70                  75                  80
```

```
Gln Met Asp Val Asn Pro Glu Gly Lys Gly Ser Ser Gly Lys Asp Leu
             85                  90                  95

Asp Phe Gln Val Glu Val Val Lys Val Arg Glu Ala Thr Pro Glu Glu
            100                 105                 110

Leu Leu His Gly His Ala His Gly Gly Gly Ser Arg Lys His His His
        115                 120                 125

His His His His His
        130

<210> SEQ ID NO 13
<211> LENGTH: 131
<212> TYPE: PRT
<213> ORGANISM: Artificial
<220> FEATURE:
<223> OTHER INFORMATION: TtSlyDcys-HER1

<400> SEQUENCE: 13

Met Arg Ser Lys Val Gly Gln Asp Lys Val Val Thr Ile Arg Tyr Thr
1               5                   10                  15

Leu Gln Val Glu Gly Glu Val Leu Asp Gln Gly Glu Leu Ser Tyr Leu
            20                  25                  30

His Gly His Arg Asn Leu Ile Pro Gly Leu Glu Glu Ala Leu Glu Gly
        35                  40                  45

Arg Glu Glu Gly Glu Ala Phe Gln Ala His Val Pro Ala Glu Lys Ala
    50                  55                  60

Tyr Gly Pro Cys Gly Pro Pro Leu Met Leu Tyr Asn Pro Thr Thr Tyr
65                  70                  75                  80

Gln Met Asp Val Asn Pro Glu Gly Gly Cys Gly Lys Asp Leu Asp Phe
             85                  90                  95

Gln Val Glu Val Val Lys Val Arg Glu Ala Thr Pro Glu Glu Leu Leu
            100                 105                 110

His Gly His Ala His Gly Gly Gly Ser Arg Lys His His His His His
        115                 120                 125

His His His
    130

<210> SEQ ID NO 14
<211> LENGTH: 131
<212> TYPE: PRT
<213> ORGANISM: Artificial
<220> FEATURE:
<223> OTHER INFORMATION: TtSlyD(GSG)-HER1

<400> SEQUENCE: 14

Met Arg Ser Lys Val Gly Gln Asp Lys Val Val Thr Ile Arg Tyr Thr
1               5                   10                  15

Leu Gln Val Glu Gly Glu Val Leu Asp Gln Gly Glu Leu Ser Tyr Leu
            20                  25                  30

His Gly His Arg Asn Leu Ile Pro Gly Leu Glu Glu Ala Leu Glu Gly
        35                  40                  45

Arg Glu Glu Gly Glu Ala Phe Gln Ala His Val Pro Ala Glu Lys Ala
    50                  55                  60

Tyr Gly Ser Gly Pro Pro Leu Met Leu Tyr Asn Pro Thr Thr Tyr Gln
65                  70                  75                  80

Met Asp Val Asn Pro Glu Gly Lys Gly Ser Gly Lys Asp Leu Asp Phe
             85                  90                  95

Gln Val Glu Val Val Lys Val Arg Glu Ala Thr Pro Glu Glu Leu Leu
```

```
                100                 105                 110
His Gly His Ala His Gly Gly Gly Ser Arg Lys His His His His
        115                 120                 125
His His His
    130

<210> SEQ ID NO 15
<211> LENGTH: 129
<212> TYPE: PRT
<213> ORGANISM: Artificial
<220> FEATURE:
<223> OTHER INFORMATION: TtSlyD(CC)-HER1

<400> SEQUENCE: 15

Met Arg Ser Lys Val Gly Gln Asp Lys Val Val Thr Ile Arg Tyr Thr
1               5                   10                  15

Leu Gln Val Glu Gly Glu Val Leu Asp Gln Gly Glu Leu Ser Tyr Leu
            20                  25                  30

His Gly His Arg Asn Leu Ile Pro Gly Leu Glu Glu Ala Leu Glu Gly
        35                  40                  45

Arg Glu Glu Gly Glu Ala Phe Gln Ala His Val Pro Ala Glu Lys Ala
    50                  55                  60

Tyr Gly Cys Pro Pro Leu Met Leu Tyr Asn Pro Thr Thr Tyr Gln Met
65                  70                  75                  80

Asp Val Asn Pro Glu Gly Lys Cys Gly Lys Asp Leu Asp Phe Gln Val
                85                  90                  95

Glu Val Val Lys Val Arg Glu Ala Thr Pro Glu Glu Leu Leu His Gly
            100                 105                 110

His Ala His Gly Gly Gly Ser Arg Lys His His His His His His
        115                 120                 125

His

<210> SEQ ID NO 16
<211> LENGTH: 129
<212> TYPE: PRT
<213> ORGANISM: Artificial
<220> FEATURE:
<223> OTHER INFORMATION: TtSlyD(SS)-HER1

<400> SEQUENCE: 16

Met Arg Ser Lys Val Gly Gln Asp Lys Val Val Thr Ile Arg Tyr Thr
1               5                   10                  15

Leu Gln Val Glu Gly Glu Val Leu Asp Gln Gly Glu Leu Ser Tyr Leu
            20                  25                  30

His Gly His Arg Asn Leu Ile Pro Gly Leu Glu Glu Ala Leu Glu Gly
        35                  40                  45

Arg Glu Glu Gly Glu Ala Phe Gln Ala His Val Pro Ala Glu Lys Ala
    50                  55                  60

Tyr Gly Ser Pro Pro Leu Met Leu Tyr Asn Pro Thr Thr Tyr Gln Met
65                  70                  75                  80

Asp Val Asn Pro Glu Gly Lys Ser Gly Lys Asp Leu Asp Phe Gln Val
                85                  90                  95

Glu Val Val Lys Val Arg Glu Ala Thr Pro Glu Glu Leu Leu His Gly
            100                 105                 110

His Ala His Gly Gly Gly Ser Arg Lys His His His His His His
        115                 120                 125

His
```

<210> SEQ ID NO 17
<211> LENGTH: 128
<212> TYPE: PRT
<213> ORGANISM: Artificial
<220> FEATURE:
<223> OTHER INFORMATION: TgSlyDdeltaIF

<400> SEQUENCE: 17

```
Met Lys Val Glu Arg Gly Asp Phe Val Leu Phe Asn Tyr Val Gly Arg
1               5                   10                  15

Tyr Glu Asn Gly Glu Val Phe Asp Thr Ser Tyr Glu Ser Val Ala Arg
            20                  25                  30

Glu Gln Gly Ile Phe Val Glu Glu Arg Glu Tyr Ser Pro Ile Gly Val
        35                  40                  45

Thr Val Gly Ala Gly Glu Ile Ile Pro Gly Ile Glu Glu Ala Leu Leu
    50                  55                  60

Gly Met Glu Leu Gly Lys Lys Glu Val Val Pro Pro Glu Lys
65                  70                  75                  80

Gly Tyr Gly Ala Thr Gly His Pro Gly Ile Ile Pro Pro His Ala Thr
                85                  90                  95

Ala Ile Phe Glu Ile Glu Val Val Glu Ile Lys Lys Ala Gly Glu Ala
            100                 105                 110

Leu Glu His His His His His His Leu Glu His His His His His His
        115                 120                 125
```

<210> SEQ ID NO 18
<211> LENGTH: 143
<212> TYPE: PRT
<213> ORGANISM: Artificial
<220> FEATURE:
<223> OTHER INFORMATION: TgSlyDcys-HER1

<400> SEQUENCE: 18

```
Met Arg Gly Ser Lys Val Glu Arg Gly Asp Phe Val Leu Phe Asn Tyr
1               5                   10                  15

Val Gly Arg Tyr Glu Asn Gly Glu Val Phe Asp Thr Ser Tyr Glu Ser
            20                  25                  30

Val Ala Arg Glu Gln Gly Ile Phe Val Glu Glu Arg Glu Tyr Ser Pro
        35                  40                  45

Ile Gly Val Thr Val Gly Ala Gly Glu Ile Ile Pro Gly Ile Glu Glu
    50                  55                  60

Ala Leu Leu Gly Met Glu Leu Gly Lys Lys Glu Val Val Pro
65                  70                  75                  80

Pro Glu Lys Gly Tyr Gly Met Pro Cys Gly Pro Pro Leu Met Leu Tyr
                85                  90                  95

Asn Pro Thr Thr Tyr Gln Met Asp Val Asn Pro Glu Gly Gly Cys Ala
            100                 105                 110

Gly Lys Thr Ala Ile Phe Glu Ile Glu Val Val Glu Ile Lys Lys Ala
        115                 120                 125

Gly Glu Ala Gly Gly Gly Ser His His His His His His His
    130                 135                 140
```

<210> SEQ ID NO 19
<211> LENGTH: 10
<212> TYPE: PRT
<213> ORGANISM: Homo sapiens

<400> SEQUENCE: 19

```
Thr Tyr Gln Met Asp Val Asn Pro Glu Gly
1               5                   10

<210> SEQ ID NO 20
<211> LENGTH: 9
<212> TYPE: PRT
<213> ORGANISM: Homo sapiens

<400> SEQUENCE: 20

Met Leu Tyr Asn Pro Thr Thr Tyr Gln
1               5

<210> SEQ ID NO 21
<211> LENGTH: 107
<212> TYPE: PRT
<213> ORGANISM: Homo Sapiens

<400> SEQUENCE: 21

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 22
<211> LENGTH: 105
<212> TYPE: PRT
<213> ORGANISM: Homo Sapiens

<400> SEQUENCE: 22

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 23
<211> LENGTH: 330
<212> TYPE: PRT
<213> ORGANISM: Homo Sapiens
```

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 24
<211> LENGTH: 330
<212> TYPE: PRT
<213> ORGANISM: homo sapiens

<400> SEQUENCE: 24

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 25
<211> LENGTH: 330
<212> TYPE: PRT
<213> ORGANISM: homo sapiens

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
65                  70                  75                  80

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
        100                 105                 110

Pro Ala Pro Glu Ala Ala Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 327
<212> TYPE: PRT
<213> ORGANISM: Homo Sapiens

<400> SEQUENCE: 26

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
```

-continued

```
            115                 120                 125
Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
    195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```